United States Patent [19]

Jalkanen et al.

[11] Patent Number: 5,726,058
[45] Date of Patent: Mar. 10, 1998

[54] SYNDECAN STIMULATION OF CELLULAR DIFFERENTIATION

[76] Inventors: Markku Jalkanen, Rauvolantie 79, FIN-20760 Piispanristi; Leena Alanen-Kurki, Piispankatu 6-E-31, Fin-20500 Turku, both of Finland; Petri Auvinen, Kirschgartenstrasse 5, 69126 Heidelberg, Germany; Panu Jaakkola, Kellonsoittajankatu 13 B 20, FIN 20500 Turku, Finland; Sirpa Leppä, Valkintie 14056, Fin 20660 Littoinen, Finland; Markku Mali, Inkereentie 176, FIN-24280 Salo, Finland; Tapani Vihinen, Kasenkatu 11 C 54, FIN 20700, Finland; Anni Wärri, Johaninkuja 2 AS 2, 21420 Lieto, Finland

[21] Appl. No.: 472,217

[22] Filed: Jun. 7, 1995

Related U.S. Application Data

[60] Division of Ser. No. 206,186, Mar. 7, 1994, which is a continuation-in-part of Ser. No. 988,427, Dec. 1, 1992, abandoned, said Ser. No. 206,186, Mar. 7, 1994, which is a continuation-in-part of PCT/FI93/00514, Dec. 1, 1993.

[51] Int. Cl.[6] .......................... C12N 5/10; C12N 15/63; C07H 21/04
[52] U.S. Cl. ...................... 435/354; 435/320.1; 536/24.1
[58] Field of Search .................. 536/24.1, 23.1; 935/34, 36; 435/320.1, 354, 357

[56] References Cited

FOREIGN PATENT DOCUMENTS

| 335 554 | 10/1989 | European Pat. Off. . |
|---|---|---|
| 455 422 | 11/1991 | European Pat. Off. . |
| 0 462 398 A1 | 12/1991 | European Pat. Off. . |
| WO 90/12033 | 10/1990 | WIPO . |
| WO 92/13274 | 8/1992 | WIPO . |
| WO 93/05167 | 3/1993 | WIPO . |
| WO 94/12162 | 6/1994 | WIPO . |

OTHER PUBLICATIONS

Couchman, J., et al., "Changes in Microfilament And Focal Adhesion Distribution with Loss of Androgen Responsiveness in Cultured Mammary Tumor Cells," *Cancer Res.* 41:263–269 (1981).

Ekblom, P., et al., "Cell–Matrix Interactions and Cell Adhesion During Development," *Ann. Rev. Cell Biol.* 2:27–47 (1986).

Elenius, K., et al., "Binding of Human Syndecan to Extracellular Matrix Proteins," *J. Biol. Chem.* 265(29):17837–17843 (1990).

Elenius, K., et al., "Growth Factors Induce 3T3 Cells to Express bFGF–binding Syndecan," *J. Biol. Chem.* 267(9):6435–6441 (Mar. 25, 1992).

Elenius, K., et al., "Induced Expression of Syndecan in Healing Wounds," *J. Cell Biol.* 114(3):585–595 (Aug. 1991).

Inki, P., et al., "Immunohistochemical Localization of Syndecan in Mouse Skin Tumors Induced by UV Irradiation," *Amer. J. Pathology* 139(6):1333–1340 (Dec. 1991).

Inki, P., et al., "Syndecan in Carcinomas Produced from Transformed Epithelial Cells in Nude Mice," *Lab. Invest.* 66(3):314–323 (1992).

Jalkanen, M., "Biology of Cell Surface Heparan Sulfate Proteoglycans," *Medical Biology* 65:41–47 (1987).

(List continued on next page.)

*Primary Examiner*—George G. Elliott
*Assistant Examiner*—Robert Schwartzman
*Attorney, Agent, or Firm*—Sterne, Kessler, Goldstein & Fox P.L.L.C.

[57] ABSTRACT

Methods are provided for altering levels of syndecan within a cell. The methods include enhancing syndecan expression via administration of growth factors, preventing suppression of syndecan expression via administration of anti-steroid agents, and altering syndecan biochemistry within the cell. The methods are used to induce or maintain cellular differentiation, and to decrease the growth of malignant cells. Application of the methods to the treatment of patients, including humans, is provided.

10 Claims, 23 Drawing Sheets

OTHER PUBLICATIONS

Jalkanen, M., et al., "Binding of Extracellular Effector Molecules by Cell Surface Proteoglycans," in: *Receptors for Extracellular Matrix*, McDonald and Mecham, eds., New York: Harcourt Brace Jovanovich Publishers, pp. 1–37 (Nov. 1991).

Jalkanen, M., et al., "Cell Surface Proteoglycan of Mouse Mammary Epithelial Cells Is Shed by Cleavage of Its Matrix-binding Ectodomain from Its Membrane-associated Domain," *J. Cell Biol.* 105(6,Pt.2):3087–3096 (1987).

Jalkanen, M., et al., "Heparan Sulfate Proteoglycans from Mouse Mammary Epithelial Cells: Localization on the Cell Surface with a Monoclonal Antibody," *J. Cell Biol.* 101:976–984 (1985).

Jalkanen, M., et al., "Loss of Syndecan Expression in Mouse Mammary Epithelial Cells After Transformation With A Point-Mutated c-Ha-ras Proto-Oncogene," *J. Cell. Biochem. Suppl.* 13F:52, Abstract D317, (1989).

Jalkanen, M., et al., "Mouse Mammary Epithelial Cells Produce Basement Membrane And Cell Surface Heparan Sulfate Proteoglycans Containing Distinct Core Proteins," *J. Cell Biol.* 106:953–962 (1988).

Jalkanen, M., et al., "Simultaneous Loss of Syndecan Expression and Epithelial Phenotype in S115 Carcinoma Cells Exposed to Steroids," *J. Cell Biochem. Suppl.* 14F:153, Abstract A113 (1990).

Jalkanen, M., et al., "Stimulation of syndecan gene expression in mesenchymal cells by bFGF and TGFβ," *J. Cell Biochem. Suppl.*15F:223, Abstract CF115 (Oct. 1991).

Jalkanen, M., et al., "Syndecan, a regulator of cell behaviour, is lost in malignant transformation," *Biochem. Soc. Transactions* 19:1069–1072 (Nov. 1991).

Jalkanen, M., et al., "Syndecan Expression Is Suppressed In Steroid-Induced Transformation of Mouse Mammary Tumor Cell Line (S-115)," *J. Cell Biol.* 109:320a, Abstract No. 1758 (1989).

Kiefer, M., et al., "Ligand-affinity cloning and structure of a cell surface heparan sulfate proteoglycan that binds basic fibroblast growth factor," *Proc. Natl. Acad. Sci. USA* 87:6985–6989 (1990).

King, R., et al., "The Role of Receptors in the Steroidal Regulation of Tumour Cell Proliferation," *J. Steroid Biochem.* 7:869–873 (1976).

Koda, J., et al., "Heparan Sulfate Proteoglycans from Mouse Mammary Epithelial Cells," *J. Biol. Chem.* 260(13):8157–8162 (1985).

Leppä, S., et al. "Steroid-induced epithelial-fibroblastic conversion associated with syndecan suppression in S115 mouse mammary tumor cells," *Cell Regulation* 2:1–11 (Jan. 1991).

Leppä, S., et al., "Syndecan expression regulates cell morphology and growth of mouse mammary epithelial tumor cells," *Proc. Natl. Acad. Sci. USA* 89:932–936 (Feb. 1992).

Liotta, L.A., "Tumor Invasion and Metastases-Role of the Extracellular Matrix: Rhoads Memorial Award Lecture," *Cancer Res.* 46:1–7 (1986).

Mali, M., et al., "Sequence of Human Syndecan Indicates a Novel Gene Family of Integral Membrane Proteoglycans," *J. Biol. Chem.* 265(12):6884–6889 (1990).

*Martindale, The Extra Pharmacopoeia*, 29th Ed., Reynolds, J.E.F., Ed., London: The Pharmaceutical Press, pp. 650–651 and 16525 (1989).

Plantefaber, L., et al., "Changes in Integrin Receptors on Oncogenically Transformed Cells," *Cell* 56:281–290 (1989).

Rapraeger, A., et al., "Requirement of Heparan Sulfate for bFGF-Mediated Fibroblast Growth and Myoblast Differentiation," *Science* 252:1705–1708 (Jun. 21, 1991).

Rapraeger, A., et al., "The Cell Surface Proteoglycan from Mouse Mammary Epithelial Cells Bears Chondroitin Sulfate and Heparan Sulfate Glycosaminoglycans," *J. Biol. Chem.* 260(20):11046–11052 (1985).

Rapraeger, A., et al., "Cell Surface Proteoglycan of Mammary Epithelial Cells," *J. Biol. Chem.* 260(7):4103–4109 (1985).

Rapraeger, A., et al., "Cell Surface Proteoglycan Associates with the Cytoskeleton at the Basolateral Cells Surface of Mouse Mammary Epithelial Cells," *J. Cell Biol.* 103(6, pt.2):2683–2696 (1986).

Ruoslahti, E., et al., "Proteoglycans as Modulators of Growth Factor Activities," *Cell* 64:867–869 (Mar. 8, 1991).

Salmivirta, M., et al., "Syndecan from Embryonic Tooth Mesenchyme Binds Tenascin," *J. Biol. Chem.* 266(12):7733–7739 (Apr. 25, 1991).

Salmivirta, M., et al., "Neurite Growth-Promoting Protein (Amphoterin, p30) Binds Syndecan," *Exp. Cell Res.* 200:444–451 (1992).

Sanderson, R., et al., "B Lymphocytes express and lose syndecan at specific stages of differentiation," *Cell Reg.* 1:27–35 (1989).

Saunders, S., et al., "Cell Surface Proteoglycan Binds Mouse Mammary Epithelial Cells to Fibronectin and Behaves as a Receptor for Interstitial Matrix," *J. Cell Biol.* 106:423–430 (1988).

Saunders, S., et al., "Mammary Epithelial Cells Transfected with Antisense cDNA Reduce Cell Surface Syndecan and Become Fibroblastic in Morphology," *J. Cell Biol.* 109:5a, Abstract No. 7 (1989).

Saunders, S., et al., "Molecular Cloning of Syndecan, an Integral Membrane Proteoglycan," *J. Cell Biol.* 108:1547–1556 (1989).

Sanderson, R., et al., "Molecular polymorphism of a cell surface proteoglycan: Distinct structures on simple and stratified epithelia," *Proc. Natl. Acad. Sci. USA* 85:9562–9566 (1988).

Schweigerer, L., et al., "Basic Fibroblast Growth Factor as a Growth Inhibitor for cultured Human Tumor Cells," *J. Clin. Invest.* 80(5):1516–1520 (1987).

Thesleff, I., et al., "Cell Surface Proteoglycan Expression Correlates with Epithelial-Mesenchymal Interaction during Tooth Morphogenesis," *Developmental Biol.* 129:565–572 (1988).

Vaahtokari, A., et al., "Associations between transforming growth factor β1 RNA expression and epithelial-mesenchymal interactions during tooth morphogenesis," *Development* 113:985–994 (Nov. 1991).

Vainio, S., et al., "Epithelial-Mesenchymal Interactions Regulate the Stage-Specific Expression of a Cell Surface Proteoglycan, Syndecan, in the Developing Kidney," *Developmental Biology* 134:382–391 (1989).

Vainio, S., et al., "Expression of Syndecan Gene is Induced Early, Is Transient, and Correlates with Changes in Mesenchymal Cell Proliferation during Tooth Organogenesis," *Developmental Biology* 147:322–333 (Oct. 1991).

Vainio, S., et al., "Syndecan and Tenascin Expression Is Induced by Epithelial–Mesenchymal Interactions in Embryonic Tooth Mesenchyme," *J. Cell Biol.* 108:1945–1954 (1989).

Wilkinson, D., et al., "Expression pattern of the FGF–related proto–oncogene int–2 suggests multiple roles in fetal development," *Development* 105:131–136 (1989).

Yates, J., et al., "Correlation of Growth Properties and Morphology with Hormone Responsiveness of Mammary Tumor Cells in Culture," *Cancer Res.* 41:258–262 (1981).

Yayon, A., et al., "Cell Surface, Heparin–like Molecules Are Required for Binding of Basic Fibroblast Growth Factor to Its High Affinity Receptor," *Cell* 64:841–848 (Feb. 22, 1991).

```
-4138                                    tctagatattcaaactcac cagatggagtgatgtccacc cctattgtgggagtgacta
-4078 gtctttcctctgtcttctga ctcagatgcttagctagctc tttaggacccaccctcacac ctgcaaataatacttattt
-3998 gctctcttagtacctttaac ccagtggagttgacatgaga aattaactaccataatttat aatattcatttcataaatg
-3918 aaaagtaaaataaattaaaa aatagaaaggtttgagcatg atggccagtggtaaaggcc agtggctccaacgcaagtcc
-3838 tgacaaatggtaacgggcct gttcttcaggcttgaggaa gtttattgattgaggctaaa agcaacccaaaggctccact
-3758 tgcctagtgtgaagccctgg atgtgctctcccacactgca tgtccacctgtgtgtcagc acctggaagctgaggatga
-3678 tggggagtccaaggtcatta gctacatagtataggctagc tggggtacatgggtcacaa aagaaaaaaataagcac
-3598 attgtaatcccagcacttga cagaccaatggggggggat tgctgtgagtttaagacagc ctggctacaaagaaaaacc
-3518 ctacccaaaccaagaaaaa tgaaaccagtaatataaata gctattttcatttaaatgc tctaaagacacagcgttaac
-3438 acaaagctctcgtctgtgg ttcctattccctccttctcc cccaggtcttcttaatgta tactttttgttgtcttattt
-3358 gcttgttttgatttggct tttaaagacagggtctcact atgtagctccaactattgg gaactcactagtagaccag
-3278 gctagccagggacttataga gatctacctaccactgcctc ccaagtgctgagactaaagg catgtgacactttgctggt
-3198 tattacaaacatttaaaaag aacatttgaacattaatag atgtatgtatatatatcact ctatgtagtatatatgttag
-3118 acattttcacttgagatac atatttactctcaaaataag tttttgttgttgttttctc ttttaaattattttattt
-3038 ttttttattttttatta ttatatgtaagtacactgta gctgtcttcagacanaccag aagagggagtcagatcttgt
-2958 tacggatggttgtgagcacc atgtggttgctggattcga actctggaccttccgaagag cagtcgggtgtcttaccca
-2878 ctgagccatctcaccagccc cttaaattattttatctt atgtccattggtgttttgcc tgcatgtatgtgtaaagtg
-2798 tcagaaactgaagttacaga ctgttgtgagctaccattgt tgtgggtgctgggacttgaa cctgggtcctctggaagagc
-2718 agtcattattcttaaccact gagccatctctctagccctc gtttttagttttttttttt gttttgtttgttttttgtt
-2638 ttttaagattttcttattt attatatgtaagtacactgt agctgtcttcagacactcca gaagagggcgccagatctcg
-2558 ttatgatggttgtgagcac catggttgctgggaattg aactccagaccttggaaga gcagtcagtgctcttaactg
-2478 ctgagccatctctccagccc cgttttaggtttttgaag acagggtttcctgtgtagct ctagctgtccaggaactagc
-2398 tctgtagaccaggttggcct caaatttagagatttgcctg tctctctgcctctcgagagc tggattaaaagtgtgcagc
-2318 ccaacaatctactcaaagta ggttttgaaaagctttcca tattagagttaactagctt cattcagaaatactgcatg
-2238 gaattcaaatgtgggaccat tcatagctacttggttttc cttcagtgacaggcattcgg catgcctattaggggaagtca
```

FIG.2a

```
-2158  aatggcctggagaagtcatc ctgggtgagagggctaatgc attttcagcttgacagacac tgtcaacctatgcagacagt
-2078  ctgctccagctcagatgtca attgcatgcagacctgcagt cagacgctaagctccctacc tactctccatcagcttagat
-1998  gtaagggtgctggaacaaa  ggctctctctctctctctct ctctctctctctctctctct ttcttagaattagtattcta
-1918  ttttattttatgtaaattgg tacttcacttacatgtatgt ccgtgtgagagtgttgtatc ctctggtactggagttatag
-1838  acagctgtaagtcgccatac agtgctgggaattgaaccc  tgatcctgtggaagaatagt cagtgtgtcttaaccctgag
-1758  ccatctctccaacctcttgc atattgaggacaggaggaa  tcacaagccatgtagggtgc ctgggctgtgaggtcaacag
-1678  gaccatagcctccttcttt  atgtgcctttctctgggtct ccctataggagtgtcttcg  ttgcctctttactgtctcat
-1598  tgatctgggctaaacttatg cagttgaaggaaagatcaa  gctggtcatgtttaaaacat gaaacagcctcatcagttcc
-1518  ctccctgttccgtctcccc  ccccctcccgccccccattt tgagaggacaggaaggtaaa ataccaaagtgtcctatttt
-1438  cctccaaatatcaggctcaa agagctgaagagctgacttc agatcccaaagccactgtgt taggaggcacctgcttttta
-1358  ggtcctaagcttcctgagc  cttgctattggtattcttt  accaagaccctcaaggatct aggcaagaactggcaggat
-1278  ctgtatgtagccatagtta  gacctaggggcagctgagacg ccaaaaggagagtttcctg  aggacaaaagtgttcaaaca
-1198  caactgggtgctggttgttg ggctactcgtgaggtgtgg  tgtgtgtaaaggaggctgtt gaattcccagaaggctggtt
-1118  ccacagtgtagagtctacac tgggacttccgagacgct   gagcctcagatctagcttct cagtccaggccagctgatgt
-1038  ggggctgaggaacaaggatg gatgccatctatgccctgc  cttgcaggtgcaaagggcct ttggcaccatctacagattg
-958   agggcaagacagggctggtt cttcctccttgctctctgcg ctatctgcctcgcctgtagg ctctctgggctcctttgg
-878   actgacacgtctgaaggagc ttggaaactgtgaggtccag gcccatagagaatcatgaa  ggaacaggaattcaactgga
-798   gctccgcagctggttaggcc tgcggtcacctggaaacaa  gaggccattatttttttcct ttgtcttgacaaggaaga
-718   gaagggctttctataaata  gaaagacagcaaaaagaaa  ataataataataataataat aataataataataataaaa
-638   caataacaaagccagctctt ccagacagtgctcatgtctt taaagtctttaaggtctg   gagttccagcaattaagta
-558   aaggaccaagacctcagggg tcccctatcctcagccgtg  ggggtgggaaccatacat  cgatccctcggtttatat
-478   agcctcatcgctgtggggct ccgagttgccccaaatc    ttgctcacctggagacccc  tgggtgtcctcgcccagagg
-398   gcgctgcagcctcgcacgta gagaactaacatcgccctttc tccagggcagtgcctccga  ctccgaccaggacatagta
-318   gcgagtgcacctggtgtctc gtcagctacgcatcaaggaa ggtgcgacgcgggaattaca gattgccggcactccaccagt
-238   gctcaggggaggaagtggg  aagagtgggtgggcttcga  actcagacctgcaagagctg tcctaggagggcgtggaaggg
```

FIG.2b

```
-158  ggtgtggctggatccctggg  gggtggggcgctccaaggg   cggggcaacccaggggggcgg  ggcccgaggggtggagattg
 -78  ggactacccagcccgcgga  gctggggtgggcggctagt   tttgcaactgcagagcctt    ggtttattaaggcggAG
   3  CTCCGGGAGAGGTGCGGG   CCAGAGGAGACAGAGCCTAA  CGCAGAGGAAGGACCTGGC    AGTCGGAGCTGACTCCAGC
  83  CGGCGAAACCTACAGCCCTC GCTCGAGAGAGCAGCAGAGCT GGGCAGGAGCCTGGACAGC    AAAGGCAGAGCAATCAGCA
 163  GAGCCGGCCGGAGCTCCGT  GCAACCGGCAACTCGGATCC  ACGAAGCCCACCGAGCTCCC   GCCGCCGGTCTGGGCAGCAT
                                                                                         Me
 243  GAGACGCGGCGCTCTGGC   TCTGGCCTCTGCCGCTGGCG  CTGCGCCTGCAGCCTGCCT    CCCGgtgagtgtggccggg
                           tArgArgAlaAlaLeuTrpL  euTrpLeuCysAlaLeuAla   LeuArgLeuGlnProAlaLe uPro 323  gcagggctgggaggcggcg  gaagccgggactcgccactc  gccgatgccatgcaggcggc   agcacgtggaggggagggg
 403  agcgggggactttcttccgcg ctgcctggcggatcctggga tgtgagccttaatgagg      actcctgtcccaattcctct
 483  acggtccgtggatgccagga ggctatcccagctcgtggtc  cgggcgtcctgcagagtgga   acctccattggttcccgct
 563  cccaattaagtaaaacgact ccacagggtctgccatctcgc ggccttaggcgctccgcgg    cctaggcgccgcttggagt
 643  tgctctctcccgttgctgtc ttgctggccatctcagcggc  ctgcctccgccagtgtccc    ggaggatgcagtggccatgg
 723  ccaaacgcctttttccataga cctaattcaaaccagactg  caggctgcaccccccagcgcc  gcggagtccgggcgctcggc
 803  cctttgcaccgggcaagtt  tggcacagcagagccggcg   cgggaacagggggaagctga   cgttcgggtggcgggaggg
 883  acgggattaaggctgtttgt gggacacaagagggtggctc  agggacttcgttttttctct   ggctgcccaggtgagccgg
 963  gccgagctggcagcgggagg ttccgggaagttggcttcag  aacgctgaagaccctcccgca  cccaactttgggtgctga
1043  agttgtgctgccccgggagg gcctcctccgcatgcccgc   ttgtgctgaagccgcgcgta   gtgacccgtaggcccggg
1123  tcccctcccccgactcggct ttgtgctgaagccgcgcgta  gggaaggcggtccttggc     ccgccagtagggccgcggg
1203  gaaagagggacgaactgtgga gctggcgactggtggggaa  gcttctggtaggatgcagc    catccacctttggtgggtc
1283  gtctctctaatcagcggct  tggcgacaaagagcttggtc  gagggtacccagaaaagtgc   tctcccgcccaagccgccg
1363  tcgctagcccgccttccaa  cgggcgctttgttctcggcc  cctgtaaccctttccctggga  accgcccagcgctggtc
1443  cttgacgtgggccgggtcct ggtcgccgccagtgtcagc   gctgccctccgtgtccacg    cccctagccccgcaccgc
1523  tgtgaagtccgggtgtcct  ttccactactgccttttgccca accctgaaggcagaggcg   aggtgcggagcctcaggctt
```

FIG.2c

```
1603 tatcctcccggaagtggcag tctcccaccgccacatctgg tctgcttaacttcgatagtc ctggcaaaggcagacacgtg
1683 cacagggaaggagagttgag cgctggtagataccaaggtc gtgtacaaataaagtggcac acgacacgtcccagtcact
1763 gttaatgcattgccttcgct ccttccagtggctggtgtgc tctccatcactctggagccc aagagagggcctccataatt
1843 gtattgcccatgagttgggg ttgtgtggggcgccaaatc agggttctctggagggcta tgaattccgaactgagtctc
1923 ctgtgcactcctggctttaa ggttcaagaaattgtttgag ggttgtggttttgtgggac tcagattatgcctggaatca
2003 tagttaccactgtgtgagaag aaagtggagctactagcat gcctcccggccgcctggc attacctccggctctgttct
2083 ctaggcccaacgtgaggcct cactgggcagtacagatgc agtactgaatttcttccag ccaggatctggaggaggtggt
2163 gttctcttccctgtgtctt tagagaggcagatattcctg tgacctaagccctcaagca cccattaataatgctgagta
2243 gacaactagaggtggcgttt tccggaacttcctgtgtgct ggcctggaggttgaaccct ctaggaaacaggtctaggaa
2323 gtagaattatctcaatgaa ggcttcctggaggaagaaa tgagctgagccccaggtca ctgtctgagcttttaggatca
2403 gactcccacttggaggcaag agtgttcgttttactttttt tttttaagtttagtttattt tctctctaacgaaaacaaa
2483 caaacaaacaaaaaaaaacc ccacattgtttaaaagtggg tgcataagagtgaggacata ttcagagcttcccctttcc
2563 tgaaaaatgaaggcagctgg gatttacttaaaatgagagc acatatcacaattgccagag agctgtcccttttctcagg
2643 ctccctaagctcctgtggga agcaggtcagacagccctgg ggaccagagaactactcccagag gctttgggtgctgcctt
2723 gaatgggaagggggggga gctgctggatcagaggctg ctagcaactactcccagag actgaagcaggtttgtccct
2803 cagtgtcctgtgtcttctg tttcctatatagaataag agaaatggttattgctctg gaatagtgactgctatttg
2883 ttccctttcttcctctccc ttactgtaatcatttggact agtagagacactttccccag gtctggcagaatgggaggga
2963 gtgggggaggcctgtgcttg catgatgtcactgctgctt cagctctccaggagggtgg agtggttgtaacctacctg
3043 tggctcttgatggccacaa taaaacctcattaacacaca ttggtaggggagaagggactg gaaagaatgatgggaaagat
3123 tgatgtttttcctttttttt tttttttttttttggcagta cttctagatctcccctccc ccttgctgcagcaaaattt
3203 ggattcctgaagtcctttga gaatgtataatggtagccag actttttttttttcagtcag ctcaaaattgcctcctata
3283 aagtatccttggttgtttt tgttgttgttgttgttgttg ttttgttttgttttaagaca agtttctctgtatagtcct
3363 ggctgccctgaactcaata tgtagaccaggctgcctca aactcaaagaaatccaccta cttctaactttcagtgctgg
3443 gcctaaggtgtaggccacc aaaagtgctcaactttaca aagcagtcttacttgagca ggattctgaaaccctattt
```

FIG.2d

```
3523  cctttctgttatcttcaaca  atacactgctaggtgtattt  agtccctcatgatgctggc   ctcctcaagtggcgccaggt
3603  caagcagtcctcctggttttt ggtggctctgaagaagactg  tgtcccagtgactggcagtt  tgaattcggagcttctctt
3683  tccttctcagtctttggcag  gcagagtgacactggtgtgc  ccaagcctggagcttctctg  tttaattctagtttatttc
3763  tttatcagactgaaaaacaa  atcaggttggttataattct  tataaacacgaaggtctcac  ctttgcgtacgtctccggct
3843  gtgtgggtctgatgtccctc  gggaatctctgttgaggctg  ctgcagtgtgtgtgcgtgta  gaaagggcaaggtagaatgg
3923  acagaagcgtgctgccacc   ccactgtcctgttcctaaat  gatgaagcactggcccggtg  aagagcctagagaactcct
4003  cggtgggagatgcacacaat  gccaggaagcacacaggagc  ttgagttccagcttggcagt  gtcttctcttggtgactt
4083  atcagctccagctgccctgg  actaacaaacaaggctagct  cactctcagtattgataatc  gaaggtcctggttctgttt
4163  gagactgatctccactcgt   agccttgaactcttagcaat  tctcctgtctcaactttcaa  agagctgaaattacagactc
4243  gagccaccatatgcgactga  aaccttgttcctaatccttg  actgtgaacgactcttgggt  ttggttcttttctccattct
4323  ttagtgtatgttttagttcg  cgtcctacataatctattgc  ccatcttagaaacaacagg   ttagagacagcattgggtcc
4403  agcagagctcacactgaag   ctcagtcctgccactgattt  accgtgtgcagctcaagtgac tcacttccaactcctctgct
4483  cccatctgtagagtagaca   tcaccatacctgctcttttct gcccacattctgtcattaac  atgttcattcataacgatg
4563  gtgcaaaagtgctttgtaag  taaagtgctggggaaatgtt  agctgtcgataatgttagg   gttaacttttattgagtgc
4643  ctgttgtgtgggttggg     tgggttttttagaggctt    ggtagttttcttacttctt   cctactagctttctcct
4723  aagccttatggtatgtatc   attgcctgattgttgagtg   tgtgcactgaggcacgcctg  tgcatgtttgagagtatgct
4803  tgtgcgtgctctcgtgctca  catatgtatgtgtgtgaatac actgagagtgcaggccggc   acactgggctggctgaatc
4883  ctgtgagccctgcctggagt  cctttgggtaaacccctgagt attgggaacacccctgggct  gtgtggagtggctgtttagc
4963  tggctgtagcctacactgtg  cctttgtagcctaaggttga  gctcacatgctattagtatt  actgagtgctaaggaacct
5043  gttgcttggtacagctaag   aactcttcatagaaagttga  gctcacatgctattagtatt  tacagattagtagagcttt
5123  gtctgggtggtacctgctt   gccctctcatgccacaagtg gt ttgagcttggcgaacacact ttgagcttctaggttgcattct
5203  tgtcagcctgggaggtggg   tttcgtggccacaagtgggt  agcttggaatccaagactcc  tggcttctaggttgcattct
5283  cctgtggtcttttccaaggg  aatgctaggggaacatttg   gacattagattattctagt   cccaaagcacacagaacata
5363  ctgttcctaattgccttt    ttttgttttcctccaatct   ggttttgaagtgttgggttt  gaaattgcccctgagagc
5443  ctgcctagtgtgtgcagag   ggaagatagtggaacaggaa  gtctgtagaaagtatcttcc  tttccaggacccttgtgcccc
```

FIG.2e

```
5523  ggagcagagtcagcatggtg  tcatatcgcttttggctatt  ccagaagagatgaggtttta  ggtgagaatgaaccttttag
5603  aaccttctagaaccttctgt  tgagtatgacaggaatgccc  tgaataggtccgaagtgca  tggccactgttgttgtctttt
5683  ccataagcaagcagcttcag  gtacacaataagactagg    ttcttggagtgagaccctgc  acttggtgccattcagctc
5763  cagatggacactggaagtcc  ctacacagcaggctctggga  tggctggctttgctatgtac  tgttgctgctctacaagag
5843  cttccagttactagcctt    tgtcgacgctgggctcgctg  gccaggcttgggcattggag  aagggacaacttgccacctg
5923  gcataggctgtgtgtttgga  gagtcaggaggtctgtgtaa  gcccgcaagtggaggcaagt  ttagtggacttgaggagag
6003  ctcagtaggaaatctctggg  ctagtgacaggcaggtgtgg  tggtggtggcgaggtggcgg  gtctagatctccttttagag
6083  atttgctaggatcgtccc    tgctgactctggaactcaga  ggcctccagaggtgtctcct  ctgggagcctccagccctggaa
6163  tcccatctcctactgtttat  ggctttgtgggctacctaat  tacatagagaagatatgttc  ctctgcctccagcctgcttc
6243  agttctgccagtgactcac   ctgagctgcagcatgt      gtacacaggcgctctcaggg  gctttctgtcctgctgcttc
6323  agcctttctagcccctgtg   ttctcggcagtggtagcatc  tgggaaaccggtcacctct   tatttgcagctccctccctt
6403  tcttggtgtcttccccctt   ttaactactgtctgatggc   cttagactcatgctgaaatt  ctccttttctttgtcctagc
6483  cttgtctgacttcttgtg    atccctggcctgtgaaat    ccgctcagggcctccattt   ctaacagtcacacactgtg
6563  gagagaccgagtcctgggat  ggtgaagctaacctgctgg   gcttctcaagcttcattgg   tttctcttattcctttctgg
6643  aggtactgcctgccccagg   gagtctcagactagaccact  ctggagttggaggtgggca  ggtttttcagatcagtgcct
6723  tggcattcgttgtgggaatg  gggtgatgggccttctggg   caagtcaggctgggggtgg  aggccaggtgatgttctccg
6803  cacccacaccagcagcct    ggcaccctcccaagtccg    ctcatcagcaggaatgaaag  cagtgccggcaggttgggg
6883  cagtgggcaggtgggcgtgt  ttatcgctgtgctcatcagc  tgagtcacgatgccaggcc  cacaagtcctccctggagc
6963  tcacccaccaccacccttgacc cacccaccactagcagg    agtaggcagggcagtgag    acaagaccagctggggtc
7043  tgagaggcaaagggagttg   ttcatgacctggctgtgcat  ggggacttgtgggtgtctca  gatatctctgtgtcagga
7123  ggaagctgtcttaagtgcca  acctgctagagccctgct    gggtgcaggaaatgcacaag  ggagagtgccatcatga
7203  ataggcccatggagctagac  cagtgacgtgacagtgaag   tcagccccacctgtctt     ccgagccagctggagggttt
7283  ttatctcagattctgcgaaa  ccataggaatctagtcaggag cctagactgcaaagcaggct  tcgttgatgctttaacttgc
7363  aggcttcctgggtatgaggg  atacttagaaaggtcccgca  ggtaggagggcatcaggaa  gtagaagggccaggcact
7443  tctatctcctgcattgcccc  cttctcccatctgcctccaagg gtaaaagaccccttccag   tacactgacagagaggaaaa
```

FIG.2f

```
7523  ccctccatctcaccccattt  ggatctgtcgtatcagcatg  tgctggccct
7603  ccctggaattcactggttg   gggacttgagtgtatcagag  ggcacaaagtaacattaac  tctggtatccctgcagcaa
7683  atcggagatccctctccta   ggcgagttcctcagtggatat  ggaggtcaggtttggcctg  tagggcccagcaagagtcg
7763  ttgatgtcactccagcttct  cccgaggaagatgagggtgc  tgtgttgggatcacatctct  cctgaatggcatgttgggg
7843  agggatggagccctttgcttc tgaccctaagcttggtctt   taggtggccacagtctctgg gttctgtcctacctccctgc
7923  ccttgtgtgcttcaaaggca  tgctaaagggactctcggcc  attccgaatggcacagtgtt cttctgttcctcccaccccc
8003  agaaggaggcaggcctggat  tgtagattcctagaagtaag  tggccctgagcatgctgttg atgaacctggaaccaggcag
8083  gctggcatcctaggacctg   tcttccatagaagtctgaa   tcagtctacctttgggactg agtaagggctcctcacata
8163  tcagctggctagtccatctt  ggctgatctaaaccacatta  ggctgaagagaagcatgtg  tacagtctggtccacccgaa
8243  ccacatactggcttttatcag ttctcgtataatttttgcagg taactttttagctcttaagcc tgtctcctcatctgtgaaat
8323  cgggtccctcatatcctgcc  tagaagggcttttgaaaaga  ttaatgaagtagtatgccga gtggttgggttctctctt
8403  gactggagcaagtctctagg  agtactaaggatagcctgct  gtgtgcagcacccccagga  ctgtgctgagtaggagggt
8483  acagagtcttcatgtgaatg  gcccttctggtcttgccccg  aagttagtgttgatgtcata gagtctacaaacatgcctt
8563  tgtccttcctcagaagtcca  agccttctggcagaccag   acattcattcatctccactgagcc tctatgtgagactggctcct
8643  ggcctgagctgtgtgggctg  agctggcgaatgggaaaact  agacacctgggcacctgggt ggggctcgggacagcagtg
8723  tttcagttgtaggcactgtg  ccctgcctgagcttctga   ctgaaggttacccctgagagg aagcaggttccctatagaca
8803  ctaacatagctgggtcagag  tgcaaggtgggtgtgccct   gccctgaccattcagtgca  aaggctgctcttctgggagt
8883  gagagctctgacaggactgt  gatggccgagggtctcaga   gcaaacctgctggcctctc  cccactctgatggatatgtg
8963  ctcttaaacaagtctgactgtc cactttgcctccaatttcaac atctgtaagatagataggc gttatgtctgaaaatggtt
9043  ttaaagattagttagctaat  acagggaaagtgctctgaca  ggtacctggcaccttactca acaagtggctggagtgcctg
9123  attcctaaggtctcgacct   gtccctatgcttcaagtgcc  cctacagccttggtcaggcc cttaggttcctcccaccacc
9203  gctggcccagactagac     tgctgaccctgacccatt   tttccttttaagccaccctg cgtcaactctaaaaggcggt
9283  ggagttgtttatctaggctg  tgaggtgtcagagaaaggac  ctgggccgctttgttcctgt gtgggctggggccactccag
9363  gaactgagaacccaccac   cttttcaaaaacagcctctt  ctcagagtctgcacctcag  ctagccaccatgctgtggga
9443  ccactcccagcatgctctgc  ctttggtttgttcccaggg   gcctcagtgcctttaaaga  tgcacaggcatctttagttc
```

FIG.2g

```
 9523 aaggggaaagaggaaatgaa gtgtatttgctgtggtggt attcctgtcacttgcattct cacagaggctaaagaaattt
 9603 gctctttgtatcttctagtc tcttctttatgatcttttcc catcgttgtatcccaactg cagggcccagttctagaat
 9683 tagccctcccatagaa gccgacttatgctataatgt aatgacaagtatccttag cccttccacaggcattta
 9763 attttcaaaagggcattgca caaccgcagagacactaaga agagaggtttgtgatcaga gtacagcccagcctccca
 9843 gctggtggccggctggtgc agtgtgtcgaaagcagtag tttctgcttcagtgaaactt gaggatccttatttagcca
 9923 gttcaggggcggaatggcca tgcgaagtctatgtgtcaca ggtgtcaggcccccatatcc tgctgagtctagaatcagct
10003 acgtagcagtttgggggta ttgccagactggagtttac atcccagaagcagagaatggt gggttcctatactgctcca
10083 gacaggatctttcccccag tttgtcagccaccctcttc aagtccctggctctgacca gcaagacgtatccaaagaa
10163 actgaggaggccctttactt ctttttaggatagtgtgggg ccagcatgtgggggttgg aatggctttctgtctcttcc
10243 atcatcacaggctacttccc agagacacttttgattctgg catctccagcagtcacctg cccacaatgctttgctgccc
10323 tttgcttcagccactgtatc tggttgtccctgaaggtga gccagagctcctaggcagag agcatgtgctatacaaagcc
10403 gtaggctgggccctgggaac cttcttgctgtcatcctcct gtcaaaccctctatggtatgg tagcccacataaggcttgtg
10483 caaaaacaggccaaaacat aagttatcttttcactctat cggtctcttctcatttccca tgtacgttcggctggccag
10563 gcccaaaagatttgaagaga ggtggctggcaagtctagg gaataggtctatctggttcc ctccagagcagtgcctagt
10643 gagaggctgggctgggcagg gcagggcccctgtcctccaca ttgcctgaagtcccgccctg cccgtcctgctgggatctg
10723 gcaggtcttccagctccaca cccggctctcagctgagcct gctcagagactagtcctggc atgtgggttgcagggctggt
10803 tccagctccaccaggagta tgggcgtctgggtactcatg ggacattgacctgtagtggg tatggagagtggaggaatgg
10883 tacaggcaggtgtgctggtg ctgacggacttgactccggc attgaccttggcttgcagtc tggtgttaaactaacaggga
10963 atgctgacaaaaagacagt tattaaaaccaagacaggat actgctttccactccagcc attcccaagaatcccaaga
11042 cgtacaggaaatgtgcaaca gcagtgggaattgctgagtt ggggatgtgggtgagctgt gtgctcccaggaattttgg
11123 gaaattccctccgttgaaa tgctgtcagttgtgagcct tgagggtgttttgggggtgc tgtgctcccagctaagcag
11203 ctaacagtcctctttacctg ccttgtcctcaccttgcccc acctgggtggcctctcg ttcactccctgctgggtcac
11283 cagtacttcagtcagtct cagcttgattcttgtggag agagaaagttgataaatc agggtgctgtcagccggaa
11363 atttgggtgtcctgaagg caccaatggggcccctccct tctggaggtggctttaggaa ggggtttctggtcttgagg
11443 cctccttacagttcttagc tccatgggagagaagtgagg agttgggtatcgtcaccca gcatgaatcctctggtcacct
```

FIG.2h

```
11523  ctcagcatgcactgtccagc  ctgatctttgagtgccataa  aagaacagaattatcctc   agagcacttcatttcccgcc
11603  agcacagtgggtacagagac  aagctgccagactcccagc   gagggactagttgagcccca gcatggactagttgagcta
11683  gacctgatacagtcccagag  agcctcgttgaggaagctt   gggaaaattcaccagcatt  tcagccaggactggagaaa
11763  agtgattatgggaaagaga   gcagtcaaggatacaaact   taggacacaggatacaaact gagagctaccggataggagt
11843  agttttagtcacaatctct   cctgtccgccctaccctca   ggagacattgcaccttgtag aacagctgccccggagtcca
11923  cctttgggccccctggta    gctcagtagtgtcagcatcc  tctcattgacatcagtcagg ttacacagtggggcagctaa
12003  tgtgaaggcgctaggctggg  aagcagctacttgggaaaa   ctaggttgttcctggtaggc cctagcaggaaggcagttcc
12083  tccttttcttggtggcttta  gggtcttttgaagctttga   atgttccctcagctgcttgg tgaagcaggccctcctggta
12163  ctgtggtgtttgtcttcgaa  gagtgaaggcattggaagta  aagactgatgggcgccttc  ccaggatgctttgcttcttg
12243  cgctggcttacagagctctc  ttgctacctagtgccttgac  tttgaacacccagattcagt agggaacaggagtagaggtc
12323  ttgcctgctgagcccctgc   gcactgcaggaaaagactcc  tctgagtggagccttttcctc ctcaggtgactgcttcaaa
12403  gtacagcagccctctgaggg  gaagtgtcattgacattgt   ggtagttcttgggtccctg  gatacagatgtcatgccag
12483  atcataggtctgttttgtaca gagggaggcgagttctgtag  ctcagagtcctcagtacccc agagttgtggctctagggt
12563  gagagagaagactacagcc   cttcaatcacagtctgacc   tgtgggtagggtagatctc  ttgcatactatgaacctgtt
12643  tgaaaccccctggtatttgc  tgtgaatagagtcttggtt   gggtaagaatggtggatgtt tatcttggtgtgactctcgg
12723  gtgggggtgggggatatgtc  cctgtctttccaatgtagt   atgctgagtggacagagacc gtgtgactgaagcctgggct
12803  cctgaacaggtgtgttg     gtgggggtggggcgcaact   atctggatccagactgctt  gggaatggctgtgaccagc
12883  tcctttgataacagcagctc  tttgtcactggatgttgtga  ctaatggactgttgattc   agttactcggctcccaccca
12963  cagacgccggggcttctgtt  gtggcaccaggcagctgcag  acggcccacatacccccactccc gctttccactccacgaagg
13043  taagttccagcactgccca   aattagagacttgtgagtgg  tcccctcatacccactccc  tgaggcttctcctggaaggc
13123  ctggaatgggcactgggtg   tgtacgtgctgtgttctg    ttagggtcaagaccaggctg ttccttacctggctcgtacc
13203  tccaagtttcaggtgatga   gtcctgatttttgaagtgaa  ggaatccatttaatatcaaa attctgtgaccttaaatttt
13283  tttcttttattatgtgtcat  ttcatatgtacgcatatttt  tttgtctgtgtgtggacatg cttgtggcgatcagaggaca
13363  cttcagaaagtcagttctct  cctgccgtgtgggtcctggg  gaatcaaatccaagttgtca ggcttatcctgaaaataaa
13443  aagtagacagcccttgggat  ccaaagcttcttaggggtgt  gtgtcttagacaccaccagt gttgcacagtggtaacatg
```

FIG.2i

```
13523 acagtgtcctggagtgctga ttggaagccacaggcctctg tgcagggcgtagacttcca gggtacggggcaggtgggcg
13603 ttctctacaaaaacctgta atccggacgtcttggagat gccccctagtatcatgatt ttggtgtgacacagctga
13683 actgtcttcatactcaggat atcatgaagtgctgggtgc agaccactctcagcctcagg cagccagaccccgggctcc
13763 atcagattgcggtgactacc acagagggtggcccttcctc cggtcagtgtggtgtggga gctggcaggaagtggctcca
13843 ggcttccttaagcatcctc tgcccacagcccccaaacatg ttctttggcaatggcttgca actagaggtgaactctctcc
13923 tgtactatgtcctgaccac gctgctgcatctattatacc tttcacacgcgtgatggta cccagcggggctgctaggca
14003 gggttaagcactcatcttgt ttcctgtgctgaagctgtg gtaaagaaactgaggccatt ttccctgagagagatggtc
14083 tcagccaggtcttttctcgg ctggggagcccgaagaaag gatgtactacagtgagtgga cacttgttgctgatggcct
14163 tggtaggtccttcacctgg gaagtgctgtttcttatctg ttagagatgctgacctcagc aggactgaaggaactgcatg
14243 ggagggtgtaggaatgaaagt gagtggggaaaattatctcc agccctagggaagtctgagg cctgtgtcccctttgtcctg
14323 gactgggccctgccttggg tgtctgtccaggtcttgtc tctacagccccagcgatgc ccaaagtagacgagtcaact
14403 ggtccttctttcaccctgt gtccacttctcatgtatcta ccttcataatcctcctagg aaaacaagcctctaactttg
14483 ggtttttcaaatcagccagct tccaggtcgatagtacgaa ccatgaaaatctttcttacc atgaggttgtttttctagtgt
14563 gtgtgtgtgtgtgtgtgtgt gtgtgtgtgtgtgtgtgtgt gtacgtacacatatgtacct ctatcagtgtgctgtgcgtg
14643 taccacagcagactgtgag gaggtcaggcaaactttata aaatcttttttttgctt cacttgagtcccagggtcac
14723 acagtggcaagtgctgagct ctgttctcgtgttcttgattt gttttgtgagcagctgatgt tcttaaggcttgcggaggg
14803 aaaggtagggctggcttgct tctttcccgagtggccggtca atccctagacatctctaagc cgtggccacacgtcctggaa
14883 ggacccaggtcagaagtgat actgagatggccctgtgagc cctctgaaccacacacaggtt gtaaatagtacctgattgtt
14963 acattggagactcgtcagct gggtggatcctggttcaga gggagttattctcccccca catttctctctcttctgggc
15043 tgaagtctcttccttccta cctgtgatgctgtcatgata ggtcccagctgagagtggag gcggggcagtcaggagctg
15123 cttctctttgcttagcagg gttggaagacttggggtgtag gggttggctccccctttccc tgccctgacctggttttctg
15203 gtttcagcagagattcgttc tagaaacttgttgctgtaaac aagatcacaaagcgataagc ttgacaaaaccagggggaa
15283 caaattgctccctgtgaag acccaatcttagctcttaga gaagccctccctttgaaa ttgctgactttcaggcttc
15363 tctgtggaagaggagctca gccgccgtatgtttgcctgg attccaataatctttgcgg ccttgctaccccttgttga
15443 acaaggtctgcactcctaat gctgcctcagtggtctga gacctctaccccatctccag ctttcctccctatgtgaggg
```

FIG.2j

```
15523  agtcagtgggttaggagaga atggagttgagtcctggaat gaggaggaagctatgaactc gggcctgttcctgtctggt
15603  gggtgctcttctccgccgct gaaggaggcagccgcaggga agactaccacaggaatccga gtaccactgagcagtgta
15683  tacaggatgtgggctgatgt gtggtaaggcatgatggc tgatgtgtggaaggcatg ggatctgattgctctgtgga
15763  tgggccacaggagaaattttt gagtgtctactgcagtagtt ctcaacctgtgggttgtgcg cccttggtgggagttacat
15843  attagatatttacattatga ttcataactgtagcaaaatt acaattgtgaaagaaccaag aaatcaccgcagcatgagaa
15923  cctgtattaaagggtcacgg tgttagagaggttgagagcc actcatcctctgggtctagg ccatgcgggctgtaactgc
16003  tctctggagttaagccacag tgaaccagctgtcctgcag atgacttgtgaggctcca aaccttgtcccaggggaga
16083  agagcttgctttgtgcttgt acttttaaaggaagttcagt ggtcttcgggcctgtggct gctgtgtgaagtgcccc
16163  tgtacaataagctgtataga tcgtgtacaactgcagttt cctccgtggtccaccaacc actcctgactccacgatga
16243  gtgaggccagtagggctgtg tgtgggtccctaggccaagc atcctggaccacgatgagcc tcagctagaccactctgat
16323  ctttagcagaggctcctaga gagctggcttcctcct gccttctttttctcttaaaac ttcgtctcaatcggaagctc
16403  ctctgtgcacgtgacctcca gcctgggggtcgccacaaa tcccctcatcacaagacgag cagtcgcgcatgagggacacg
16483  acacttgttacctaccaggc tgtgggttttttgttggttg gttgttttgtttttgtttttgt tttttactgtacagaagt
16563  gttgtgacatcagatgtcag ctgttagtgctgccaccatt ttacaggtagggaactgagg ctgtaagatgtgtgaca
16643  tcgctaaggccactcagttg gtgaggccttaccaaggtca ggtctttggagcctttttgct gaaccatgtacttctatctc
16723  tgttttgttgaaacaaagtc tatatggctctggctagcct ataacccatatgtagacga ggctgacctgaatacactg
16803  cagtcttttatgtctgcctt ctggtggcaggattgaagg catgtgtgatccctcctaactg tacactttaaaaaaaatc
16883  attctttgtttctgtcgtg ccagggcctgtaagatgtt ctgtgctgagctggctatt tggttagtctcattgctga
16963  gcagggcccctgtatcttcc ttctctgtcacttgcttacc tggtcttcctcctgcacta gctatcctagaaccagtact
17043  gagagcaactatggggccaa ctctgccccctgccagcct gcttagctgggggcggtt ccacttccctgccaagtcc
17123  tgtgggactgtgtttgtact ccaccacttcagttcctg gagctggagcaggccaggcg gctgcattcctgcagctgct
17203  gttgccaggagagcccatc ccattcacttcagtctcctt aatgtagagaagccttgtcgaa ttagcttccactgtcccaa
17283  cccaagagtaccctgtcctt tcttcactacagaaggccagg atacagtccttcctgtggct gataagacaggccttgggac
17363  aaggcctgggaccacactgt gtgggcaaagctgcttcagc accgatggctcctccatgcc aagcttggctctgtcttctca
17443  cagttgagagacttctgtgcgc acaccactgtctagctcag ctggacactgtctagctctttctttta aatgtatagatttgggggtg
```

FIG.2k

```
17523  gggtgtgctgaaagctccca  ctgatgcccaagcctgagt  ctcagagtatgatcaattga  tggctttcatgggtatcaca
17603  gcttctgttcccagtcaga   ctccctgaccagtcagagca  tcctggggttagacaatgtc  ccgtcacttgtgcctccac
17683  ctggcaccaggctatgatgt  tatgcattgagggtatgag   aaggaccaggggtttcccag  agttacgcccaggcgcacag
17763  gcaattgtttcctacatgtg  tggctggaatggttgggtga  gccttttcagctgcctacaa  taggaaccaggggatactgg
17843  gcattgaccaaggcatatct  catacccttttcttatcttt  ctgcagCAAATTGTGGCTGT  AAATGTTCCTCCTGAAGATC
                                                            GlnIleValAlaVa       lAsnValProProGluAspG 18923  AGGATGGCTCTGGGGATGAC  TCTGACAACTTCTCTGGCTC  TGGCACAGgtaagactgacc  cagaacactgagatggcata
       lnAspGlySerGlyAspAsp  SerAspAsnPheSerGlySe  rGlyThrG 18003  gatcatggctggagtggtga  gcaggcagtcaccagctt    tagtgaaccccccttcttctc  ccatccccatcctcctagcatt
18083  ggagtcaggacagtgccaaa  aggaagaatgtatccagct   gcaagccactcagctaagag   aaactctcagagaaatgaag
18163  gggttccaccaggccatggg  cagccactagagccaaccct  tggaggagtttgactccact   gagccttggtgtggtgtttc
18243  catctgtgagatgggaatac  tttgcccaagagcctgttag  aagctgtagggaagcacagag  tcggctaggtatagatttgc
18323  tctcacctccatctctcgat  accagttctctgcagagctt  ggggtttgtgtgggaggggtggg  gggtgagggagaaggctg
18403  tgagctgcgagctagcagag  gggtctcccagaagaatggg  gagagctaagaaggaaagtt   gaggtcacagtgggaaggag
18483  accagacaaagggttggaa   ggtagtaaaatgcagccgt   gtattcttgggagccttagg   ccttgggcaagagggtagaa
18563  gaggtttgtcctggctg     cagtcctgtatcagctctgg  tgtcttggccaccgctcaca   gcaggatcccttcccagatt
18643  cccgagaatttctcacagtt  cagagagcacgttcaaccct  ggcaggtgaggctgcaaagg   acagcttttctgcctaatt
18723  ttcaaagtgagttcagcctt  tgctaggtcacctttgggt   ctcagaaggcttcagctcct   ggtagagcatgaatcacgtc
18803  aggcgtgatgctggagacct  ctcctacccctgacaccccaa accccccacctctgaccctgc  agTGCTTTGCCAGATACTT
                                                                                agAlaLeuProAspThrL 18883  TGTCACGGGCAGACACCTTCC  ACTTGGAAGGAGGAGTGTGGCT  GTTGACAGCCACCAGGCCACAG  CTCCAGAGCCCCACCAGCAGC
       euSerArgGlnThrProSer   ThrTrpLysAspValTrpLe    uThrAlaThrProThrA       laProGluProThrSerSer
```

FIG.2I

```
19963 AACACCGAGACTGCTTTTAC CTCTGTCCTGCCAGCCGGAG AGAAGCCCGAGGAGGAGAG  CCTGTGTCCTCCATGTAGAAGC
      AsnThrGluThrAlaPheTh rSerValLeuProAlaGlyG luLysProGluGluGlyGlu  ProValLeuHisValGluAl

19043 AGAGCCTGGCTTCACTGCTC GGGACAAGGAAAAGGAGGTC ACCACCAGCCCAGGGAGAC  CGTGCAGCTCCCCATCACCC
      aGluProGlyPheThrAlaA rgAspLysPheLysGluVal ThrThrArgProArgGluTh rValGlnLeuProIleThrG

19123 AACGGGCCTCAACAGTCAGA GTCACCACAGCCCAGGCAGC TGTCACATCTCATCCGCACG  GGGGCATGCAACCTGGCCTC
      lnArgAlaSerThrValArg ValThrThrThrAlaGlnAlaAl aValThrSerHisProHisGl yGlyMetGlnProGlyLeu

19203 CATGAGACCTGGCTCCCAC  AGCACCTGGTCAACCTGACC ATCAGCCTCCACGTGTGGAG  GGTGGGCGGCACTTCTGTCAT
      HisGluThrTrpSerAlaProTh rAlaProGlyGlnProAspH isGlnProProArgValGlu GlyGlyGlyThrSerVal Il

19283 CAAAGAGAGGTTGTCGAGGATG GAACTGCCAATCAGCTTCCC GCAGGAGAGGGCTCTGGAGA  ACAAgtgagtggctttgcat
      eLysGluValValGluAspG lyThrAlaAsnGlnLeuPro AlaGlyGluGlySerGlyGl uGln 19363 ttcctggtggtgccactagtg cctgcacctggccgcctaat gtcctcattacagtgacagg tgacagggtccacctttcct
19443 cctgcccgaaacagactgat tgcaagatcaggaggtgggc gactccttagatgtcattca ggagcttacagcagggtgaa
19523 ttttccgtcttagacctcta tgggaatttcacacaacaa tgtgtacgttgtgtcactgg aggcggtatctgtgtcttgg
19603 cctgccagggtcccaggtgt gactgactgcattccttgac agatgctggtataggttggc tacgtctgatgggggtggca
19683 ggggatcccatcaggtatgg cactgccaggttgctgttg tgtcagtggctccagctgac ctgatcccaacctacccttc
19763 tgtagGACTTCACCTTTGAA ACATCTGGGGAGAACACAGC TGTGGCTGCCGTAGAGCCCG GCCTGCGGAATCAGCCCCG
      AspPheThrPheGlu ThrSerGlyGluAsnThrAl aValAlaAlaValGluPro  lyLeuArgAsnGlnProPro 19843 GTGGACGAAGGAGGCCACAGG TGCTTCTCAGAGCCTTTTGG ACAGGAAGGAAGTGCTGGGA  Ggtgagtcttcttcaggtg
      ValAspGluValAlaThrGl yAlaSerGlnSerLeuLeuA spArgLysGluValLeuGly G
```

FIG.2m

```
20923  gagaggaggaggcaggtggt  ggctctgaggtagcctgggt  tgctgggtgaagcatcttt   agcagcaggtggggaagga
20003  ggagggtcaattctactcca  ggccactcctagcctgtcc   gtctagtctgggagagacta  ccactgaccccgtggagcta
20083  ctgatctgagcctgcctctg  ttcactcccctagtGTCATT  GCCGGAGGCCTAGTGGGCCT  CATCTTTGCTGTGCCTGG
                                                 lyValIle AlaGlyGlyLeuValGlyLe uIlePheAlaValCysLeuV 20163  TGGCTTTCATGCTGTACCGG  ATGAAGAAGAAGGACGAAGG  CAGCTACTCCTTGGAGGAGC  CCAAACAAGCCAATGGCGGT
       alAlaPheMetLeuTyrArg  MetLysLysLysAspGluGl  ySerTyrSerLeuGluGluP  roLysGlnAlaAsnGlyGly 20243  GCCTACCAGAAACCACCAA   GCAGGAGGAGTTCTACGCCT  GATGGGGAAATAGTTCTTTC  TCCCCCCACAGCCCCTGCCA
       AlaTyrGlnLysProThrLy  sGlnGluGluPheTyrAla 20323  CTCACTAGGCTCCCCACTTGC CTCTTCTGTGAAAAACTTCA  AGCCCTGGCCTCCCCACCAC  TGGGTCATGTCCTCTGCACC
20403  CAGGCCCTTCCAGTCTGTTCC TGCCGAGCGGTCCCAGGGT   GTGCTGGGAACTGATTCCC   TCCTTTGACTTCTGCCTAGA
20483  AGCTTGGGTGCAAAGGGTTT  CTTGCATCTGATCTTTCTAC  CACAACCACACCTGTGTCC   ACTCTTCTGACTTGGTTCT
20563  CCAAATGGGAGAGAGACCCAG CTCTGGACAGAAAGGGGACC  CGACTCTTTGGACCTAGATG  GCCTATTGCGGCTGGAGGAT
20643  CCTGAGGACAGGAGAGGGGC  TTCGGCTGACCAGCCATAGC  ACTTACCCATAGAGACCGCT  AGGTTGGCCGTGCTGTGGTG
20723  GGGGATGGAGAGGCCTGAGCTC CTTGGAATCCACTTTTCATT AGAGCCCCAGCAGACAGACTI  CAACTGGTTGTTTGCACATAT
20803  TTTCTCTAATTTCTCTGTTC  AGAGCCCCAGCAGACCTTAT  GTTGACTGGTGTCCCTCACC
20883  TCGCTTCCCCTAATCTACATT CAGGAGACCGAATCGGGGGT  TAATAAGACTTTTTTTGTT   TTTGTTTTGTTTTTAACCT
21963  AGAAGAACCAAATCTGGACG  GCAAAACGTAGGCTTAGTTT  GTGTGTTGTCTCTGAGTTTG  TCGCTCATGGTACAACAGG
21043  GTATGGACTATCTGTATGGT  GCCCCATTTTTGGGGGCCCG  TAAGTAGGCTGGCTAGTCCA  GGATACTGTGGAATAGCCAC
21123  CTCTTGACCAGTCATGCCTG  TGTGCATGGACTCAGGGCCA  CGGCCTTGGCCTGGGCCACC  GTGACATTGGAAGAGCCTGT
21203  GTGAGAACTTACTCGAAGTT  CACAGTCTAGGAGTGGAGGG  GAGGAGACTGTAGAGTTTTG  GGGGAGGGGTGGCAAGGGTG
21283  CCCAAGCGTCTCCCCACCTTT CACAGTACCATCTCTAGTCATCC TTCCTCCCGGAAGTTGACAA  GACACATCTTGAGTATGGCT
21363  GGCACTGGTTCCTCCTCCAGC GAACCAAGTTCACCTTCAGC  TCCTGTGGCCCCGCCCCCAG  GCTGGAGTCAGAAATGTTTC
```

FIG. 2n

```
21443  CCAAAGAGTGAGTCTTTTGC  TTTTGGCAAAACGCTACTTA  ATCCAATGGGTTCTGTACAG  TAGATTTTGCAGATGTAATA
21523  AACTTTAATATAAAGGAGTC  CTATGAACTCTACTGCTTCT  GCTTCTTCTTCTCTGGACTG  GTGGTATAGATATAGCCACC
21603  CTTTGCCAAACCCTGGTAG   CTCGGGGAAGCTTGGCTTAA  GGCTGCACGCCTCCAATCCC  CCAAAGGTAGGATCCTGGCT
21683  GGGTCCAGGGTTCCTCTGAT  TTATTGGTTTTGTTGTGT    GTGTTGTGTTTTTCTTTTGG  CTAAACTTCTTTTGGAAGTT
21763  GGTAAGTTCAGCAGCCAAGGTTT TACAGGCCCTGATGTCTGTT CTTCTAAATGGTTTAAGTAA  TTGGGACTCTAGCACATCTT
21843  GACCTAGGGTCACTAGAGCT  AAGCTTGCTTTGCAGGGCAG  ACACCTGGGACAGCAGCCTTCCT CCCTCATGTTGCTGGGACA
21923  CTGCTGAGCACCCCTTGCTT  ACTTAGCTCAGTGATGTTCC  AGCTCCTGGCTAGGCTGCTC  AGCCACTCAGCTAGACAAAA
22003  GATCTGTGCCCTGTGTTTCA  TCCCAGAGCTTGTTGCCAGA  TCACATGGCTGGATGTGATG  TGGGGTGGGGGTGGGGTCAT
22083  ATCTGAGACAGCCCTCAGCT  GAGGGCTTGTGTGGGACAGT  CAAGCCTCAGGCTGGCGCTC  ATTCATATAATTGCAATAAA
22163  tggtacgtgtccatttggac  agcagacactttggtgtact  tgtgcagtctcttttggtc   tggaccatgtccaactctat
22243  ctggtttttggaatggggagc ctaactggcctgtgttctgg  cttggtaccaaatagcaaca  gtcagtggcatcctgccca
22323  ggccccagggcaggactatg  ctcttgccatatccaggact  cccgactttgcacctgtttt  ccctctgtgtagcatcat
22403  gaactccagctaggttgttc  ctttccctgggtcaggagg   attctgctgactctgaatgt  caggattgcttttgttctg
22483  tttgcttattgggcaattct  caaccttcactagcaacagt  ctcatgtgtcaggattacaa  gtattgcttgcacattgagg
```

FIG. 2o

```
TCTAGAACAC TTATTAAGAG CCAGGCACTG AAAAGTGCAG ACTCCCTCAT TCATCCTGG    60
CCGTGCTTAC AAGTAGTTTC CATGCTCTGG TAACCCTGTG CAGAGGGCAG CGTGGGAGGC   120
GGGCCGCTTG GTGGACGGTC ATGGGGGCTC TGCATGGGTG GTTGCCCTTG CCTCAGAAGA   180
ACTCCCTAAG TAAGAGCAAG TTAGCCTCCC TAACCCCTGG TGGGTTGTTG CTTCTTTTCT   240
CCTCTTGTTT CTGCCAAGAG AGGGTGGACC AAGAAGACCC CAGCCTACAG AACATGTGAT   300
CCAAATAAAC TTCTTTTTAG TATAAATGTC CTAGCCTGTG ACGTTCTGGT AGACTAGCAC   360
AAGATGGACC AAGACAACTC TCATCGAGAC TCTGAGGAAC GAACTGGCAT CACATGGGAA   420
CAGGAAATGA AGCTTAGAGA GAGGTTCTGT GGCTTGTCCA ACATGGCTGT AGTTTAAATC   480
CAGCTTGCCA CCAAAGCACA CACATTTCAC TGCTGTGCTG GGCCGGGCCT CAGATCCCAG   540
GGGCTCCGGA GCTAGAAGGA CACGTGTATC AGCCATGGCT TCAGTTTATT GCTGTATACT   600
CTGTGCTTCT GGCTCTCATG GAAAAGACAG ACATTGGGGT TCTTATAATC TCTCCCTCTC   660
CCCTCCCCAC ACTCTATCCC CAAAGGAGGC ACCACTTCTG CAGGTAAATG TTATCTTCAA   720
AGCGCTCACA TCGCAACCTT TGCCCACACC ATCTCATTAA AGGAATTGGC AGTGACTTTA   780
AGGTGAAAGA ACTCGGTGGC TACGTGTTAT ATAAATTTGC ATCTGGGTCT CAGAGCTGGA   840
AGGAAGGCAC TCCCATACAT GCAGTCTGTA CATGCAGTCG GATGATGGAC CAACAACACA   900
TTGTGATTTA TGCCCCTGCT GGTGAGCCCA GGAATCCCTG TAGCACTCTC TCTCAGCTCT   960
AGGGCCCTGC TTGTGTATGG AAAACGCTTA GTGTTTTATA GGTATTTTGT CAGAATACTT  1020
TAAGGAACTT GACCAAAGTT ACAGGGAGGT TAGACAGATT GTCATGGTAT ACTCACCTCT  1080
GTCTCTGACC CTCCTAACTG GGACCTCTTT AGTCTCCCTT GAGGCAGGGA GTGCCACATG  1140
CATGTGTCCA GGCACATGTC TCCTGGTTTA CCTCCCAACG CACCTCAAGT CCCCAAGGTA  1200
GGTAGGCACT TGTATTCTGT AATTCAGAGA GGCAAATCAA ACTGTTACAA TGTTTGCCCA  1260
AAGCTCCCCA AGCAAAGTGG CCCTAAGAGT GAGCAAAGAG ACTGCGTGCC TTCACTGCCT  1320
GTGTGAATCC CTGCAGATAG TCTCTCATCT TGGTGCCCTT CCCACAGAGG CTGGGGCGGC  1380
AGGAGGGAGC CTGGACAGCT CAGACACTGG GTCATTGATG ACTGTTGTGT GGGATACCTG  1440
CCGGGGCGCA GGAGTGAGCC ATGCCACCCC AGGAAGTGGG TCAGGGTGAC TCTTCTTGGC  1500
ACACCTGGGA GGATGTAGCT GGTGCTGGCA CACCCACCGT CACGAGAGCT TCCTGTCCAA  1560
ACCTTCAACA AAGGCGGCTT CTTGAGACAG GCTAGACTGA AGTCACCAGC CTTGGGTGGG  1620
GTCCACTATG TAACCTCAGT GCTCAGGAAC CCTTTCCCAT ACTGTCTGGA ACTATACTGT  1680
ATGTAGCTGG GTTCCACGC ATGTGTGCCT GCACCCAGTC CATCTCATCT TCTATCTCCC  1740
TCCCCTTTCC CGCTTCCCCC CTCCCCACTC TCCATCTCAT CTTCCATCCC CACCTCTTCT  1800
GGTCCCTGCC CTGCTAAACT CAGGGTAGCT GCATTCCGCT GGCCTTCCCC ATGTTCCAGG  1860
CTTCAGTCCC TTCTCTGCAC CTGTCCTTTG TGAAGTGACC AGAGGATTTC TGATCCTGTC  1920
TCTGTCGCTC TGAAGGGTCA GGAGTTCCTC CTGCCTGGAC AAAGCCATCC TGACGCACAT  1980
AAATAAAACA AACATCAAAC TCTATTCAAC CCCCTGGAAC CCGTGTGTGT TACTTACAGG  2040
GCAAAAGAAT GGAGCAGGGG ATGGGTTGTG GGGGGGGGGG GTGGCATCTG GGTTGTCTAC  2100
AGTTGTGCAT TAAGTTGTAA TTAAGATGTG CATTTCTCCA AATAAGGGAA AATTATTCTG  2160
GATTATTTGA GTGAAGCTGA AAGGTGATCA TCTAGA                            2196
```

FIG.4

FIG.5A
FIG.5B
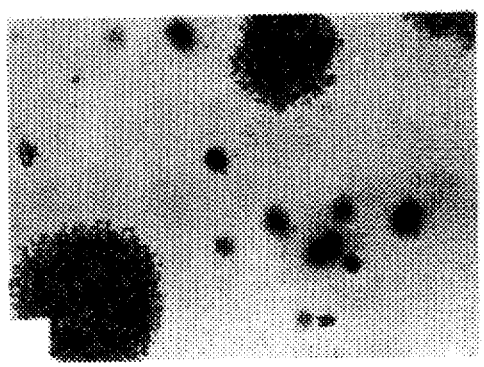
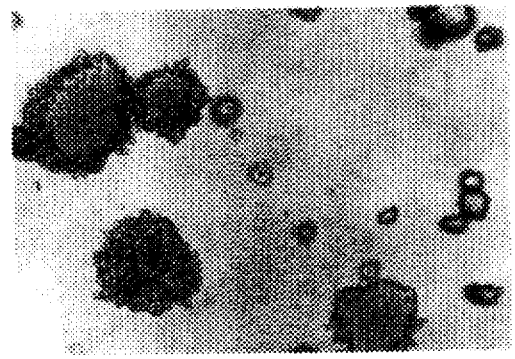
FIG.5C
FIG.5D
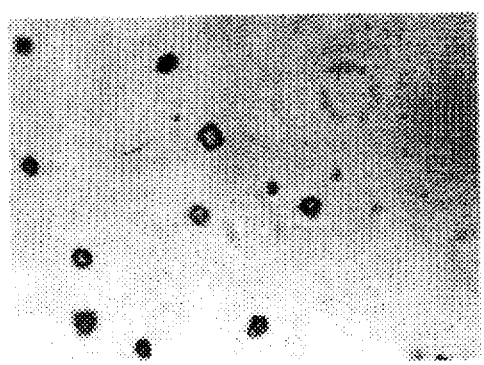
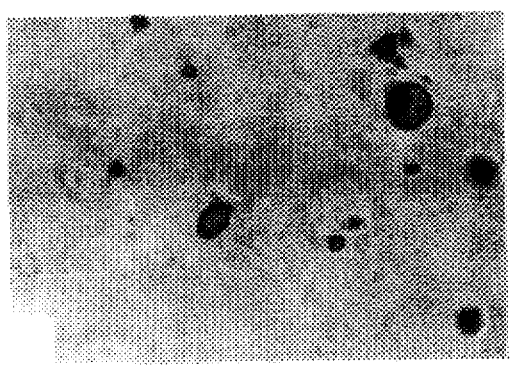
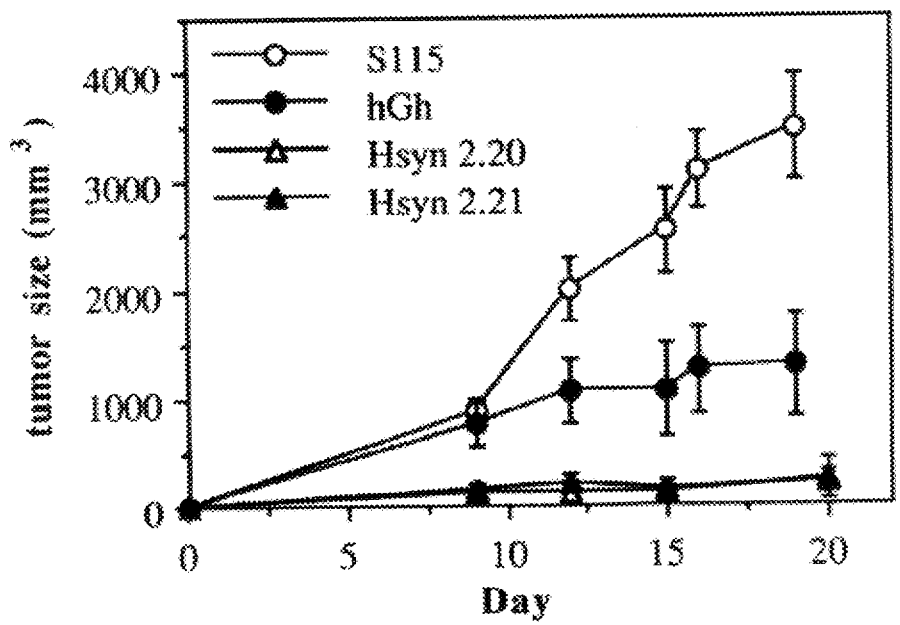
FIG.6

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 26700 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: join(4378..4443, 22026..22106, 23001..23483,
            23905..24039, 24251..24418)

( x i ) SEQUENCE DESCRIPTION: SEQ ID NO: 1:

```
TCTAGATATT  CAAACTCACC  AGATGGAGTG  ATGTCCACCC  CTATTGGTGG  GAGTGACTAG      60
TCTTTCCTCT  GTCTTCTGAC  TCAGATGCTT  AGCTAGCTCT  TTAGGACCCA  CCCTCACACC     120
TGCAAATAAT  ACTTTATTTG  CTCTCTTAGT  ACCTTTAACC  CAGTGGAGTT  GACATGAGAA     180
ATTAACTACC  ATAATTTATA  ATATTTCATT  TCATAAATGA  AAAGTAAAAT  AAATTAAAAA     240
ATAGAAAGGT  TTGAGCATGA  TGGCCCAGTG  GTAAAGGCCA  GTGGCTCCAA  CGCAAGTCCT     300
GACAAATGGT  AACGGGCCTG  TTCTTCAGGC  TTGAGGGAAG  TTTATTGATT  GAGGCTAAAA     360
GCAACCCAAA  GGCTCCACTT  GCCTAGTGTG  AAGCCCTGGA  TGTGCTCTCC  CACACTGCAT     420
GTCCACCTGT  GGTGTCAGCA  CCTGGGAAGC  TGAGGATGAT  GGGGAGTCCA  AGGTCATTAG     480
CTACATAGTA  TAGGCTAGCT  GGGGTACATG  GGTCACAAAA  AAGAAAAAAA  AATAAGCACA     540
TTGTAATCCC  AGCACTTGAC  AGACCAATGG  GGGGGGGATT  GCTGTGAGTT  TAAGACAGCC     600
TGGCCTACAA  AGAAAAACCC  TACCCAAACC  CAAGAAAAAT  GAAACCAGTA  ATATAAATAG     660
CTATTTTCAT  TTTAAATGCT  CTAAAGACAC  AGCGTTAACA  CAAAAGCTCT  CGTCTGTGGT     720
TCCTATTCCC  TCCTTCTCCC  CCAGGTCTTC  TTTAATGTAT  ACTTTTTGTT  TGCTTATTTG     780
CTTGTTTTGG  ATTTTGGCTT  TTAAAGACAG  GGTCTCACTA  TGTAGCTCCA  ACTATTTGGG     840
AACTCACTAT  GTAGACCAGG  CTAGCCAGGG  ACTTATAGAG  ATCTACCTAC  CACTGCCTCC     900
CAAGTGCTGA  GACTAAAGGC  ATGTGACACT  TGCTTGGTT   ATTACAAACA  TTTTAAAAGA     960
ACATTTTGAA  CATTAATAGA  TGTATGTATA  TATATCACTC  TATGTAGTAT  ATATGTTAGA    1020
CATTTTTCAC  TTGAGATACA  TATTTACTCT  CAAAATAAGT  TTTTGTTTT   TTTTCTTCT     1080
TTTTAAATTT  ATTTTATTTT  TTTTTATTT   ATTTATTAT   TATATGTAAG  TACACTGTAG    1140
CTGTCTTCAG  ACANACCAGA  AGAGGGAGTC  AGATCTTGTT  ACGGATGGTT  GTGAGCACCA    1200
TGTGGTTGCT  GGGATTCGAA  CTCTGGACCT  TCCGAAGAGC  AGTCGGGTGC  TCTTACCCAC    1260
TGAGCCATCT  CACCAGCCCC  TTAAATTTAT  TTTTATCTTA  TGTCCATTGG  TGTTTGCCT     1320
GCATGTATGT  GTAAAAGTGT  CAGAAACTGA  AGTTACAGAC  TGTTGTGAGC  TACCATTGTT    1380
GTGGGTGCTG  GGACTTGAAC  CTGGGTCCTC  TGGAAGAGCA  GTCATTATTC  TTAACCACTG    1440
AGCCATCTCT  CTAGCCCTCG  TTTTTTAGTT  TTTTTTTTG   TTTGTTTTG   TTTTTGTTT     1500
TTTTAAGATT  TTCTTATTTA  TTATATGTAA  GTACACTGTA  GCTGTCTTCA  GACACTCCAG    1560
```

-continued

```
AAGAGGGCGC CAGATCTCGT TATGGATGGT TGTGAGCACC ATGTGGTTGC TGGGAATTGA    1620
ACTCCAGACC TTTGGAAGAG CAGTCAGTGC TCTTAACTGC TGAGCCATCT CTCCAGCCCC    1680
GTTTTTTAGG TTTTTGAAGA CAGGGTTTCC TGTGTAGCTC TAGCTGTCCA GGAACTAGCT    1740
CTGTAGACCA GGTTGGCCTC AAATTTAGAG ATTTGCCTGT CTCTCTGCCT CTCGAGAGCT    1800
GGGATTAAAA GTGTGCAGCC CAACAATCTA CTCAAAGTAG GTTTGAAAA AGCTTTCCAT     1860
ATTAGGAGTT AACTAGCTTC ATTTCAGAAA TACTGCATGG AATTCAAATG TGGGACCATT    1920
CATAGCTACT TTGGTTTTCC TTCAGTGACA GGCATTGGC ATGCCTATTA GGGAAGTCAA     1980
ATGGCCTGGA GAAGTCATCC TGGGTGAGAG GGCTAATGCA TTTTCAGCTT GACAGACACT    2040
GTCAACCTAT GCAGACAGTC TGCTCCAGCT CAGATGTCAA TTGCATGCAG ACCTGCAGTC    2100
AGACGCTAAG CTCCCTACCT ACTCTCCATC AGCTTAGATG TAAGGGGTGC TGGAACAAAG    2160
GCTCTCTCTC TCTCTCTCTC TCTCTCTCTC TCTCTCTCTT TCTTAGAATT AGTATTCTAT    2220
TTTATTTTAT GTAAATTGGT ACTTCACTTA CATGTATGTC CGTGTGAGGA TGTTGTATCC    2280
TCTGGTACTG GAGTTATAGA CAGCTGTAAG TCGCCATACA GGTGCTGGGA ATTGAACCCT    2340
GATCCTCTGG AAGAATAGTC AGTGCTCTTA ACCCCTGAGC CATCTCTCCA ACCTCTTGCA    2400
TATTGAGGAC AGGGAGGAAT CACAAGCCAT GTAGGGTGCC TGGGCTCTGA GGTCAACAGG    2460
ACCATAGCCT CCTTTCTTTA TGTGCCTTTC TTGGGGTCTC CCTATAGGAG TCGTCTTCGT    2520
TGCCTCTTTA CTGTCTCATT GATCTGGGCT AAACTTATGC AGTTGGAAGG AAAGATCAAG    2580
CTGGTCATGT TTAAAACATG AAACAGCCTC ATCAGTTCCC TTCCTGTTCC CGTCTCCCCC    2640
CCCCCTCCCG CCCCCATTTT GAGAGGACAG GAAGGTAAAA TACCAAAGTG TCCTATTTTC    2700
CTCCAAATAT CAGGCTCAAA GGACTGAAGA GCTGACTTCA GATCCCAAAG CCACTGTGTT    2760
AGGAGGCACC TGCTTTTTAG GTCCTAAGCC TTCCTGAGCC TTGCTATTGG GTATTCTTTA    2820
CCAAGACCCT CAAGGATCTA GGCAAGAACT GGGCAGGATC TGTATGTAGC CCATAGTTAG    2880
ACCTAGGGCA GCTGAGACGC CAAAAGGGAG AGTTTCCTGA GGACAAAAGT GTTCAAACAC    2940
AACTGGGTGC TGGTTGTTGG GCTACTCGTG GAGGTGTGGT GTGTGTAAAG GAGGCTGTTG    3000
AATTCCCAGA AGGCTGGTTC CACAGTGTAG AGTCTACACT GGGGACTTCC CGAGACGCTG    3060
AGCCTCAGAT CTAGCTTCTC AGTCCAGGCC AGCTGATGTG GGGCTGAGGA ACAAGGATGG    3120
ATGCCATCTA TGGCCCTGCC TTGCAGGTGC AAAGGGCCTT TGGCACCATC TACAGATTGA    3180
GGGCAAGACA GGGCTGGTTC TTCCTCCTTG CTCTCGCTGC TATCTGCCTC GCCTGTAGGC    3240
TCTCTGGGCT CCTTTTTGGA CTGACACGTC TGAAGGAGCT TGGAAACTGT GAGGTCCAGG    3300
CCCCATAGAG AATCATGAAG GAACAGGAAT TCAACTGGAG CTCCGCAGCT GGTTAGGCCT    3360
GCGGTCACCT GGAAACAAAG AGGCCATTTA TTTTTTCCTT TGGTCTTGGA CAAGGAAGAG    3420
AAGGGGCTTT CTATAAATAG AAAGACAGCA AAAAGAAAA TAATAATAAT AATAATAATA     3480
ATAATAATAA TAATAAAAAC AATAACAAAG CCAGCTCTTC CAGACAGTGC TCATGTCTTT    3540
AAAGGTCTTT AAAGGTCTGG AGTTCCCAGC AATTAAGTAA AGGACCAAGA CCTCAGGGGT    3600
CCCCTATCCT CAGCCCGTGG GGAGGTGGGA ACCATACATC GATCCCTCGG TTTATATATA    3660
GCCTCATCGC TGTGGGGCTC CGAGGTTGCC CCCAAAATCT TGCTCACCTG GAGGACCCCT    3720
GGGTGTCCTC GCCCAGAGGG CGCTGCAGCC TCGCACGTAG AGAACTAACA TCGCCCTTCT    3780
CCAGGGCAGT GCCTCCGGAC TCCGGACCAG GACATAGTAG CGAGTGCACC TGGGTCTCCG    3840
TCAGCTACGC ATCAAGGAAG GTGCGACGCG GGAATTACAG ATTGCCGGCA CTCACCAGTG    3900
CTCAGGGGAG GAAGGTGGGA CTCAGACCTG CAAGAGCTGA AGAGTGGGGT GGGCTTCGAT    3960
```

```
CCTAGGAGGC  GTGGAAGGGG  GTGTGGCTGG  ATCCCTGGGG  GGTGGGGCGC  TCCAAGGGGC      4020

GGGGCAACCC  AGGGGGCGGG  GCCCGAGGGG  TGGAGATTGG  GACTACCCAG  GCCCGCGGAG      4080

CTGGGGGTGG  GCGGCTAGTT  TTGCAACTGC  AGAGCCTTTG  GGTTTATTAT  AAGGCGGAGC      4140

TCCGCGGGAG  AGGTGCGGGC  CAGAGGAGAC  AGAGCCTAAC  GCAGAGGAAG  GGACCTGGCA      4200

GTCGGGAGCT  GACTCCAGCC  GGCGAAACCT  ACAGCCCTCG  CTCGAGAGAG  CAGCGAGCTG      4260

GGCAGGAGCC  TGGGACAGCA  AAGCGCAGAG  CAATCAGCAG  AGCCGGCCCG  GAGCTCCGTG      4320

CAACCGGCAA  CTCGGATCCA  CGAAGCCCAC  CGAGCTCCCG  CCGCCGGTCT  GGGCAGC         4377
```

```
ATG AGA CGC GCG GCG CTC TGG CTC TGG CTC TGC GCG CTG GCG CTG CGC              4425
Met Arg Arg Ala Ala Leu Trp Leu Trp Leu Cys Ala Leu Ala Leu Arg
 1           5                  10                  15

CTG CAG CCT GCC CTC CCG GTGAGTGTGG CCCGGGGCAG GGCTGGGAGG                    4473
Leu Gln Pro Ala Leu Pro
             20
```

```
CGGCGGGAAG  CCGGGACTCG  CCACTCGCCG  ATGCCATGCA  GGCGGCAGCA  CGTGGAGGGG      4533

GAGGGGAGCG  GGGACTTCTT  CCCGCGCTGC  CTGGCGGATC  CTGGGATGGT  GAGCCCTTTA      4593

ATGAGGACTC  CTGTCCCAAT  TCCTCTACGG  TCCGTGGATG  CCAGGAGGCT  ATCCCAGCTC      4653

GTGGTCCGGG  CGTCCTGCAG  AGTGGAACCT  CCATTGGTTC  CCCGCTCCCA  ATTAAGTAAA      4713

ACGACTCCAC  AGGGGTCTGA  GTCGCCGGCC  TTAGGCGCTC  CGCCGGCCTT  AGGCGCCGCT      4773

TGGAGTTGCT  CTCTCCCGTT  GCTGTCTTGC  TGGCCATCTC  AGCGGCCTGG  CCTCCGCCAG      4833

TGTCCCGGAG  GATGCAGTGG  CCATGGCCAA  ACGCCTTTTC  CATAGACCCT  AATTCAAACC      4893

AGACTGCAGG  CTGCACCCCC  AGCGCCGCGG  AGTCCGGGCG  CTCGGCCCTT  TGCACCGGGG      4953

CAAGTTTGGG  CACAGCAGAG  CCGGCGCGGG  AACAGGGGGA  AGCTGACGTT  CGGGGTGGCG      5013

GGAGGGACGG  GATTAAGGCT  GTTTGTGGGA  CACAAGAGGG  TGGCTCAGGG  ACTTCGGTTT      5073

TTCTCTGGCT  GCCCCAGGTG  AGCCGGGCCG  AGCTGGCAGC  GGGAGGTTCC  GGGAAGTTGG      5133

CTTCAGAACG  CTGAAGACCC  TAAGAACCCA  ACTTTGGGGT  CGCTGAAGTT  GTGCTGCCCC      5193

CGGAGGGCCT  CCTCCGCATG  GCCCGCGCGG  GGGACCCTCC  CCGCGAGTGG  ACCCCGGTAC      5253

GGCTCTTCCC  CTCCCCCGAC  TCGGCTTTGT  GCTGAAGCCG  CGCGTAGGGA  AGGCGGGTCC      5313

CTTGGCCCGC  CCAGTAGGGC  CGCGGGGAAA  GAGGGACGAA  CGTGGAGCTG  GCGACTGGTG      5373

GGGGAAGCTT  CTGGGTAGGA  TGCAGCCATC  CACCTTTGGT  GGGGTCGGTC  TCTCTAATCA      5433

GCGGCTTGGC  GACAAAGAGC  TTGGTCGAGG  GTACCCAGA   AAGTGCTCTC  CCGCCCCAAG      5493

CCGCCGTCGC  TAGCCCGCCT  TCCCAACGGG  CGCTTTGTTC  TCGGCCCCTG  TAACCCTTCC      5553

CTGGGAACCG  CCCCGCAGCG  CTGGTCCTTG  ACGTGGGCCG  GGTCCTGGGT  CGCCGCCAGT      5613

GTCAGCGCTG  CCCTCCGGTG  TCCACGCCCC  TAGCCCCGC   ACCGCTGTG   AAGTCCCGGG      5673

TGTCCTTTCC  ACTGGCGCTT  TGCCCAACCC  CTGGAAGGCA  GAGGCGAGGT  GCGGAGCCTC      5733

AGGCTTTATC  CTCCCGGAAG  TGGCAGTCTC  CCACCGCCAC  ATCTGGTCTG  CTTAACTTCG      5793

ATAGTCCTGG  CAAAGGCAGA  CACGTGCACA  GGGAAGGAGA  GTTGAGCGCT  GGTAGATACC      5853

AAGGTCGTGT  ACAAATAAAG  TGGCACACGA  CACGTCCCCA  GTCACTGTTA  ATGCATTGCC      5913

TTCGCTCCTT  CCCAGGTGGC  TGGTGCTCTC  CATCACTCTG  GAGCCCAAGA  GAGGGCCTCC      5973

ATAATTGTAT  TGCCCATGAG  TTGGGGTTGT  GTGGGGCGC   CAAATCAGGG  TTCTCTGGGA      6033

GGGCTATGAA  TTCCGAACTG  AGTCTCCTGT  GCACTCCTGG  CTTTAAGGTT  CAAGAAATTG      6093

TTTGAGGGTT  GTGGTTTTTG  TGGGACTCAG  ATTATGCCTG  GAATCATAGT  TACCACTGTG      6153

GAGAAGAAAG  TGGAGCTACT  TAGCATGCCT  CCCCGGCCCG  CCTGGCATTA  CCTCCGGCTC      6213
```

```
TGTTCTCTAG GCCCAACGTG AGGCCTCACT GGGGCAGTAC AGATGCAGTA CTGAATTTCT    6273
TTCCAGCCAG GATCTGGAGA GGTGGTGTTC TCTTCCCTGG TGTCTTTAGA GAGGCAGATA    6333
TTCCTGTGAC CTAAGCCCCT CAAGCACCCA TTAATAATGC TGAGTAGACA ACTAGAGGTG    6393
GCGTTTTCCG GAACTTCCTG TGTGCTGGCC TGGGAGGTTG AACCCTCTAG GAAACAGGTC    6453
TAGGAAGTAG AATTATCTCA ATGGAAGGCT TCCTGGAGGA AGAAGATGAG CTGAGCCCCC    6513
AGGTCACTGT CTGAGCTTTA GGATCAGACT CCCACTTGGA GGCAAGAGTG TTCGTTTTAC    6573
TTTTTTTTTT TAAGTTTAGT TTATTTCTC TCTAACAGAA AACAAACAAA CAAACAAAAA    6633
AAAACCCCAC ATTGTTTAAA AGTGGGTGCA TAAGAGTGAG GACATATTCA GAGCTTCCCC    6693
TTTTCCTGAA AAATGAAGGC AGCTGGGATT TACTTAAAAT GAGAGCACAT ATCACAATTG    6753
CCAGAGAGCT GGTCCCTTTC TCAGGGCTCC CTAAGCTCCT GTGGGAAGCA GGTCAGACAG    6813
CCCTGGGGAC CAGAGAGATA GGGAGTGCTT TTGGGTGCCT GCCTTTGAAT GGGGAAGGGG    6873
GGGGAGCTG CTGGGATCAG AGGCTGCTAG CAACTACTCC CCAGAGACTG AAGCAGGTTT    6933
GTCCCTCAGT GTCCTGTGGT CTTCTGTTTC TCCTATATAG AATAGGAGAA ATGGTTATTT    6993
GCTCTGGAAT AGTGACTTGC TATTTGTTCC CTTTCTTTCC TCTCCCTTAC TGTAATCATT    7053
TGGACTAGTA GAGACACTTT CCCCAGGTCT GGCAGAATGG GAGGGAGTGG GGGAGGCCTG    7113
TGCTTGCATG ATGTCACTGC TGGCTTCAGC TCTCCAGGGA GGGTGGAGTT GGTTGTAACC    7173
TACCTGTGGC TCTTGATGGG CCACAATAAA ACCTCATTAA CACACATTGG TAGGGAGAAG    7233
GGACTGGAAA GAATGATGGG AAAGATTGAT GTTTTCCTT TTTTTTTTT TTTTTTTTG    7293
GCAGTACTTT CTAGATCTCC CCTCCCCCTT GCTGCAGCAA AATTTTGGAT TCCTGAAGTC    7353
CTTTGAGAAT GTATAATGGT AGCCAGACTT TTTTTTTTC AGTCAGCTCA AAATTGCCTC    7413
CTTATAAAGT ATCCTTGGTT GTTTTTGTT GTTGTTGTTG TTGTTGTTTT GTTTGTTTT    7473
AAGACAAGGT TTCTCTGTAT AGTCCTGGCT GCCCTGGAAC TCAATATGTA GACCAGGCTG    7533
GCCTCAAACT CAAAGAAATC CACCTACTTC TAACTTTCAG TGCTGGGCCT AAAGGTGTAG    7593
GCCACCAAAA GTGCTCAACT TTTACAAAGC AGTCTTACTT TGAGCAGGAT TCTGAAACCC    7653
TTATTTCCTT TCTGTTATCT TCAACAATAC ACTGCTAGGT GTATTAGTC CCTCATGATG    7713
CTGGGCCTCC TCAAGTGGCG CCAGGTCAAG CAGTCTCCTG GTTTTGGTG GCTCTGAAGA    7773
AGACTGTGTC CCAGTGACTG GCAGTTTGAA TTCGGAGCTT CTCTTTTCCT TCTCAGTCTT    7833
TGGCAGGCAG AGTGACACTG GTGTGCCCAA GCCTGGAGCT TCTCTGTTTA ATTCTAGTTT    7893
ATTTTCTTTA TCAGACTGAA AAACAAATCA GGTTGGTTAT AATTCTTATA AACACGAAGG    7953
TCTCACCTTT GCGTACGTCT CCGGCTGTGT GGGTCTGATG TCCCTCGGGA ATCTCTGTTG    8013
AGGCTGCTGC AGTGTGTGTG CGTGTAGAAA GGGCAAGGTA GAATGGACAG AAGCGTGCTG    8073
CCCACCCCAC TGTCCTGTTC CTAAATGATG AAGCACTGGC CCGGTGAAGA GCCTAGAGAA    8133
CTCCCTCGGT GGGAGATGCA CACAATGCCA GGAAGCACAC AGGAGCTTGA GTTCCAGCTT    8193
GGCAGTGTCT TCTCTTTGGT GACTTTATCA GCTCCAGCTG CCCTGGACTA ACAAACAAGG    8253
CTAGCTCACT CTCAGTATTG ATAATCGAAG GTCCTTGGTT CTGTTTGAGA CTGATCCTCA    8313
CTCGGTAGCC TTGAACTCTT AGCAATTCTC CTGTCTCAAC TTTCAAAGAG CTGAAATTAC    8373
AGACTCGAGC CACCATATGC GACTGAAACC TTGTTCCTAA TCCTTGACTG TGAACGACTC    8433
TTGGGTTTGG TTCTTTCTCC ATTTCTTTAG TGTATGTTTT AGTTCGCGTC CTACATAATC    8493
TATTGCCCAT ACTTAGAAAC AACAGGTTAG AGACAGCATT GGGTCCAGCA GAGCCTCACA    8553
CTGAAGCTCA GTCCTGCCAC TGATTTACCG TGTCAGCTCA AGTGACTCAC TTCCAACTCC    8613
```

-continued

```
TCTGCTCCCC ATCTGTAGAG TAGACATCAC CATACCTGCT CTTTCTGCCC ACATTCTGTC    8673
ATTAACATGT TCATTTCATA ACGATGGTGC AAAAGTGCTT TGTAAGTAAA GTGCTGGGA     8733
AATGTTAGCT GTCGATAATG GTTAGGGTTA ACTTTTTATT GAGTGCCTGT TGTGTGTGGG    8793
GTTGGGTGGG GTTTTTTAG AGGCTTGGTA GTTTCTTAC TTCTTTCCTA CTTAGCTTTT      8853
CTTCCTAAGC CTTTATGGTA TGTATCATTG CCTGATTGTT TGAGTGTGTG CACTGAGGCA    8913
CGCCTGTGCA TGTTTGAGAG TATGCTTGTG CGTGCTCTCG TGCTCACATA TGTATGGTGT    8973
GAATACACTG TAGAGTGCAG GCCGGCACAC TGGGGCTGGC TGAATCCTGT GAGCCCTGCC    9033
TGGAGTTTGC AGATCTTCCT TGGACACTCC TGCTTGTGAG CATTTGTGT GGAGTGACTG     9093
TTTAGCTGGC TGTAGCCTAC ATTGTGCCTT TGGGTAAACC CTGAGTATTG GGAAACACCC    9153
TGGGCTGTGG CTGTGTGTGC CCGACGGTTG CTTGGGTACA GCTAAGAACT CTTCATAGAA    9213
AGTTGAGCTC ACATGCTATT AGTATTAACT GAGTGCTAAG GAACCTGTCT TGGGTGGTAC    9273
CTGCTTGCCC TCTCATGCAG TTTATCTTGA GCTTGGCGAA CACACTTACA GATTTAGTAG    9333
AGCTTTTGTC AGCCCTGGGA GGTGGGTTTC GTGGCCACAA GTGGGTAGCT TGGAATCCAA    9393
GACTCCTGGC TTCTAGGTTG CATTCTCCTG TGGTTCTTTC CAAGGGAATG CTAGGGGAAC    9453
ATTTGGACA TTAGATTATT TCTAGTCCCA AAGCACACAG AACATACTGT TTCCTAATTG     9513
CCTTTTTTTT GTTTCCTCT CAATCTGGTT TTGAAGTGTT GGGTTTGAAA ATTGCCCCCT     9573
GAGAGCCTGC CCTAGTGTGT GCAGAGGGAA GATAGTGGAA CAGGAAGTCT GTAGAAAGTA    9633
TCTTCCTTTC CAGGACCTTG TGCCCCGGAG CAGAGTCAGC ATGGTGTCAT ATCGCTTTTG    9693
GCTATTCCAG AAGAGATGAG GTTTAGGTG AGAATGAACC TTTTAGAACC TTCTAGAACC     9753
TTCTGTTGAG TATGACAGGA ATGCCCTGAA TAGGGTCCGA AGTGCATGGC CACTTGTTTG    9813
TCTTTTCCAT AAGCAAGCAG CTTCAGGTAC AGACAATAAG ACTAGGTTCT TGGAGTGAGA    9873
CCCTGCACTT GGTGCCATTT CAGCTCCAGA TGGACACTGG AGGTCCCTAC ACAGCAGGCT    9933
CTGGGATGGC TGGCTTTGCT ATGTACTGTT GCCTGCTCTA CAAGAGCTTC CCAGGTTACT    9993
AGCCTTTGTC GACGCTGGGC TCGCTGGCCA GGCTTGGGCA TTGGAGAAGG GACAACTTGC   10053
CACCTGGCAT AGGCTGTGTG TTTGGAGAGT CAGGAGGTCT GGTGAAGCCC GCAAGTGGAG   10113
GCAAGTTTAG TGGGACTTGA GGAGAGCTCA GTAGGAAATC TCTGGGCTAG TGACAGGCAG   10173
GTGTGGTGGT GGTGGCGAGG TGGCGGGTCT AGATCTCCTT TTAGAGATTT GCCTAGGGAT   10233
CGTCCCTGCT GACTCTGGAA CTCAGAGGCC TCCAGAGGTG TCTCCTCTGG GAGCCTCTCA   10293
AGGGTCTCCC ATCTCCTACT GTTTATGGCT TTGTGGGCTA CCTAATTACA TAGAGAAGAT   10353
ATGTTCCTCT GCCTCCAGCC CTGGAAAGTT CTGCCCAGTG ACTCACCTGA GCCTGCAGCC   10413
ATGTGTGTAC ACAGGCGCTC TCAGGGCTT CTGTCCTGCT GGCTTCAGCC TTTCTAGCCC    10473
CTGGTGTTCT CGGCAGTGGT AGCATCTGGG AAACCGGGTC ACCTCTTATT TGCAGCTCCC   10533
TCCCTTTCTT GGTGTCTTCC CCCTTTTTAA CTACTGGTCT GATGGCCTTA GACTCATGCT   10593
GAAATTCTCC TTTCTTTTGT CCTAGCCTTG TCTCTGACTT CTTGTGATCC TCTGGGCCTG   10653
TGAAATCCGC TCAGGGGCCT CCATTTCTAA CAGTCACACA CTGGTGGAGA GACCGAGTCC   10713
TGGGATGGTG AAGCTAACCC TGCTGGGCTT CTCAAGCTTC ATTTGGTTTC TCTTTATTCC   10773
TTCTGGAGGT ACTGCCTGCC CCAGGGGAGT CTCAGACTAG ACCACTCTGG AGTTGGAGGT   10833
GGGGCAGGTT TTCAGATCAG TGCCCTTGGC ATTCGTTGTG GGAATGGGGT GGATGGGCC    10893
TCTGGGCAAG GTCAGGCTGG GGGTGGAGGC CAGGTGATGT TCTCCGCACC CACACCCAGG   10953
CAGCCTGGCA CCCTCCCCAA GGTCCGCTCA TCAGCAGGAA TGAAAGCAGT GCCGGGCAGG   11013
```

```
TTGGGGCAGT GGGCAGGTGG GCGTGTTTAT CGCTGTGCTC ATCAGCTGAG TCACGATGCC    11073
AGGCCCCACA AGTCCTCCCT GGAGGCTCAC CCCACCCACC TTGACCCACC AGCACCCACT    11133
AGCAGGAGGT AGGGCAGGGC AGTGAGACAA GACCAGCCTG GGGGTCTGAG AGGCAAAGGG    11193
GAGTTGTTCA TGACCTGGCT GTGCATGGGG ACTTGTGGGT GTCTCAGATA TCTCTGCTGT    11253
CCAGGAGGAA GCTGTCTTAA GTGCCAACCT GCCTAGAGCC CCTGCTGGGT GCAGGAAATG    11313
CACAAGGGAG AGTGCCCATC CATGGAATAG GCCCATGGAG CTAGACCAGT GACAGTGACA    11373
GTGAAGTCAG CCCCCACCTG TGTCTTCCGA GCCAGCTGGA GGGTTTTTAT CTCAGATTCT    11433
GCGAAACCAT AGAATCTAGT CAGGAGCCTA GACTGCAAAG CAGGCTTCGT TGATGCTTTA    11493
ACTTGCAGGC TTCCTGGGTA TGAGGGATAC TTAGAAAGGT CCCGCAGGTA GGGAGGGCAT    11553
CAGGAAGTAG AAGAGGGCCA GGCACTTCTA TCTCCTGCAT TGCCCCCTTC TCCATCTCC     11613
AAGGATGGTA AAAAGAACCC TTCCAGTACA CTGACAGAGA GGAAAACCCT TCATCTCACC    11673
CCATTTGGAT CTGTCGTATC AGCATGTGCT GGCCCTGCTT CCATACCAGA GGTGGCTAGA    11733
GATGTTCCCT GGGAATTCAC TGGTTGGGGA CTTGAGTGTA TCAGAGGGGC ACAAAGTAAC    11793
ATTAACTCTG GTATCCTCTG CAGCAAATCG GAGATCCCCT CTCCTAGGCG AGTTCTCAGT    11853
GGATATGGAG GTCAGGTTTG GGCTTGTAGG GCCCCAGCAA GAGTCGTTGA TGTCACTCCA    11913
GCTTCTCCCG AGGAAGATGA GGGTGCTGTG TTGGGATCAC ATCTCTCCCT GAATGGCATG    11973
TTGGGGAGGG ATGGAGCCCT TGCTTCTGAC CCCTAAGCTT GGTCTTTAGG TGGCCACAGT    12033
CTCTGGGTTC TGTCCTACCT CCCTGCCCTT GTGTGCTTCA AAGGCATGCT AAAGGGACTC    12093
TCGGCCATTC CGAATGGCAC AGTGTTCCTT CTGTTCTCCC ACCCCAGAA GGAGGCAGGC    12153
CTGGATTGTA GATTCCTAGA AGTAAGTGGC CCTGAGCATG CTGTTGATGA ACCTGGAACC    12213
AGGCAGGCTG GGCATCCTAG GACCTGTCTT TCCATAGAAG TCTGAATCAG TCTACCTTTG    12273
GGACTGAGTA AGGGCTCCT CACATATCAG CTGGCTAGTC CATCTTGGCT GATCTAAACC    12333
ACATTAGGCT GAAGAGAAGC ATGGTGTACA GTCTGGTCCA CCCGAACCAC ATACTGGCTT    12393
TATCAGTTCT CGTATAATTT TGCAGGTAAC TTTTTAGCTC TAAGCCTGTC TCCTCATCTG    12453
TGAAATCGGG TCCCTCATAT CCTGCCTAGA AGGGCTTTTG AAAAGATTAA TGAAGTAGTA    12513
TGCCGAGTGG TTGGGGTTCT CTCCTTGACT GGAGCAAGTC TCTAGGAGTA CTAAGGATAG    12573
CCTGCTGTGT GCAGCACCCC CAGGGACTGT GCCTGAGTAG GAGGGTACAG AGTCTTCATG    12633
TGAATGGCCC TTCTGGTCTT GCCCCGAAGT TAGTGTTGAT GTCATAGAGT CTACAAACAT    12693
GCCTTTTGTC CTTCCTCAGA AGTCCAAGCC TTTCCTGGCA GACCAGACAT TCATCTCCAC    12753
TGAGCCTCTA TGTGAGACTG GCTCCTGGCC TGAGCTGTGT GGGCTGAGCT GGCGAATGGG    12813
AAAACTAGAC ACCTGGGCAC CTGGGTGGGG GCTCGGGACA GCAGTGTTTC AGTTGTAGGC    12873
ACTGTGCCCC TGCCTGGAGC TTCTGACTGA AGGTTACCCT GAGAGGAAGC AGGTTCCCTA    12933
TAGACACTAA CATAGCTGGG TCAGAGTGCA AGGTGGGTGT GCCCTGCCC TGACCCATTC     12993
AGTGCAAAGG CTGCTCTTCT GGGAGTGAGA GCTCTGACAG GACTGTGATG GCCGAGGGGT    13053
CTCAGAGCAA ACCTGCCTGG CCTCTCCCCA CTCTGATGGA TATGTGCTCT TAAACAAGTG    13113
ACTGTCCACT TTGCCTCAAT TTCAACATCT GTAAGATAGA TAGGGCGTTA TGGTCTGAAA    13173
ATGGTTTTAA AGATTAGTTA GCTAATACAG GGAAAGTGCT CTGACAGGTA CCTGGCACCT    13233
TACTCAACAA GTGGCTGGAG TGCCTGATTT CCTAAGGTCT CGACCTGTCC CTATGCTTCA    13293
AGTGCCCCTA CAGCCTTGGT CAGGCCCTTA GGTTCTCCCA CCCACCGCTG GCCCCAGGAC    13353
CTAGACTGCT GGACCCTGAC CCCATTTTTC CTTTAAGCCA CCTCTGCGTC AACTCTAAAA    13413
```

```
GGCGGTGGAG TTGTTTATCT AGGCTGTGAG GTGTCAGAGA AAGGACCTGG GCCGCTTTGT    13473
TCCTGTGTGG GCTGGGGCCA CTCCAGGAAC TGAGAAACCC ACCCACCTTT TCAAAAACAG    13533
CCTCTTCTCA GAGTCTGGCA CCTCAGCTAG CCACCATGCT GTGGGACCAC TCCCAGCATG    13593
CTCTGCCTTT GGTTTGTTTC CCAGGGGCCT CAGTGCCTTT TAAAGATGCA CAGGCATCTT    13653
TAGTTCAAGG GGAAAGAGGA AATGAAGTGT ATTTGCTGGT GGTGGTATTC CTGTCACTTG    13713
CATTCTCACA GAGGCTAAAG AAATTTGCTC TTTGTATCTT CTAGTCTCTT CTTTATGATC    13773
TTTTCCCATC TGTTGTATCC CAACTGCAGG GCCCCAGTTC TAGAATTAGC CCCTCCCCCA    13833
TAGGAAGCCG ACTTATGCTA TAATGTGAAT GACAAGTATC CTTTAGCCCT TCCCACAGGC    13893
ATTTTAATTT TCAAAAGGGC ATTGCACAAC CGCAGAGACA CTAAGAAGAG AGGTTTGGTG    13953
ATCAGAGTTA CAGCCCCAGC CTCCCAGCTG GTGGCCCGGC TGGTGCAGGT GTGTCGAAAG    14013
CAGTAGTTTC TGCTTCAGTG AAACTTGAGG ATCCTTTATT TAGCCAGTTC AGGGGCGGAA    14073
TGGCCATGCG AAGTCTATGT GTCACAGGTG TCAGGCCCCC ATATCCTGCT GAGTCTAGAA    14133
TCAGCTACGT AGCAGTTTTG GGGTATTGC CAGACTGGGA GTTACATCC CAGAAGCGAG     14193
AATGGTGGGG TTCCTATACT GCTCCAGACA GGATCTTTCC CCCAAGTTTG TCAGCCACCT    14253
CTCTTCAAGT CCCTTGGCTC TGACCAGCAA GACGTATCCA AAAGAAACTG AGGAGGCCCT    14313
TCACTTCTTT TTAGGATAGT GTGGGGCCAG CATGGTGGGG GTTGGGAATG GCTTTCTGTC    14373
TCTTCCATCA TCACAGGCTA CTTCCCAGAG ACACTTTGAT TCTGGGCATC TCCAGCAGTC    14433
ACCTGGCCCA CAATGCTTTG CTGCCCTTTG CTTCAGCCAC TGTATCTGGT TGTCCCTTGA    14493
AGGTGAGCCA GAGCTCCTAG GCAGAGAGCA TGTGCTATAC AAAGCCGTAG GCTGGGCCCT    14553
GGGAACCTTC TTGCTGTCAT CCTCCTGTCA AACCCTATG GTATGGTAGC CCACATAAGG    14613
CTTGTGCAAA AAACAGGCCA AAACATAAGT TATCTTTTCA CTCTATCGGG TCTTCTCATT    14673
TTCCCATGGT ACGTTCGGCT GGCCAGGCCC AAAAGATTTG AAGAGAGGTG GCTGGCAAGT    14733
CTAGGGGAAT AGGTCTATCT GGTTCCCTCC AGGAGCAGTG CCTAGTGAGA GGCTGGGCTG    14793
GGCAGGGCAG GGCCCCTTGC TCCACATTGC CTGAAGTCCC GCCCTGCCCG TCCTGGCTGG    14853
GATCTGGCAG GTCTTCCAGC TCCACACCCG GCTCTCAGCT GAGCCTGCTC AGAGACTAGT    14913
CCTGGCATGT GGGTTGCAGG GCTGGTTCCA GCTCCACCAG GAGGTATGGG CGTCTGGGTA    14973
CTCATGGGAC ATTGACCTGT AGTGGGTATG GAGAGTGGAG GAATGGTACA GGCAGGTGTG    15033
CTGGTGCTGA CGGACTTGAC TCCGGCATTG ACCTTGGCTT GCAGTCTGGT GTTAAACTAA    15093
CAGGGAATGC TGACAAAAAA GACAGTTATT AAAACCAAGA CAGGATACTG CTTTCCCACT    15153
CAGCCCATTC CCAAGAATCC CCAAGACGTA CAGGAAATGT GCAACAGCAG TGGGAATTGC    15213
TGAGTTGGGG GATGTGGGTG AGCTGTGTGC TCCCAGGGAA TTTTGGGAAA TTCCCCTCCG    15273
TTGAAATGCT GTCAGGGTCT GAGCCTTGGA GGTGTTTTG GGGTGCTGTG CTCCCCAGCT     15333
AAGCAGCTAA CAGTCCTCTT TACCTGCCTT GTCCTCACCT TGCCCCACCC TGGGTTGGGC    15393
CTCTCGTTCA CTCCCTGCTG GGTCACCAGT ACTTCAGTGC AGGTCTCAGC TTGATTCTTG    15453
GTGGAGAGAG AGAAAGTTGA TAAATCAGGG TGCCTGTCAG CCGGAAATTT GGGTGTGTCC    15513
TGAAGGCACC AATGGGGGCC CTCCCTTCTG GAGGTGGCTT TAGGAAGGGG TTTCTGGGTC    15573
TTGAGGCCTC CTTACAGTTT CTTAGCTCCA TGGGAGAGAA GTGAGGAGTT GGGTATCGTC    15633
ACCCCAGCAT GAATCTCTGG TCACCTCTCA GCATGCACTG TCCAGCCTGA TCTTTGAGTG    15693
CCATAAAAGA ACAGAATTAT CCTCTCAGAG CACTTCATTT CCCGCCAGCA CAGTGGGTAC    15753
AGAGACAAGC TGCCCAGACT CCCAGCGAGG GACTAGTTGA GCCCCAGCAT GGGACTAGTT    15813
```

```
GAGCTAGACC TGATACAGTC CCAGAGAGCC TCGTTGAGGA AGCTTTGGGA AAATTCACCC    15873
AGCATTTCAG CCAGGACTGG AGGAAAAGGT GATTATGGGA AAGAGAGCAG TCAAGACCCC    15933
AGGCTGTAGG ACACAGGATA CAAACTGAGA GCTACCGGAT AGGAGTAGGT TTTAGTCACA    15993
ATCTCTCCTG TCCGCCCTAC CCTCCAGGAG ACATTGCACC TTGTAGAACA GCTGCCCCGG    16053
AGTCCACCTT TGGGCCCCCC TGGGTAGCTC AGTAGTGTCA GCATCCTCTC ATTGACATCA    16113
GTCAGGTTAC ACAGTGGGGC AGCTAATGTG AAGGCGCTAG GCTGGGAAGC CAGCTACTTG    16173
GGAAAACTAG GTTGTTCCTG GTAGGCCCTA GCAGGAAGGC AGTTCCTCCT TTTCTTGGTG    16233
GCTTTAGGGG TCTTTGGAAG CTTTGAATGT TCCCTCAGCT CGTTGGTGAA GCAGGCCCTC    16293
CTGGTACTGT GGTGTTTGTC TTCGAAGAGT GAAGGCATTG GAAGTAAAGA CTGATGGGGC    16353
GCCTTCCCAG GATGCTTTGC TTCTTGCGCT GGCTTACAGA GCTCTCTTGC TACCTAGTGC    16413
CTTGACTTTG AACACCAGAT TCAGTCAGGG AACAGGAGTA GAGGTCTTGC CTTGCTGAGC    16473
CCCTGCGCAC TGCAGGAAAA GACTCCTCTG AGTGGAGCCT TTCCTCCTCA GGTGACTGCT    16533
TTCAAAGTAC AGCAGCCTCT GAGGGGGAAG TGTCATTTGA CATTGTGGTA GTTCTTGGGG    16593
TCCCTGGATA CAGATGTCAT GCCCAGATCA TAGGTCTGTT TGTACAGAGG GAGGCGAGTT    16653
CTGTAGCTCA GAGTCCTCAG TACCCCAGAG TTGTGGCTCT AGGGGTGAGA GGAGAAGACT    16713
ACAGCCCTTC AATCACAGGT CTGACCTGTG GGTAGGGTA  GATCTCTTGC ATACTATGAA    16773
CCTGTTTGAA ACCCCTGGGT ATTTGCTGTG GAATAGAGTC TTGGTTGGGT AAGAATGGTG    16833
GATGTTTATC TTGGTGTGAC TCTCGGGTGG GGGTGGGGGA TATGTCCCTG TCTTTCCCAA    16893
TGTAGTATGC TGAGTGGACA GAGACCGTGT GACTGAAGCC TGGGCTCCTG GAACAGGTGT    16953
GTGTTGGTGG GGGTGGGGC  GCAACTATCT GGGATCCAGA CTGCTTGGGA ATGGCTGTGA    17013
CCCAGCTCCT TTGATAACAG CAGCTCTTTG TCACTGGATG TTGTGACTAA TGGGACTTGT    17073
TGATTCAGTT ACTCGGCTCC CACCCACAGA CGCCGGGGCT TCTGTTGTGG CACCAGGCAG    17133
CTGCAGACGG CCCACAAGTT TGCCTCGCTT TCCCACTCCA CGAAGGTAAG TTCCCAGCAC    17193
TGCCCAAATT AGAGACTTGT GAGTGGTCCC CTCATACCCC ACTCCTGAG  GCTTCTCCTG    17253
GAAGGCCTGG AATGGGGCAC TGGGTGTGTA CGTGCTGTGG TTTCTGTTAG GGTCAAGACC    17313
AGGCTGTTTC TTACCTGGCT CGTACCTCCA AGTTCCAGG  TGATGAGTCC TGATTTTTGA    17373
AGTGAAGGAA TCCATTTAAT ATCAAAATTC TGTGACCTTA AATTTTTTC  TTTTATTATG    17433
TGTCATTTCA TATGTACGCA TATTTTTTG  TCTGTGTGTG GACATGCTTG TGGCGATCAG    17493
AGGACACTTC AGAAAGTCAG TTCTCTCCTG CCGTGTGGGT CCTGGGGAAT CAAATCCAAG    17553
TTGTCAGGCT TTATCCTGAA AATAAAAAGT AGACAGCCCT TGGGATCCAA AGCTTCTTAG    17613
GGCTGTGTGT CTTAGACACC ACCAGTGTTG CACAGCTGGT AACATGACAG TGTCCTGGAG    17673
TGCTGATTGG AAGCCACAGG CCTCTGTGCA GGGCGGTAGA CTTCCAGGGT ACGGGCAGG    17733
TGGGCGTTCT CTACAAAAAC CTTGTAATCG CGGACGTCTT GGAGATGCCC CCTAGGTATC    17793
ATGATTTTGG TGTGTGACAC AGCTGAACTG TCTTCATACT CAGGATATCA TGAAGTGCTG    17853
GGGTGCAGAC CACTCTCAGC CTCAGGCAGC CAGGACCCGG GGCTCCATCA GATTGCGGTG    17913
ACTACCACAG AGGGTGGCCT TCCTTCCGGT CAGTGTGGGT GTGGGAGCTG GCAGGAAGTG    17973
GCTCCAGGCT TCCTTTAAGC ATCCTCTGCC CACAGCCCCA AACATGTTCT TTGGCAATGG    18033
CTTGCAACTA GAGGTGAACT CTCTCCTGTA CTATGTCCTG ACCCACGCTG CTGCATCTAT    18093
TATACCTTTC ACACGCGTGA TGGGTACCCA GCGGGGCTGC TAGGCAGGGT TAAGCACTCA    18153
TCTTGTTTCC TGGTGCTGAA GCTGTGGTAA AGAAACTGAG GCCATTTTCC CTTGAGAGAG    18213
```

```
ATGGTCTCAG CCAGGTCTTT CTCGGCCTGG GGAGCCCGGA AGAAAGGATG TACTACAGTG   18273
AGTGGACACT TGTTGGCTGA TGGCCTTGGT AGGTCCTTCA CCCTGGGAAG TGCTGTTTCT   18333
TATCTGTTAG AGATGCTGAC CTCAGCAGGA CTGGAGGAAC TGCATGGGAG GTGTAGGAAT   18393
GAAAGTGAGT GGGGAAAATT ATCTCCAGCC CTAGGGAAGT CTGAGGCCTG TGTCCCCTTT   18453
GTCCTGGACT GGGCCCCTGC CTTGGGTGTC TGTCCAGGGT CTTTGCTCTA CAGCCCCAGC   18513
GGATGCCCAA AGTAGACGAG TCAACTGGTC CTTTCTTTCA CCCTGTGTCC ACTTCTCATG   18573
TATCTACCTT CATAATCCTT CTAGGTAAAA CAAGCCTCTA ACTTTGGGTT TTCAAATCAG   18633
CCAGCTTCCA GGCTCGATAG TACGAACCAT GAAAATCTTT CTTACCATGA GGTTGTTTTC   18693
TAGTGTGTGT GTGTGTGTGT GTGTGTGTGT GTGTGTGTGT GTGTGTGTAC GTACACATAT   18753
GTACCTCTAT CAGTGTGCTG TGCGTGTACC ACAGCAGACT CGTGAGGAGG TCAGGCAAAC   18813
TTTATAAAAA TCTTTTTTTT TTGCTTCACT TGAGTCCCAG GGTCACACAG TGGCAAGTGC   18873
TGAGCTCTGT TCTCTGTTCT TGATTTGTTT TGTGAGCAGC TGATGTTCTT AAGGCTTGCG   18933
GAGGGGAAAG GTAGGGCTGG CTTGCTTCTT CCCCGAGTGG CGGTCAATCC CTAGACATCT   18993
CTAAGCCGTG GCCACACGTC CTGGAAGGAC CCAGGTCAGA AGTGATACTG AGATGGCCCT   19053
GTGAGCCCTC TCGAACACAC AGGGTTGTAA ATAGTACCTG ATTGTTACAT TGGAGACTCG   19113
TCAGCTGGGT GGAGTCCTGG TTCAGAGGGA GTTATTCCTC CCCCCACATT TCTTCTCTTC   19173
TGGGGCTGAA GTCTCTTCCT TCCTTACCTG TGATGCTGTC ATGATAGGTC CCAGCTGAGA   19233
GTGGAGGCGG GGCAGTCAGG GAGCTGCTTC TCTTTGCTTA GCAGGGGTTG GAGACTTGGG   19293
GTGTAGGGGT TGGCTCCCCC TTTCCCTGCC CTGGACCTGG TTTCTGGTTT CAGCAGAGAT   19353
TCGTTCTAGA AACTTGTTGC GTAAACAAGA TCACAAAGCG ATAAGCTTGA GCAAAACCCA   19413
GGGGAACAAA TTGCTTCCCT GTGAAGACCC AATCTTAGCT CTTAGAGAAG CCCTCCCTTT   19473
TGGAAATTGC TGACTTTCAG GGCTTCTCTG TGGAGGAAAG AGGCTAGCCG CCGTATGTTT   19533
GCCTGGATTC CAATAAATCT TTGCGGCCTT GGCTACCCCT TGTTGAACAA GGTCTGCACT   19593
CCTAATGCGT GCCTCAGGTG GTCTGAGACC TCTACCCCAT CTCCAGCTTT TCCTTCCTAT   19653
GGAGGGAGTC AGTGGGTTAG GAGAGAATGG AGTTGAGTCC TGGAATGAGG AGGAAGCTAT   19713
GAACTCGGGG CCTGTTCCTG TCTGGTGGGT GCTCTTCTCC GCCGCTGAAG GAGGCAGCCG   19773
CAGGGAAGAC TACCACAGGA ATCGAGTAC CACCTGGAGC AGTGTATACA GGATGTGGGC   19833
TGATGTGTGG TAAGGGCATG ATGGGCTGAT GTGTGGTAAG GGCATGGGAT CTGATTGCTC   19893
TGTGGATGGG CCACAGGGAA ATTTTGAGT GTCTACTGCA GTAGTTCTCA ACCTGTGGGT   19953
TGTGCGCCCC TTGGTGGGAG TTACATATTA GATATTTACA TTATGATTCA TAACTGTAGC   20013
AAAATTACAA TTGTGAAAGA ACCAAGAAAT CACCGCAGCA TGAGAACCTG TATTAAAGGG   20073
TCACGGTGTT AGGAGGGTTG AGAGCCACTC ATCCTCTGGG TCTAGGCCAT GGCGGGCTGT   20133
AACTGCTCTC TGGAGTTAAG CCACAGTGAA CCAGCTGTCC TTGCAGATGG ACTTGTGGAG   20193
GCTCCAAACC TTTGTCCAG GGGAGAAGAG CTTGCTTTTG CTTTGTACTT TTAAAGGAAG   20253
TTCAGTGGTC TTCGGGCCTT GTGGCTGCTG TGTGTGGAAG TGCCCCTGTA CAATAAGCTG   20313
TATAGATCGT GTACAACTGC AGTTTTCCTC CGTGGGTCCA CCAACCACTC CTGACTCCAC   20373
GGATGAGTGA GGCCAGTAGG GCTGTGTGTG GGTCCCTAGG CCAAGCATCC TGGACCACGA   20433
TGAGCCTCAG CTAGACCACT CTGGATCTTT AGCAGAGGCT CCTAGAGAGC TGGCTGGCTT   20493
CCTCCTGCCT TCTTTTCTCT TAAAACTTCG TCTCAATCGG AAGCTCCTCT GTGCACGTGA   20553
CCTCCAGGCC TGGGGGTCGC CACAAATCCC CTCATCACAA GACGAGCAGC TCGCATGAGG   20613
```

-continued

```
GACACGACAC TTGTTACCTA CCAGGCTGTG GGGTTTTTGT TGGTTGGTTG TTTTGTTTTG    20673
TTTTGTTTTT TTACTTGTAC AGAAGTGTTG TGACATCAGA TGTCAGCTGT TAGTGCTGGC    20733
ACCATTTTAC AGGTAGGGAA CTGAGGCTGT AAGATGTGTA GTGACATCGC TAAGGCCACT    20793
CAGTTGGTGA GGCCTTACCA AGGTCAGGTC TTTGGAGCCT TTTGCTGAAC CATGTACTTC    20853
TATCTCTGTT TTGTTGAAAC AAAGTCTATA TGGCTCTGGC TAGCCTATAA CCCCATATGT    20913
AGACGAGGCT GACCTCGAAT ACACTGCAGT CTTTTATGTC TGCCTTCTGG GTGGCAGGAT    20973
TGAAGGCATG TGATTCCTCC TAACTGTACA CTTTAAAAAA AAAATCATTC TTTGTTCTGG    21033
TCTGTGCCAG GGCCTTGTAA GATGTTCTGT GCTGAGCTGG GCTATTTGGG TTAGTCTCAT    21093
TGCTGAGCAG GGCCCCTGTA TCTTCCTTCT CTGTCACTTG CTTACCTGGG TCTTCCTCCT    21153
GCACTAGCTA TCCTAGAACC AGTACTGAGA GCAACTATGG GCCCAACTCT GCCCCTTGCC    21213
CAGCCTGCTT AGCTGGGGGC GGTGTTCCAC TTCCCTGCCC AAGTCCTGTG GGACTGTGTT    21273
TGTACTCCAC CACCTTCAGT TCCTTGGAGC TGGAGCAGGC CAGGCGGCTG CATTCCTGCA    21333
GCTGCTGTTG CCAGGGAGAG CCCATCCCAT TCACTTCAGT CTCCTTAATG TAGAAGCCTT    21393
GTCGAATTAG CTTCCACTGT CCCCAACCCA AGAGTACCCT GTCCTTTCTT CACTAAGAAG    21453
GCCAGGATAC AGTCCTTCCT GTGGCTGATA AGACAGGCCT TGGACAAGG  CCTGGGACCA    21513
CACTGTGTGG GCAAAGCTGC TTCAGCACCG ATGGCTCCTC CATGCCAAGC TTGGCTCTGC    21573
TTCTCACAGT TGAGACTTCT GTGCGCACAC CCACTGTCTA GCTCAGCTGG ACACTGATTT    21633
TCTTTAAATG TATAGATTTT GGGGTGGGGT GTGCTGAAAG CTCCCACTGA TGCCCCAAGC    21693
CTGAGTCTCA GAGTATGATC AATTGATGGC TTTCATGGGT ATCACAGCTT CTGTTCCAG    21753
GTCAGACTCC CTGACCAGTC AGAGCATCCT GGGGTTAGAC AATGTCCCCG TCACTTGTGC    21813
CTCCACCTGG CACCAGGCTA TGATGTTATG GCATTGAGGG TATGAGAAGG ACCAGGGGTT    21873
TCCCAGAGTT ACGCCCAGGC GCACAGGCAA TTGTTTCCTA CATGTGTGGC TGGAATGGTT    21933
GGGTGAGCCT TTTCAGCTGC CTACAATAGG AACCCAGGGA TACTGGGCAT TGACCAAGGC    21993
ATATCTCATA CCCTTTTCTT ATCTTTCTGC AG CAA ATT GTG GCT GTA AAT GTT     22046
                                   Gln Ile Val Ala Val Asn Val
                                                    25
CCT CCT GAA GAT CAG GAT GGC TCT GGG GAT GAC TCT GAC AAC TTC TCT     22094
Pro Pro Glu Asp Gln Asp Gly Ser Gly Asp Asp Ser Asp Asn Phe Ser
    30              35                  40                  45
GGC TCT GGC ACA GGTAAGACTG ACCCAGAACA CTGAGATGGC ATAGATCATG          22146
Gly Ser Gly Thr
GCTGGAGTGG TGAGCAGGCA GTCACCCAGC TTTAGTGAA  CCCCCTTCTT CTCCCATCCC    22206
ATCCTTAGCC ATTGGAGTCA GGACAGTGCC AAAAGGAAGA ATGGTATCCA GCTGCAAGCC    22266
ACTCAGCTAA GAGAAACTCT CAGAGAAATG AAGGGGTTCC ACCAGGCCAT GGCAGCCAC    22326
TAGAGCCAAC CCTTGGAGGA GTTGACTCC  ACTGAGCCTT GGTGTGGTGT TCCATCTGT    22386
GAGATGGGAA TACTTTGCCC AAGAGCCTGT TAGAAGCTGT AGGAAGCACA GAGTCGGCTA    22446
GGTATAGATT TGCTCTCACC TCCATCTCTC GATACCAGTT CTCTGCAGAG CTTGGGTTTG    22506
TGGGAGGGGT GGGGGGGTGA GGGGAGAAGG CTGTGAGCTG CAGCTAGCCA GAGGGGTCTC    22566
CCAGAAGAAT GGGGAGAGCT AAGAAGGAAA GTTGAGGTCA CAGTGGGAAG GAGACCAGAG    22626
CAAAGGGTTG GAAGGTAGGT AAAATGCAGC CGTGTATTCT TGGGAGCCTT AGGCCTTGGG    22686
CAAGAGGGTA GAAGAGGTGT TTGTCCTGGG CTGCAGTCCT GTATCAGCTC TGGTGTCTTG    22746
GCCCACGCTC ACAGCAGGAT CCCTTCCCAG ATTCCCGAGA ATTTCTCACA GTTCAGAGAG    22806
```

| | | | | | | | | | | | | |
|---|---|---|---|---|---|---|---|---|---|---|---|---|
|CACGCTACTT|GTAGGCAGGT|GAGGCTGCAA|AGGACAGCTT|TTCTGGCCTA|ATTTTCAAAG| | | | | | |22866|
|TGAGTTCAGC|CTTTGCTAGG|TCACCTTTGG|GGTCTCAGAA|GGCTTCAGCT|CCTGGTAGAG| | | | | | |22926|
|CATGAATCAC|GTCAGGCGTG|ATGCTGGAGA|CCTCTCCTAC|CCTGACACCC|CAAACCCCCA| | | | | | |22986|

```
CCTCTGACCC TGCA GGT GCT TTG CCA GAT ACT TTG TCA CGG CAG ACA CCT          23036
              Gly Ala Leu Pro Asp Thr Leu Ser Arg Gln Thr Pro
               50              55                  60

TCC ACT TGG AAG GAC GTG TGG CTG TTG ACA GCC ACG CCC ACA GCT CCA          23084
Ser Thr Trp Lys Asp Val Trp Leu Leu Thr Ala Thr Pro Thr Ala Pro
             65              70              75

GAG CCC ACC AGC AGC AAC ACC GAG ACT GCT TTT ACC TCT GTC CTG CCA          23132
Glu Pro Thr Ser Ser Asn Thr Glu Thr Ala Phe Thr Ser Val Leu Pro
             80              85              90

GCC GGA GAG AAG CCC GAG GAG GGA GAG CCT GTG CTC CAT GTA GAA GCA          23180
Ala Gly Glu Lys Pro Glu Glu Gly Glu Pro Val Leu His Val Glu Ala
         95             100             105

GAG CCT GGC TTC ACT GCT CGG GAC AAG GAA AAG GAG GTC ACC ACC AGG          23228
Glu Pro Gly Phe Thr Ala Arg Asp Lys Glu Lys Glu Val Thr Thr Arg
110             115             120             125

CCC AGG GAG ACC GTG CAG CTC CCC ATC ACC CAA CGG GCC TCA ACA GTC          23276
Pro Arg Glu Thr Val Gln Leu Pro Ile Thr Gln Arg Ala Ser Thr Val
             130             135             140

AGA GTC ACC ACA GCC CAG GCA GCT GTC ACA TCT CAT CCG CAC GGG GGC          23324
Arg Val Thr Thr Ala Gln Ala Ala Val Thr Ser His Pro His Gly Gly
             145             150             155

ATG CAA CCT GGC CTC CAT GAG ACC TCG GCT CCC ACA GCA CCT GGT CAA          23372
Met Gln Pro Gly Leu His Glu Thr Ser Ala Pro Thr Ala Pro Gly Gln
             160             165             170

CCT GAC CAT CAG CCT CCA CGT GTG GAG GGT GGC GGC ACT TCT GTC ATC          23420
Pro Asp His Gln Pro Pro Arg Val Glu Gly Gly Gly Thr Ser Val Ile
175             180             185

AAA GAG GTT GTC GAG GAT GGA ACT GCC AAT CAG CTT CCC GCA GGA GAG          23468
Lys Glu Val Val Glu Asp Gly Thr Ala Asn Gln Leu Pro Ala Gly Glu
190             195             200             205

GGC TCT GGA GAA CAA GTGAGTGGCT TTGCATTTCC TGGGTGGCCA CTAGTGCCTG          23523
Gly Ser Gly Glu Gln
             210
```

| | | | | | | | | | | | | |
|---|---|---|---|---|---|---|---|---|---|---|---|---|
|CACCTGGCCG|CCTAATGTCC|TCATTACAGT|GACAGGTGAC|AGGGTCCCAC|CTTCCTCCTG| | | | | | |23583|
|CCCGAAACAG|ACTGATTGCA|AGATCAGGAG|GTGGGCGACT|CCTTAGATGT|CATTCAGGAG| | | | | | |23643|
|CTTACAGCAG|GGTGAATTTT|CCGTCTTAGA|CCTTCATGGG|AATTTTCACA|CAACAATGTG| | | | | | |23703|
|TACGTTGTGT|CACTGGAGGC|GGTATCTGTG|TCTTGGCCTG|CCAGGGTCCC|AGGTGTGACT| | | | | | |23763|
|GACTGCATTC|CTTGACAGAT|GCTGGTATAG|GTTGGCTACG|TCTGATGGGG|GTGGCAGGGG| | | | | | |23823|
|ATCCCATCAG|GTATGGCACT|GCTCAGGTTG|CTGTTGTGTC|AGTGGCTCCA|GCTGACCTGA| | | | | | |23883|

```
TCCCAACCTA CCCTTCTGTA G GAC TTC ACC TTT GAA ACA TCT GGG GAG AAC          23934
                       Asp Phe Thr Phe Glu Thr Ser Gly Glu Asn
                                       215                 220

ACA GCT GTG GCT GCC GTA GAG CCC GGC CTG CGG AAT CAG CCC CCG GTG          23982
Thr Ala Val Ala Ala Val Glu Pro Gly Leu Arg Asn Gln Pro Pro Val
             225             230             235

GAC GAA GGA GCC ACA GGT GCT TCT CAG AGC CTT TTG GAC AGG AAG GAA          24030
Asp Glu Gly Ala Thr Gly Ala Ser Gln Ser Leu Leu Asp Arg Lys Glu
             240             245             250

GTG CTG GGA GGTGAGTCTT CTTTCAGGTG GAGAGGAGGA GGCAGGTGGT                  24079
Val Leu Gly
255
```

| | | | | | | |
|---|---|---|---|---|---|---|
|GGCTCTGAGG|TAGCCTGGGT|TGCTGGGGTG|AAGCATCTTT|AGCAGCAGGG|TGGGGAAGGA|24139|

-continued

| | |
|---|---|
| GGAGGGTCAA TTCTACTCCA GGCCACCTCC TAGGCTGTCC GTCTAGTCTG GGAGAGACTA | 24199 |
| CCACTGACCC CGTGGAGCTA CTGATCTGAG CCTGCCTCTG TTCACTCCCT A GGT GTC | 24256 |

Gly Val

```
ATT GCC GGA GGC CTA GTG GGC CTC ATC TTT GCT GTG TGC CTG GTG GCT       24304
Ile Ala Gly Gly Leu Val Gly Leu Ile Phe Ala Val Cys Leu Val Ala
        260                 265                 270

TTC ATG CTG TAC CGG ATG AAG AAG AAG GAC GAA GGC AGC TAC TCC TTG       24352
Phe Met Leu Tyr Arg Met Lys Lys Lys Asp Glu Gly Ser Tyr Ser Leu
    275                 280                 285

GAG GAG CCC AAA CAA GCC AAT GGC GGT GCC TAC CAG AAA CCC ACC AAG       24400
Glu Glu Pro Lys Gln Ala Asn Gly Gly Ala Tyr Gln Lys Pro Thr Lys
290                 295                 300                 305

CAG GAG GAG TTC TAC GCC TGATGGGGAA ATAGTTCTTT CTCCCCCCAC              24448
Gln Glu Glu Phe Tyr Ala
            310
```

| | |
|---|---|
| AGCCCCTGCC ACTCACTAGG CTCCCACTTG CCTCTTCTGT GAAAAACTTC AAGCCCTGGC | 24508 |
| CTCCCCACCA CTGGGTCATG TCCTCTGCAC CCAGGCCCTT CCAGCTGTTC CTGCCCGAGC | 24568 |
| GGTCCCAGGG TGTGCTGGGA ACTGATTCCC CTCCTTTGAC TTCTGCCTAG AAGCTTGGGT | 24628 |
| GCAAAGGGTT TCTTGCATCT GATCTTTCTA CCACAACCAC ACCTGTTGTC CACTCTTCTG | 24688 |
| ACTTGGTTTC TCCAAATGGG AGGAGACCCA GCTCTGGACA GAAAGGGGAC CCGACTCTTT | 24748 |
| GGACCTAGAT GGCCTATTGC GGCTGGAGGA TCCTGAGGAC AGGAGAGGGG CTTCGGCTGA | 24808 |
| CCAGCCATAG CACTTACCCA TAGAGACCGC TAGGTTGGCC GTGCTGTGGT GGGGATGGA | 24868 |
| GGCCTGAGCT CCTTGGAATC CACTTTTCAT TGTGGGAGG TCTACTTTAG ACAACTTGGT | 24928 |
| TTTGCACATA TTTTCTCTAA TTTCTCTGTT CAGAGCCCCA GCAGACCTTA TTACTGGGGT | 24988 |
| AAGGCAAGTC TGTTGACTGG TGTCCCTCAC CTCGCTTCCC TAATCTACAT TCAGGAGACC | 25048 |
| GAATCGGGGG TTAATAAGAC TTTTTTTGTT TTTGTTTTT GTTTTAACC TAGAAGAACC | 25108 |
| AAATCTGGAC GGCAAAACGT AGGCTTAGTT TGTGTGTTGT CTCTGAGTTT GTCGCTCATG | 25168 |
| CGTACAACAG GGTATGGACT ATCTGTATGG TGCCCCATTT TGGCGGCCC GTAAGTAGGC | 25228 |
| TGGCTAGTCC AGGATACTGT GGAATAGCCA CCTCTTGACC AGTCATGCCT GTGTGCATGG | 25288 |
| ACTCAGGGCC ACGGCCTTGG CCTGGGCCAC CGTGACATTG AAGAGCCTG TGTGAGAACT | 25348 |
| TACTCGAAGT TCACAGTCTA GGAGTGGAGG GGAGGAGACT GTAGAGTTTT GGGGGAGGGG | 25408 |
| TGGCAAGGGT GCCCAAGCGT CTCCCACCTT TGGTACCATC TCTAGTCATC CTTCCTCCCG | 25468 |
| GAAGTTGACA AGACACATCT TGAGTATGGC TGGCACTGGT TCCTCCATCA AGAACCAAGT | 25528 |
| TCACCTTCAG CTCCTGTGGC CCCGCCCCA GGCTGGAGTC AGAAATGTTT CCCAAAGAGT | 25588 |
| GAGTCTTTTG CTTTTGGCAA AACGCTACTT AATCCAATGG GTTCTGTACA GTAGATTTTG | 25648 |
| CAGATGTAAT AAACTTTAAT ATAAGGAGT CCTATGAACT CTACTGCTTC TGCTTCTTCT | 25708 |
| TCTCTGGACT GGTGGTATAG ATATAGCCAC CCTTTGCCCA AACCCTGGTA GCTCGGGGAA | 25768 |
| GCTTGGCTTA AGGCTGCACG CCTCCAATCC CCCAAAGGTA GGATCCTGGC TGGGTCCAGG | 25828 |
| GTTCCTCTGA TTTATTTGGT TTGTTGTGT TGTGTTGTGT TTTTCTTTTG GCTAAACTTC | 25888 |
| TTTTGGAAGT TGGTAAGTTC AGCCAAGGTT TTACAGGCCC TGATGTCTGT TCTTCTAAAT | 25948 |
| GGTTAAGTA ATTGGGACTC TAGCACATCT TGACCTAGGG TCACTAGAGC TAAGCTTGCT | 26008 |
| TTGCAGGGCA GACACCTGGG ACAGCCTTCC TCCCTCATGT TTGCTGGAC ACTGCTGAGC | 26068 |
| ACCCCTTGCT TACTTAGCTC AGTGATGTTC CAGCTCCTGG CTAGGCTGCT CAGCCACTCA | 26128 |
| GCTAGACAAA AGATCTGTGC CCTGTGTTTC ATCCCAGAGC TTGTTGCCAG ATCACATGGC | 26188 |
| TGGATGTGAT GTGGGGTGGG GGTGGGGTCA TATCTGAGAC AGCCCTCAGC TGAGGGCTTG | 26248 |

-continued

```
TGGGACAGTG  TCAAGCCTCA  GGCTGGCGCT  CATTCATATA  ATTGCAATAA  ATGGTACGTG    26308
TCCATTTGGA  CAGCAGACAC  TTTGGTGTAC  TTGTGCAGTC  TCTTTTGGT   CTGGACCATG    26368
TCCAACTCTA  TCTGGTTTTT  GGAATGGGAG  CCTAACTGGC  CTGTGTTCTG  GCTTGGTACC    26428
AAATAGCAAC  AGTCAGTGGC  ATCCTTGCCC  AGGCCCCAGG  GCAGGACTAT  GCTCTTGCCA    26488
TATCCAGGAC  TCCCGACTTT  GCACCTGTTT  TCCCTCTGTG  TGTAGCATCA  TGAACTCCAG    26548
CTAGGTTGTT  CCTTTCCCTG  GGGTCAGGAG  GATTCTGCTG  ACTCTGAATG  TCAGGATTTG    26608
CTTTGTTCT   GTTTGCTTAT  TGGGCAATTC  TCAACCTTCA  CTAGCAACAG  TCTCATGTGT    26668
CAGGATTACA  AGTATTGCTT  GCACATTGAG  GG                                    26700
```

( 2 ) INFORMATION FOR SEQ ID NO: 2:

( i ) SEQUENCE CHARACTERISTICS:
        ( A ) LENGTH: 311 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Arg  Arg  Ala  Ala  Leu  Trp  Leu  Trp  Leu  Cys  Ala  Leu  Ala  Leu  Arg
 1              5                        10                       15

Leu  Gln  Pro  Ala  Leu  Pro  Gln  Ile  Val  Ala  Val  Asn  Val  Pro  Pro  Glu
          20                       25                       30

Asp  Gln  Asp  Gly  Ser  Gly  Asp  Asp  Ser  Asp  Asn  Phe  Ser  Gly  Ser  Gly
     35                       40                       45

Thr  Gly  Ala  Leu  Pro  Asp  Thr  Leu  Ser  Arg  Gln  Thr  Pro  Ser  Thr  Trp
50                       55                       60                       65

Lys  Asp  Val  Trp  Leu  Leu  Thr  Ala  Thr  Pro  Thr  Ala  Pro  Glu  Pro  Thr
               70                       75                       80

Ser  Ser  Asn  Thr  Glu  Thr  Ala  Phe  Thr  Ser  Val  Leu  Pro  Ala  Gly  Glu
                85                       90                       95

Lys  Pro  Glu  Glu  Gly  Glu  Pro  Val  Leu  His  Val  Glu  Ala  Glu  Pro  Gly
          100                      105                      110

Phe  Thr  Ala  Arg  Asp  Lys  Glu  Lys  Glu  Val  Thr  Thr  Arg  Pro  Arg  Glu
     115                      120                      125

Thr  Val  Gln  Leu  Pro  Ile  Thr  Gln  Arg  Ala  Ser  Thr  Val  Arg  Val  Thr
130                      135                      140                      145

Thr  Ala  Gln  Ala  Ala  Val  Thr  Ser  His  Pro  His  Gly  Gly  Met  Gln  Pro
               150                      155                      160

Gly  Leu  His  Glu  Thr  Ser  Ala  Pro  Thr  Ala  Pro  Gly  Gln  Pro  Asp  His
                165                      170                      175

Gln  Pro  Pro  Arg  Val  Glu  Gly  Gly  Thr  Ser  Val  Ile  Lys  Glu  Val
          180                      185                      190

Val  Glu  Asp  Gly  Thr  Ala  Asn  Gln  Leu  Pro  Ala  Gly  Glu  Gly  Ser  Gly
     195                      200                      205

Glu  Gln  Asp  Phe  Thr  Phe  Glu  Thr  Ser  Gly  Glu  Asn  Thr  Ala  Val  Ala
210                      215                      220                      225

Ala  Val  Glu  Pro  Gly  Leu  Arg  Asn  Gln  Pro  Pro  Val  Asp  Glu  Gly  Ala
               230                      235                      240

Thr  Gly  Ala  Ser  Gln  Ser  Leu  Leu  Asp  Arg  Lys  Glu  Val  Leu  Gly  Gly
                245                      250                      255

Val  Ile  Ala  Gly  Gly  Leu  Val  Gly  Leu  Ile  Phe  Ala  Val  Cys  Leu  Val
          260                      265                      270
```

| | | | | | | | | | | | | | | |
|---|---|---|---|---|---|---|---|---|---|---|---|---|---|---|
| Ala | Phe | Met | Leu | Tyr | Arg | Met | Lys | Lys | Lys | Asp | Glu | Gly | Ser | Tyr | Ser |
| | 275 | | | | | 280 | | | | | 285 | | | | |
| Leu | Glu | Glu | Pro | Lys | Gln | Ala | Asn | Gly | Gly | Ala | Tyr | Gln | Lys | Pro | Thr |
| 290 | | | | | 295 | | | | | 300 | | | | | 305 |
| Lys | Gln | Glu | Glu | Phe | Tyr | Ala | | | | | | | | | |
| | | | | 310 | | | | | | | | | | | |

( 2 ) INFORMATION FOR SEQ ID NO: 3:

( i ) SEQUENCE CHARACTERISTICS:
  ( A ) LENGTH: 2196 base pairs
  ( B ) TYPE: nucleic acid
  ( C ) STRANDEDNESS: both
  ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 3:

```
TCTAGAACAC TTATTAAGAG CCAGGCACTG AAAAGTGCAG ACTCCCTCAT TTCATCCTGG    60
CCGTGCTTAC AAGTAGTTTC CATGCTCTGG TAACCCTGTG CAGAGGGCAG CGTGGGAGGC   120
GGGCCGCTTG GTGGACGGTC ATGGGGCTC  TGCATGGGTG GTTGCCCTTG CCTCAGAAGA   180
ACTCCCTAAG TAAGAGCAAG TTAGCCTCCC TAACCCCTGG TGGGTTGTTG CTTCTTTTCT   240
CCTCTTGTTT CTGCCAAGAG AGGGTGGACC AAGAAGACCC CAGCCTACAG AACATGTGAT   300
CCAAATAAAC TTCTTTTTAG TATAAATGTC CTAGCCTGTG ACGTTCTGGT AGACTAGCAC   360
AAGATGGACC AAGACAACTC TCATCGAGAC TCTGAGGAAC GAACTGGCAT ACATGGGAA    420
CAGGAAATGA AGCTTAGAGA GAGGTTCTGT GGCTTGTCCA ACATGGCTGT AGTTTAAATC   480
CAGCTTGCCA CCAAAGCACA CACATTTCAC TGCTGTGCTG GGCCGGGCCT CAGATCCAG    540
GGGCTCCGGA GCTAGAAGGA CACGTGTATC AGCCATGGCT TCAGTTTATT GCTGTATACT   600
CTGTGCTTCT GGCTCTCATG GAAAGACAG  ACATTGGGGT TCTTATAATC TCTCCCTCTC   660
CCCTCCCCAC ACTCTATCCC CAAAGGAGGC ACCACTTCTG CAGGTAAATG TTATCTTCAA   720
AGCGCTCACA TCGCAACCTT TGCCCACACC ATCTCATTAA AGGAATTGGC AGTGACTTTA   780
AGGTGAAAGA ACTCGGTGGC TACGTGTTAT ATAAATTTGC ATCTGGGTCT CAGAGCTGGA   840
AGGAAGGCAC TCCCATACAT GCAGTCTGTA CATGCAGTCG GATGATGGAC CAACAACACA   900
TTGTGATTTA TGCCCCTGCT GGTGAGCCCA GGAATCCCTG TAGCACTCTC TCTCAGCTCT   960
AGGGCCCTGC TTGTGTATGG AAAACGCTTA GTGTTTTATA GGTATTTGT  CAGAATACTT  1020
TAAGGAACTT GACCAAAGTT ACAGGGAGGT TAGACAGATT GTCATGGTAT ACTCACCTCT  1080
GTCTCTGACC CTCCTAACTG GGACCTCTTT AGTCTCCCTT GAGGCAGGGA GTGCCACATG  1140
CATGTGTCCA GGCACATGTC TCCTGGTTTA CCTCCCAACG CACCTCAAGT CCCCAAGGTA  1200
GGTAGGCACT TGTATTCTGT AATTCAGAGA GGCAAATCAA ACTGTTACAA TGTTTGCCCA  1260
AAGCTCCCCA AGCAAAGTGG CCCTAAGAGT GAGCAAAGAG ACTGCGTGCC TTCACTGCCT  1320
GTGTGAATCC CTGCAGATAG TCTCTCATCT TGGTGCCCTT CCCACAGAGG CTGGGGCGGC  1380
AGGAGGGAGC CTGGACAGCT CAGACACTGG GTCATTGATG ACTGTTGTGT GGGATACCTG  1440
CCGGGGCGCA GGAGTGAGCC ATGCCACCCC AGGAAGTGGT TCAGGGTGAC TCTTCTTGGC  1500
ACACCTGGGA GGATGTAGCT GGTGCTGGCA CACCCACCGT CACGAGAGCT TCCTGTCCAA  1560
ACCTTCAACA AAGGCGGCTT CTTGAGACAG GCTAGACTGA AGTCACCAGC CTTGGGTGGG  1620
```

| | | | | | | |
|---|---|---|---|---|---|---|
| GTCCACTATG | TAACCTCAGT | GCTCAGGAAC | CCTTTCCCAT | ACTGTCTGGA | ACTATACTGT | 1680 |
| ATGTAGCTGG | GTTTCCACGC | ATGTGTGCCT | GCACCCAGTC | CATCTCATCT | TCTATCTCCC | 1740 |
| TCCCCTTTCC | CGCTTCCCCC | CTCCCCACTC | TCCATCTCAT | CTTCCATCCC | CACCTCTTCT | 1800 |
| GGTCCCTGCC | CTGCTAAACT | CAGGGTAGCT | GCATTCCGCT | GGCCTTCCCC | ATGTTCCAGG | 1860 |
| CTTCAGTCCC | TTCTCTGCAC | CTGTCCTTTG | TGAAGTGACC | AGAGGATTTC | TGATCCTGTC | 1920 |
| TCTGTCGCTC | TGAAGGGTCA | GGAGTTCCTC | CTGCCTGGAC | AAAGCCATCC | TGACGCACAT | 1980 |
| AAATAAAACA | AACATCAAAC | TCTATTCAAC | CCCCTGGAAC | CCGTGTGTGT | TACTTACAGG | 2040 |
| GCAAAAGAAT | GGAGCAGGGG | ATGGGTTGTG | GGGGGGGGGG | GTGGCATCTG | GGTTGTCTAC | 2100 |
| AGTTGTGCAT | TAAGTTGTAA | TTAAGATGTG | CATTTCTCCA | AATAAGGGAA | AATTATTCTG | 2160 |
| GATTATTTGA | GTGAAGCTGA | AAGGTGATCA | TCTAGA | | | 2196 |

( 2 ) INFORMATION FOR SEQ ID NO:4:

( i ) SEQUENCE CHARACTERISTICS:
( A ) LENGTH: 350 base pairs
( B ) TYPE: nucleic acid
( C ) STRANDEDNESS: both
( D ) TOPOLOGY: both ( x i ) SEQUENCE DESCRIPTION: SEQ ID NO:4:

| | | | | | | |
|---|---|---|---|---|---|---|
| AGGCACATGT | CTCCTGGTTT | ACCTCCCAAC | GCACCTCAAG | TCCCCAAGGT | AGGTAGGCAC | 60 |
| TTGTATTCTG | TAATTCAGAG | AGGCAAATCA | AACTGTTACA | ATGTTTGCCC | AAAGCTCCCC | 120 |
| AAGCAAAGTG | GCCCTAAGAG | TGAGCAAAGA | GACTGCGTGC | CTTCACTGCC | TGTGTGAATC | 180 |
| CCTGCAGATA | GTCTCTCATC | TTGGTGCCCT | TCCCACAGAG | GCTGGGGCGG | CAGGAGGGAG | 240 |
| CCTGGACAGC | TCAGACACTG | GGTCATTGAT | GACTGTTGTG | TGGGATACCT | GCCGGGGCGC | 300 |
| AGGAGTGAGC | CATGCCACCC | CAGGAAGTGG | TTCAGGGTGA | CTCTTCTTGG | | 350 |

SYNDECAN STIMULATION OF CELLULAR DIFFERENTIATION

CROSS REFERENCE TO RELATED APPLICATIONS

This application is a division of application Ser. No. 08/206,186, filed on Mar. 7, 1994, which is a continuation-in-part of U.S. application Ser. No. 07/988,427, filed Dec. 1, 1992, now abandoned, said Ser No. 206,186, Mar. 7, 1994, which is a continuation-in-part of PCT/FI93/00514, Dec. 1, 1993, which is fully incorporated by reference.

FIELD OF THE INVENTION

This invention is in the field of cancer biology and therapy. Specifically, the invention is directed to methods for altering the differentiated state of a cell by altering syndecan expression. The method allows for the normalization of the growth rate and differentiation state of malignant cells, and is based on the stimulation of syndecan expression in the malignant cells. Re-expression of syndecan in such malignant cells promotes their normal differentiated phenotype and prevents their formation into tumors. This method may also be applied to normal cells to maintain their expression of genes characteristic of the differentiated state, e.g. the method may be used to prevent baldness by maintaining keratin production. In addition the invention is directed to transcription regulatory elements associated with the syndecan gene and to the use of such elements for controlling gene expression.

BACKGROUND OF THE INVENTION

Cell surface proteoglycans play an important role in the regulation of cell behavior (Ruoslahti et al., Cell 64:867–869 (1991)). Through their covalently bound glycosaminoglycan side chains, such proteoglycans can bind various extracellular effector molecules (Jalkanen, et al., in Receptors for Extracellular Matrix, J. MacDonald & R. Mecham, Editors, Academic Press, San Diego, pp. 1–37 (1991)). One central challenge in proteoglycan biology is to understand the biological consequences which result from the binding of different effector molecules to cell surface proteoglycans. It is important to determine the intracellular responses triggered by effector binding and how these responses lead to altered cellular behavior. One way to investigate these matters is to create biological models which are dependent on the expression of specific proteoglycans.

Syndecan is the best characterized cell surface proteoglycan (Saunders et al., J. Cell Biol. 108:1547–1556 (1989); Mali et al., J. Biol. Chem. 265:6884–6889 (1990)). It was originally isolated from mouse mammary epithelial (NMuMG) cells as a hybrid proteoglycan containing both heparin sulfate and chondroitin sulfate glycosaminoglycan side chains (Rapraeger et al., J. Biol. Chem. 260:11046–11052 (1985)). Recent studies have revealed its expression, not only on epithelial cells but also on differentiating fibroblasts of developing tooth (Thesleff et al., Dev. Biol. 129:565–572 (1988); Vainio et al., J. Cell Biol. 108:1945–1964 (1989)), on endothelial cells of sprouting capillaries (Elenius et al., J. Cell Biol. 114:585–596 (1991)) and non on the surface of lymphocyte subpopulations (Sanderson et al., Cell Regul. 1:27–35 (1989)). This suggests that syndecan function can vary from one cell type to another. Syndecan belongs to a family of proteoglycans with conserved plasma membrane and cytoplasmic domains but with dissimilar ectodomains (Mali et al., J. Biol. Chem. 265:6884–6889 (1990)). The conserved structure of syndecan suggests that it could participate in signal transduction through the plasma membrane.

Syndecan binds several extracellular effector molecules but does so in a selective manner. For example, syndecan binds interstitial collagens and fibronectin but does not bind vitronectin or laminin (Koda et al., J. Biol. Chem. 260:8156–8162 (1985)); Saunders et al., J. Cell Biol. 106:423–430 (1988); Elenius et al., J. Biol. Chem. 265:17837–17843 (1990)). Moreover, syndecan isolated from tooth mesenchyme has revealed selective binding to tenascin not observed for syndecan from NMuMG cells (Salmivirta et al., J. Biol. Chem. 266:7733–7739 (1991)). This suggests that variations in syndecan glycosylation alters the binding properties of syndecan. Polymorphism of syndecan glycosylation has also been observed in simple and stratified epithelia (Sanderson et al., Proc. Natl. Acad. Sci. USA 85:9562–9566 (1988)); but whether these changes also reflect altered ligand recognition by syndecan remains unknown. Syndecan also binds growth factors, such as basic fibroblast growth factor (bFGF) (Kiefer et al., Proc. Natl. Acad. Sci. USA 87:6985–6989 (1990); Elenius et al., J. Biol. Chem. 267:6435–6441 (1992)). Very recently, Yayon and coworkers (Yayon et al., Cell 64:841–848 (1991)) and Rapraeger and co-workers (Rapraeger et al., Science 252:1705–1708 (1991)) have shown that heparin-like molecules are required for the binding of bFGF to its high affinity receptor, indicating that syndecan-like molecules can also modulate the growth factor response. The fact that cell surface proteoglycans can bind both growth factors and matrix components suggests that proteoglycans play a role in regulating, both temporally (timing of expression) and spatially (precise localization), growth promotion by immobilizing effector molecules to the vicinity of cell-matrix interactions. This is supported by the pattern of syndecan expression during development which follows morphogenetic, rather than histological, patterns (Thesleff et al., Dev. Biol. 129:565–572 (1988); Vainio et al., J. Cell Biol. 108:1945–1954 (1989) and Vainio et al., Dev. Biol. 134:382–391 (1989)), and by the observation that syndecan expression is localized to sites of active proliferation (Elenius et al., J. Cell Biol. 114:585–596 (1991) and Vainio et al., Dev. Biol. 147:322–333 (1991)).

In simple epithelium, syndecan is polarized to baso-lateral surfaces where it co-localizes with actin rich cytofilaments (Rapraeger et al., J. Cell Biol. 103:3683–2696 (1986)). Upon rounding, syndecan is shed from the cell surface by proteolytic cleavage of the core protein at the cell surface, a process which separates the matrix binding ectodomain from the membrane domain (Jalkanen et al., J. Cell Biol. 105:3087–3096 (1987)). In this way, syndecan has been proposed to be involved in the maintenance of epithelial morphology. When mouse mammary tumor cells (S115) are induced to change their morphology from an epithelial to a more fibroblastic or fusiform phenotype, syndecan expression is lost (Leppä et al., Cell Regul. 2:1–11 (1991)). This lost has been found to occur in other cell types undergoing transformation (Inki et al., Am. J. Pathol. 139:1333–1340 (1991); Inki et al., Lab. Invest. 66:314–323 (1992)), suggesting that the loss of syndecan expression is a common characteristic of malignant transformation.

SUMMARY OF THE INVENTION

The present invention is directed to a method for altering the differentiated state of a host cell by altering its expression of syndecan. The invention is also directed to a method for inducing and regulating syndecan expression, especially in cells which exhibit a malignant phenotype, regardless of the origin of transformation.

In another aspect, the invention is directed to a treatment for suppressing tumor growth in a patient in need of such treatment, by the administration of a composition comprised of efficacious amounts of one or more agents that stimulate syndecan synthesis in the tumor cells of such patient.

The invention is also directed to the DNA encoding enhancer and suppressor elements of the syndecan gene and to the use of these elements for regulating heterologous gene expression. The vectors and host cells which incorporate DNA sequences containing the syndecan enhancer or suppressor are also encompassed by the invention.

In addition, the invention is directed to a method for enhancing syndecan expression in a host cell, by enhancing syndecan gene transcription.

The invention is also directed to a method for the enhancing syndecan expression in malignant cells, by preventing suppression of syndecan gene transcription.

The invention is also directed to a biochemical method for the inactivation of suppressors of syndecan gene expression in malignant cells.

In another aspect, the invention is directed to a method for stimulating cellular differentiation by enhancing syndecan expression in both malignant and normal cells.

The invention is also directed to a method for stimulating cellular proliferation and differentiation, thus promoting tissue regeneration, especially in processes such as wound healing, by enhancing syndecan expression.

Further features, objects and advantages of the present invention will become more fully apparent from a detailed consideration of the following description of the subject invention when taken together with the accompanying drawings.

BRIEF DESCRIPTION OF THE DRAWINGS

FIG. 1 is a diagram of the assembly of mouse syndecan gene and its promoter region.

FIGS. 2(a)–2(f). FIGS. 2(a)–2(f) contain the complete sequence of the mouse syndecan gene [SEQ ID No: 1: (DNA) and SEQ ID No: 2: (protein)]. Regulatory sites for the expression of syndecan may also exist on the first intron following the first exon (see FIG. 1).

FIG. 3 is a diagram of the assembly of mouse syndecan promoter region and the localization of the enhancer and suppressor elements together with restriction sites for three different enzymes.

FIG. 4. FIG. 4 is the complete sequence of the mouse syndecan enhancer element [SEQ ID No. 3: (DNA)] located 8–10 kbs upstream from the transcription initiation site as indicated in FIG. 3.

FIGS. 5A–D. FIGS. 5A–D is a photographic presentation of the reduced growth ability of syndecan-transfected cells in soft agar. FIG. 5A is a picture of the colonies in wild-type S115 cells that are formed in soft agar in the presence of testosterone, a feature typical for hormone-transformed cells. FIG. 5B is a picture of the colonies of control transfected cells that are formed in soft agar in the presence of testosterone. FIGS. 5C and 5D depict colonies of two independent syndecan-transfected cell clones formed in soft agar. Growth was not observed with the syndecan-transfected cell clones, demonstrating how syndecan re-expression can overcome the effect of hormone-induced transformation.

FIG. 6. FIG. 6 is a graphical presentation of how syndecan-transfected cells lose their ability to form tumors in nude mice. Wild-type or control transfected cells produce tumors in testosterone-administered nude mice while syndecan transfected cells revealed a very low tendency to produce tumors.

FIG. 7 is a graphical representation of enhanced syndecan expression in 3T3 cells by simultaneously administered basic fibroblast growth factor (bFGF) and transforming growth factor beta (TGF-β). This is an example of how syndecan expression can be enhanced as a result of growth factor action in normal cells during the differentiation process.

FIG. 8 is a graphical representation of enhanced syndecan expression by MCF-7 cells exposed to the anti-estrogen toremifene. When exposed to estrogen, syndecan expression in MCF-7 cells was reduced and the cells transformed. Subsequent treatment with the anti-estrogen (toremifene) restored syndecan expression to levels close to that found in cells not exposed to estrogen and aided the cells in maintaining their normal growth behavior.

FIGS. 9A–B is a graphical presentation of how the suppressor element (see FIG. 3) is active in S115 cells treated with testosterone. In FIG. 9A, the indicated stretches of promoter sequences were transfected in hormone-treated S 115 cells and analyzed for their transcription activity as described in Example VI. In FIG. 9B, the indicated stretches of promoter sequences were transfected into 3T3 cells. A dramatic drop in expression was observed with the suppressor construct as indicated in FIG. 3, which was more obvious in transformed S115 cells than in 3T3 cells. The vertical axes shown in the figures represent percent expression, wherein expression in the absence of suppressor is taken as 100%.

FIG. 10 is a graphical presentation of how the enhancer element is active in growth hormone-treated 3T3 cells. Various stretches of promoter were transfected in 3T3 cells and analyzed for their transcription activities. Fragment pXb6, which is the same as illustrated in FIG. 3 as an enhancer, revealed more than a ten fold stimulation of expression in 3T3 cells exposed to growth factors bFGF and TGFβ if compared to non-treated cells. The vertical axis of the figure represents percent expression wherein the expression observed in untreated cells is taken as 100%.

DEFINITIONS

Figure 1:
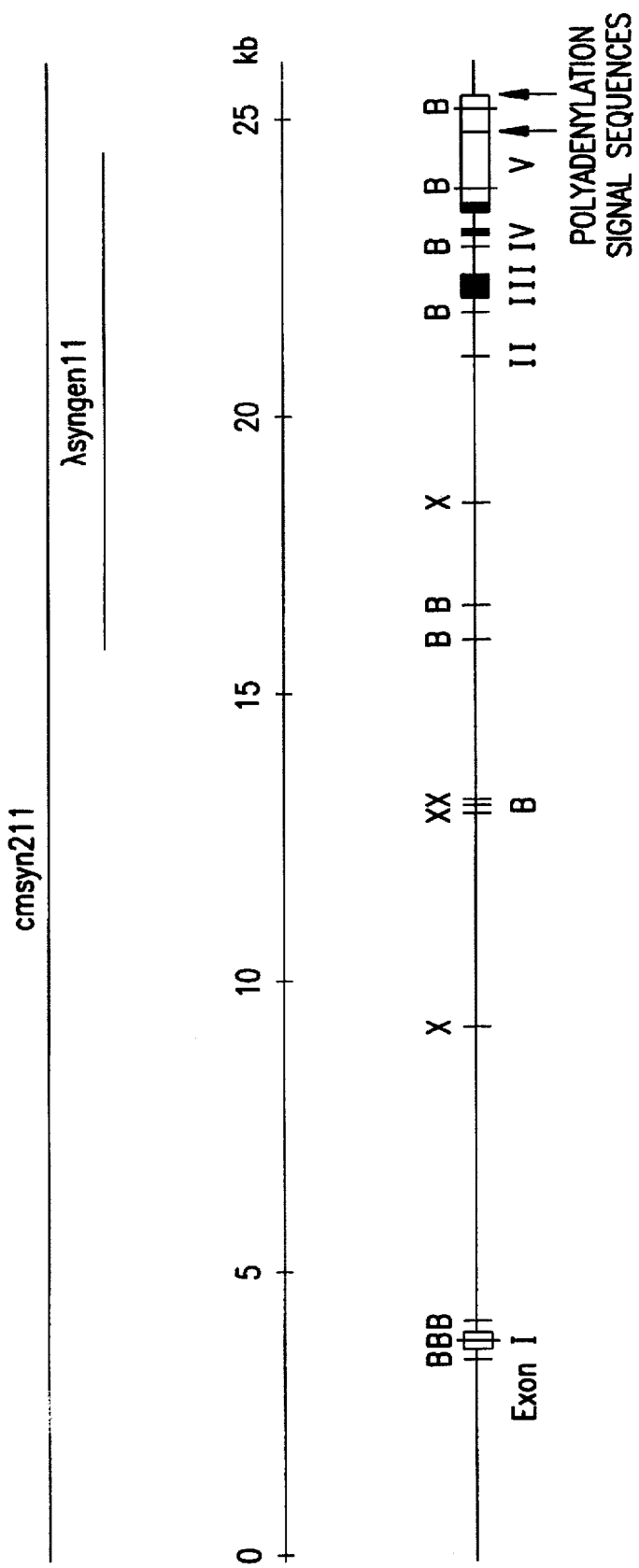
FIG. 1.
Figure 3:
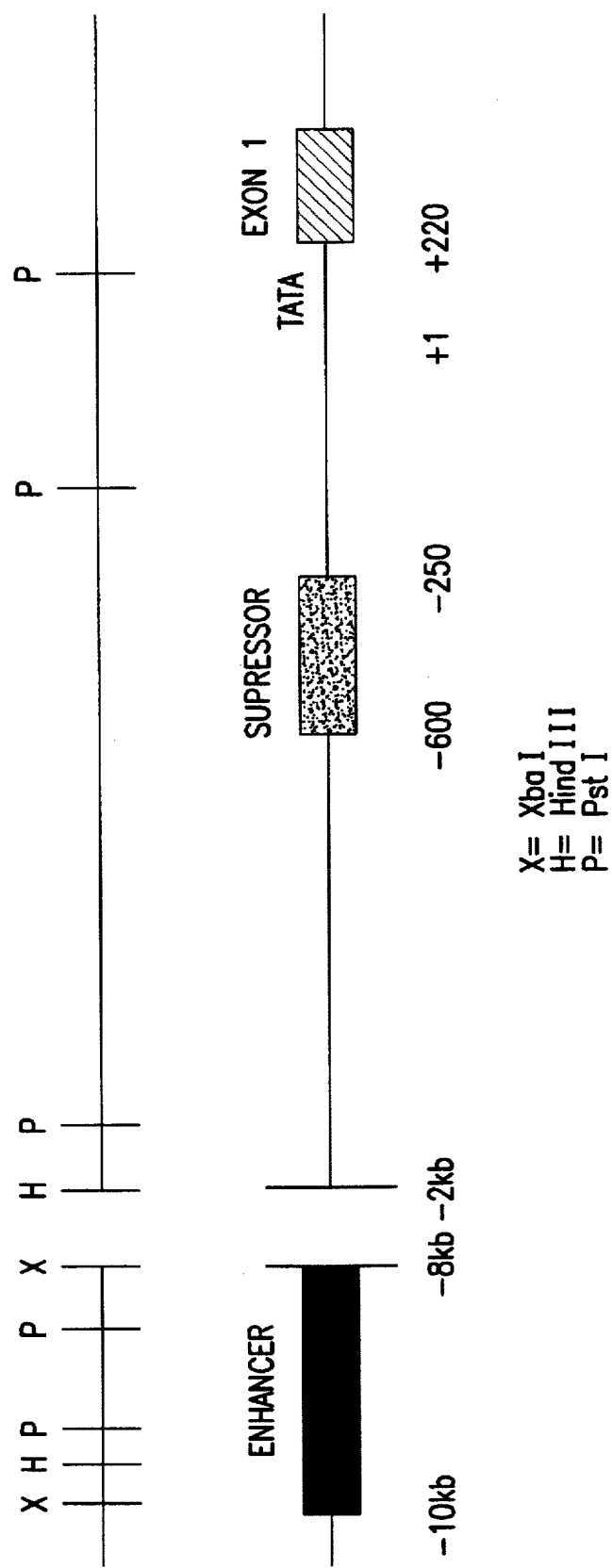
FIG. 3.

In order to provide a clearer and more consistent understanding of the specification and claims, including the scope to be given such terms, the following definitions are provided.

"Enhancement" or "Stimulation" of Syndecan expression. By "enhancement" or "stimulation" of syndecan expression" is meant an effect of increasing the synthesis of syndecan, either by the induction or de-suppression (de-repression) of syndecan gene transcription and/or translation.

Cell growth. By "cell growth" is meant cell replication, both controlled and uncontrolled.

Malignant. By "malignant" is meant uncontrolled cell growth.

More Differentiated Phenotype. In stating that a cell has a "more differentiated phenotype," it is meant that the cell possesses a phenotype usually possessed by a certain cell type more differentiated than the cell, which the cell was deficient in prior to enhancement of syndecan expression. This phenotype may be defined by one or more phenotypic characteristics. For example, an epithelial cell is a more differentiated phenotype of a mesenchymal-like shape;

therefore, the ability of the method of the invention to maintain cells in an epithelial cell morphology rather than a mesenchymal-like shape is a more differentiated phenotype within the meaning of the definition. Continuous syndecan expression is necessary for the maintenance of terminal differentiation of epithelial cells.

Syndecan expression is also linked to the normal differentiation of mesenchymal cells. However, unlike epithelial cells, continued expression of syndecan is not needed for maintenance of terminal differentiation in mesenchymal cells. To induce differentiation of suitable mesenchymal precursors (such as a "condensing mesenchymal" cells) to fully differentiated mesenchymal cells, only a transient expression of syndecan is required. A terminally differentiated mesenchymal cell is a "more differentiated phenotype" than a condensing mesenchymal cell.

Other phenotypes that are characteristic of syndecan-deficient cells but not of their non-deficient counterparts include fusiform shapes with long filopodial extensions. There is an extensive under- and overlapping of these processes causing the cells to appear to have a defect in cell adhesion.

In another example, syndecan-deficient NMuMG cells continue to secrete milk fat globule antigen (and thus appear mammary-like) and continue to express cytokeratins (thus appear epithelial-like). However, their actin-containing cytoskeleton is disorganized and their expression of $beta_1$ integrins and E-cadherins at the cell surface is markedly reduced. Upon increased expression of syndecan, these phenotypes are corrected so that there is no reduction in cell surface integrins or E-cadherin and the cell has an epithelial morphology. Therefore, the amount of cell surface integrins or E-cadherin is useful as a marker of syndecan expression and may be used to monitor the amount of a drug needed for efficacious results according to the method of the invention.

Efficacious Amount. An "efficacious amount" of an agent is an amount of such agent that is sufficient to bring about a desired result, especially upon administration to an animal or human.

Administration. The term "administration" is meant to include introduction of agents that induce syndecan expression into an animal or human by any appropriate means known to the medical art, including, but not limited to, injection, oral, enteral and parenteral (e.g., intravenous) administration.

Pharmaceutically Acceptable Salt. The term "pharmaceutically acceptable salt" is intended to include salts of the syndecan-inducing agents of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Vehicle. The term "pharmaceutically acceptable vehicle" is intended to include solvents, carders, diluents, and the like, which are utilized as additives to preparations of the syndecan-inducing agents of the invention so as to provide a carrier or adjuvant for the administration of such compounds.

Treatment. The term "treatment" or "treating" is intended to include the administration of compositions comprising efficacious amounts of syndecan-inducing agents to a subject for purposes which may include prophylaxis, amelioration, prevention or cure of a medical disorder, suppression of tumor growth, or the promotion of hair growth.

DETAILED DESCRIPTION OF THE PREFERRED EMBODIMENTS

Briefly, in its broader aspects, the present invention comprehends a method for maintaining a differentiated phenotype in a normal (non-malignant) cell that otherwise would suppress syndecan expression, by maintaining syndecan expression in such cell. The invention also comprehends a method for inducing a more differentiated phenotype in a malignant cell that lacks (or is deficient in) syndecan expression, by stimulating syndecan expression in such a cell. As used herein, a cell said to "lack" syndecan expression, may either be completely deficient in syndecan protein or produce insufficient syndecan to maintain or attain a desired differentiated phenotype.

The methods of the invention will not only prevent the progression (worsening) of a transformation state and the growth of tumors, but will also maintain cells in a state in which they continue to perform differentiated functions. Examples of differentiated functions of non-malignant cells include the secretion of specific proteins and/or other macromolecules and hair formation by epidermal cells of skin. Thus, according to the invention, administration of agents capable of inducing syndecan expression in epidermal skin cells of the scalp will promote hair growth among bald (or balding) people.

The subject method may be accomplished by biochemical, chemical or even molecular biological methods. While the method is applicable to a variety of cancer (both malignant and non-malignant) and normal cells, it is particularly adaptable for treating malignant cells which have become transformed. This includes cells transformed due to hormonal influences of the body or environmental influences, such as chemicals or radiation exposure. The method is especially effective for tumors characterized by loss of syndecan expression, for example, a glioma, myeloma, carcinoma, sarcoma, lymphoma, or adenoma.

Generally, any cell genetically capable of expressing syndecan can be stimulated to express syndecan by the method of the invention. Syndecan is naturally expressed in a wide variety of epithelial cells in mature and embryonic tissues and by various embryonic mesenchymal tissues undergoing inductive interactions with epithelia. In addition, syndecan is naturally expressed by Leydig cells, by developing B-lymphocytes and by a subpopulation of plasma cells.

Enhanced syndecan expression may be achieved by administration of compositions containing a biochemically, and/or chemically and/or molecular-biologically active component to an individual. Compositions may be administered orally, intravenously, subcutaneously or locally, or by any other method which will allow cells, normal or malignant, to be exposed to the syndecan expression enhancing component.

By a "biochemically" or "chemically" active component is meant a component that alters the endogenous syndecan biochemistry or chemistry of the target cell without altering syndecan gene expression per se. Such alteration may include altering the half-life of syndecan protein or mRNA, so as to increase levels of syndecan protein in the cell. For example, by altering the external domain of the cell's endogenous syndecan, or its cell surface membrane properties in general, may be altered so as to retain higher levels of syndecan on the cell surface; and, altering the syndecan protein active site(s), so as to enhance the efficiency of the syndecan response.

By a "molecular-biologically" active component is meant a component that alters endogenous syndecan gene expression in a manner that allows for an increase in cellular syndecan, such as, for example, by stimulating transcription, preventing (or reducing) suppression of transcription, derepression of transcription, or by generally increasing levels of mRNA and/or translation efficiency.

It is known that cellular transformation involves activation of cellular growth-stimulating genes (e.g., oncogenes) and inactivation of other genes which suppress cell growth. It has recently been shown that loss of syndecan expression is observed upon transformation of cells, and that this suppression is due to syndecan gene inactivation (Leppä et al., Cell Regul. 2:1-11 (1991); Inki et al., Am. J. Pathol. 139:1333-1340 (1991); Inki et al., Lab. Invest. 66:314-323 (1992)). This was demonstrated in several biological models of carcinogenesis including models in which transformation is caused by oncogenes, by chemical carcinogens, by UV-light or by hormone-exposure. Thus, syndecan gene suppression is a general phenomenon associated with cellular transformation. All the manipulations of such cells which induce syndecan expression cause these cells to assume a more differentiated phenotype, and thus, reduce their potential tumorigenic behavior and tendency to metastasize.

In order to determine whether steroids were having a direct and causal effect on the transformation of S 115 cells, normal regulatory elements of the syndecan gene were replaced with hormone-inducible elements. As a result of this change, the new cell lines no longer underwent transformation as the result of exposure to steroid.

In a preferred embodiment, the cell in which syndecan expression is stimulated is steroid-responsive. Examples of such steroid-responsive cells include breast cells, endometrium cells and prostate cells, especially in the malignant state. In a highly preferred embodiment, the cell is responsive to estrogen and/or androgen.

Examples of other cell types that will respond to the treatment of the invention include malignant and non-malignant mesenchymal cells.

The regulatory elements of a given gene are commonly located upstream from (i.e., 5 prime to) the transcription initiation site. Syndecan, however, has a very peculiar gene structure, in which the first and second exons are separated by a very large intron (FIG. 1). This could mean that, in addition to base sequences upstream from the transcription site, syndecan expression may also be susceptible to regulation by base sequences located in the first intron.

Nucleotide sequence elements responsible for regulating syndecan gene expression were identified by ligating DNA elements lying upstream of the syndecan gene transcription initiation site to vectors containing the chloramphenicol acetyltransferase (CAT) gene and determining the CAT enzymatic activity expressed by cells transformed with such vectors (see Example VI for experimental details).

Figure 10:
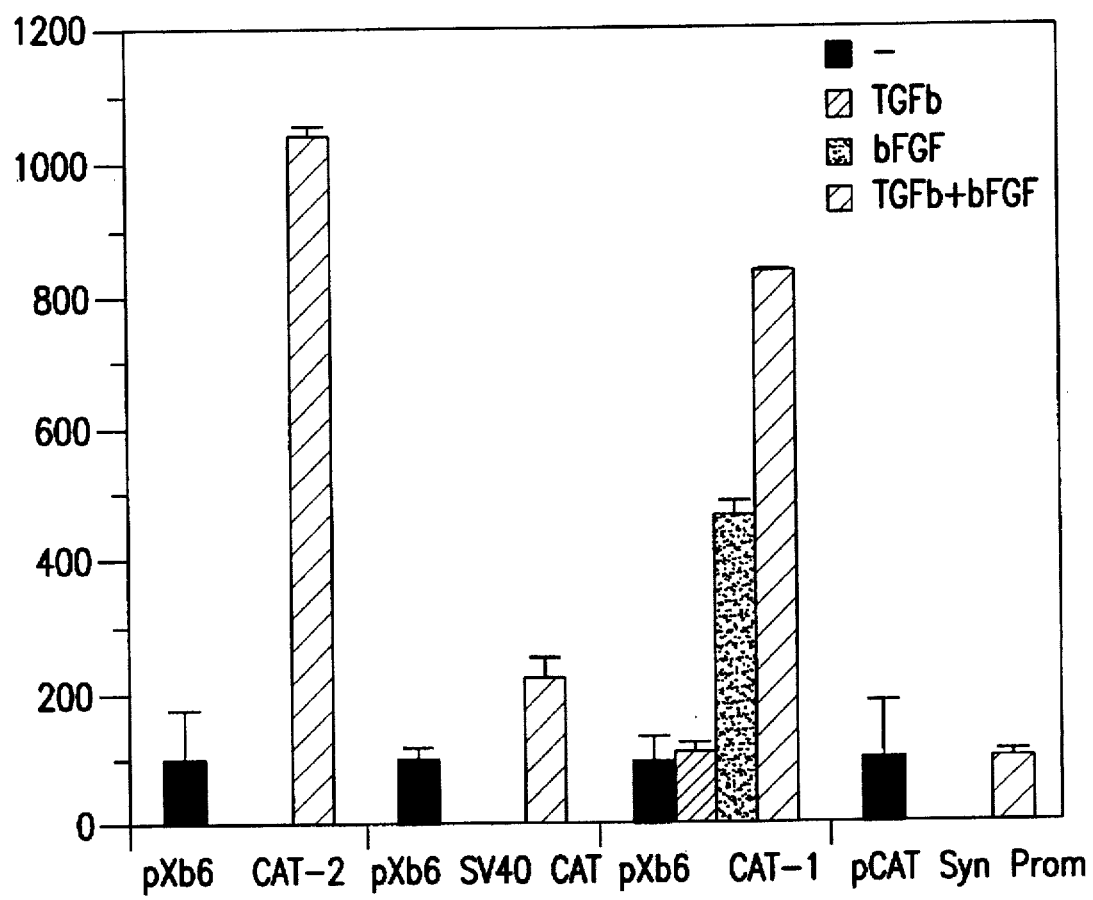
FIG. 10.

It was found that the syndecan gene has a strong enhancer element located approximately 9 kb upstream from the transcription initiation site. Results such as those presented in FIG. 10 indicate that the DNA element shown in FIG. 4 (SEQ ID No. 3) is capable of enhancing expression. Further experiments localized the enhancer to the 350 nucleotide sequence shown as SEQ ID No. 4. DNA encoding the enhancer may be linked to recombinant constructs containing a promoter and a structural gene and may serve to enhance recombinant expression.

Figure 9B:
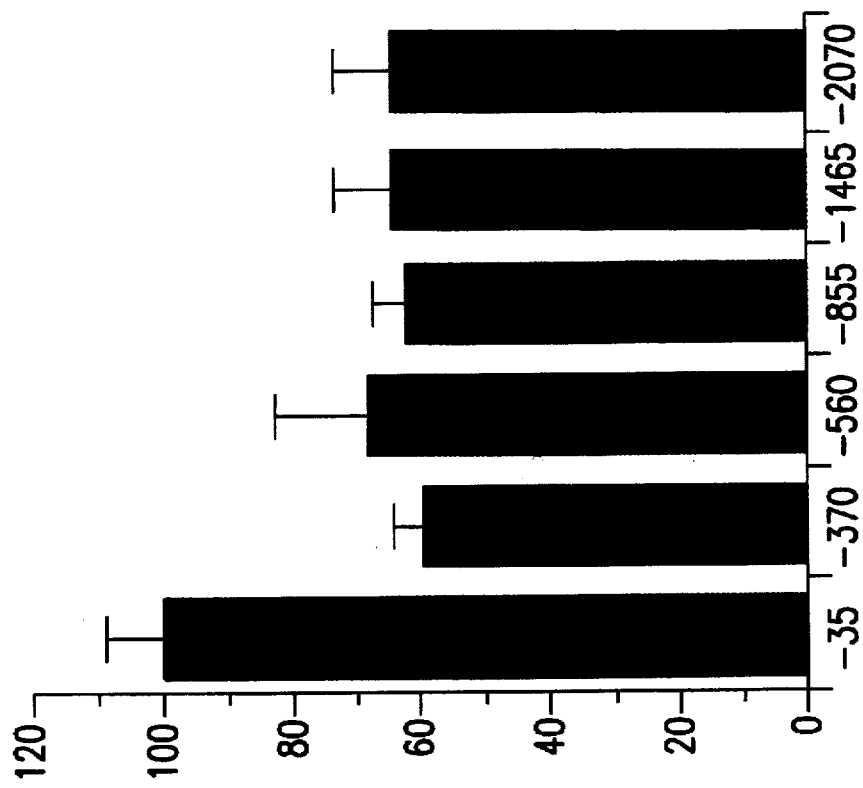
FIGS. 9A–B.
Figure 9A:
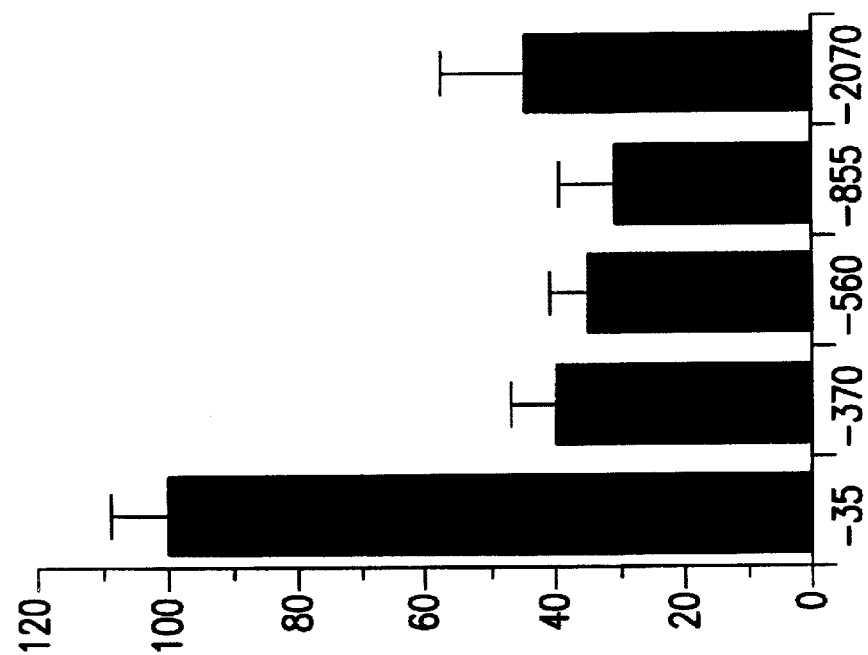

Similar experiments revealed the existence of a sequence element capable of suppressing gene expression (see FIG. 9). The suppressor was localized to nucleotides between -250 and -600 as shown in FIG. 2(a) (SEQ ID No. 1). DNA encoding the suppressor may be linked to recombinant constructs containing a promoter and a structural gene and may serve to suppress recombinant expression. Alternatively, methods may be devised for blocking the suppressive effect of this element in order to promote syndecan expression.

Manipulation of the upstream region of the syndecan gene can block its inactivation during malignant transformation. For example, replacement of the region in front of first exon of the syndecan gene with the glucocorticoid-inducible elements of mouse mammary tumor virus (MMTV) not only blocks syndecan suppression during malignant transformation, but also inhibits the ability or potential of cells to transform and become tumorigenic (FIGS. 5 and 6). These findings suggest a very important role for syndecan in the maintenance of normal epithelial morphology (Leppä et al., Proc. Natl. Acad. Sci. USA 89:932-936 (1992)).

Cells destined to differentiate during organ formation or tissue regeneration also exhibit enhanced syndecan expression (Vainio et al., Dev. Biol. 147:322-333 (1991); Elenius et al., J. Cell Biol. 114:585-595 (1991)). The component(s) responsible for the regulation of syndecan expression (either directly or indirectly) have not yet been identified. Growth factors are candidates for this role since they are known to be involved in the regulation of early development and cellular differentiation (Heath et al., Curr. Opin. Cell Biol. 3:935-938 (1991)). The suggestion that growth factors are involved is also supported indirectly by the fact that the expression of two embryonally important growth factors (TGF-β and FGF) has been shown to coincide with syndecan expression in developing tooth (Vaahtokari et al., Development 113:985-994 (1991); Wilkinson et al., Development 105:131-136 (1989)).

Figure 7:
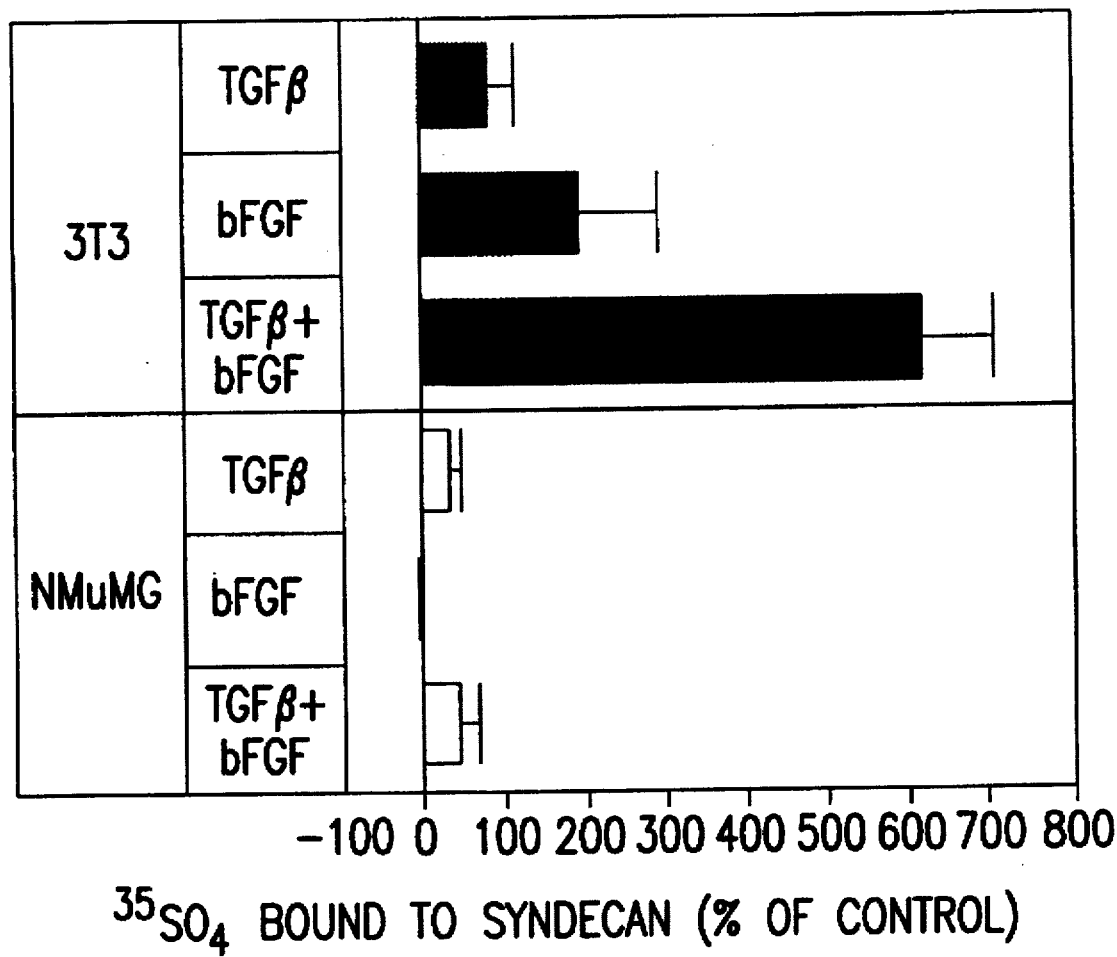
FIG. 7.

Based upon these findings, the possible effect of growth factors on the expression of syndecan has been tested and results are reported herein. It was shown that both bFGF and TGF-β enhance syndecan expression by 3T3 cells, especially if these agents are administered together (FIG. 7). This stimulation produced syndecan levels close to the levels observed in syndecan-expressing epithelial cells (Elenius et al., J. Biol. Chem. 267:6435-6441 (1992)) prior to their becoming malignant (Leppä et al., Proc. Natl. Acad. Sci. USA 89:932-936 (1992)). The findings suggest that growth factors, and their derived fragments and domains may prove to be valuable tools for the regulation of syndecan expression.

Preferably, for treatment of humans and animals, a drug is administered that results in the enhancement of syndecan expression to levels sufficient to facilitate cellular differentiation in the degenerative stages of tissues. Such drugs are herein termed "syndecan-inducing agents." Syndecan-inducing agents include growth factors and the derivatives of such factors that retain growth-factor activity. Examples of such growth factors include bFGF, and TGF-β, whether administered separately or together.

Figure 8:
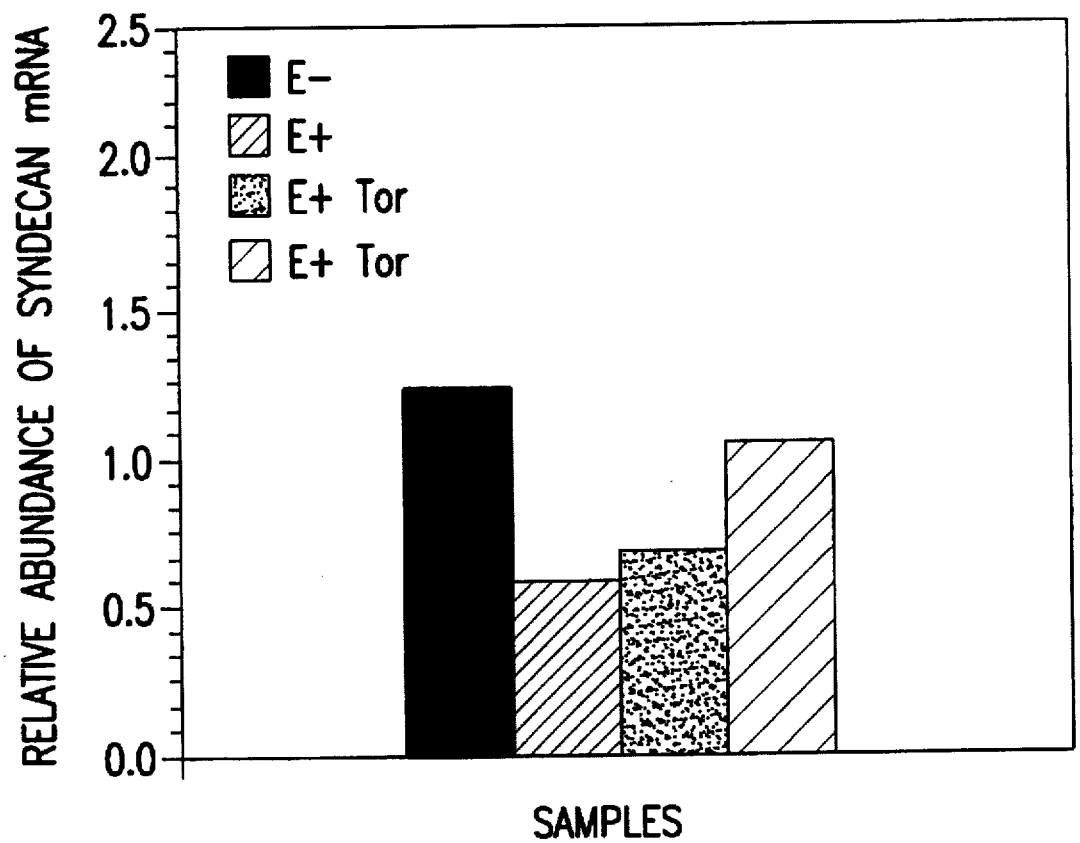
FIG. 8.

Even more preferred is a syndecan-inducing agent that has good tissue and cell penetration so that it can directly interfere with suppressor(s) of syndecan expression within cell nuclei. Such a syndecan-inducing agent is the antitumor drug toremifene. When toremifene, known to have good plasma membrane penetration, is administered to the hormone-transformed epithelial cells with reduced syndecan expression, the cells reverse their lowered syndecan expression, and evidence a syndecan level close to that observed in normal, non-transformed cells (FIG. 8). This demonstrates that syndecan-inducing agents useful in the methods of the invention are known and available and that such agents can specifically prevent cells from becoming malignant by blocking suppression of syndecan expression. Another useful drug in this regard is tamoxifen.

Syndecan-inducing agents may be administered using currently available preparations, or in any pharmaceutically acceptable vehicle. The route of administration may be any route that delivers efficacious levels of the drug to the desired active site, for example, by injection.

For parenteral administration, preparations containing one or more syndecan-inducing agents may be provided to the patient in need of such treatment in combination with pharmaceutically acceptable sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The syndecan-inducing agent of the invention can be employed in dosage forms such as tablets, capsules, powder packets, or liquid solutions for oral administration provided that the biological activity of the syndecan-inducing agent is not destroyed by the digestive process and that the characteristics of the compound allow it to be absorbed across intestinal tissue.

Syndecan-inducing agents may also be administered by a means of pumps, or in sustained-release form. The syndecan-inducing agents used in the method of invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated.

The composition containing the syndecan-inducing agent can be manufactured in a manner which is in itself known, for example, by means of conventional mixing, granulating, dragee-making, dissolving, lyophilizing or similar processes. The compositions of the present invention that provide the syndecan-inducing agent find utility in their ability to slow or prevent tumor growth or tumor reappearance. The syndecan-inducing compositions of the invention utilize the body's own mechanisms for promoting differentiation of specific cell types.

In intravenous dosage form, the compositions of the present invention have a sufficiently rapid onset of action to be useful in the acute management of tumor growth. Additionally, a low potency version is useful in the management of disorders wherein a tumor has been effectively treated and the patient appears to be in remission, but it is desired to maintain sufficient levels of syndecan-inducing agents in the patient so as to assist the body in preventing a recurrence of the tumor.

Typical doses of toremifene or tamoxifen, and other such syndecan-inducing agents useful in the methods of the invention for treatment of humans or other animals are 20–600 mg daily, and preferably 20–60 mg daily.

The Examples below are for illustrative purposes only and are not intended to limit the scope of the invention.

EXAMPLE I

Reversal of hormone-induced transformation by exogenous syndecan expression.

As previously described (Leppä et al., Cell Regulation 2:1–11 (1991)), S115 mouse mammary tumor cells were routinely cultured in DMEM. For experimental studies involving hormone treatment, inactivated fetal calf serum (i-FCS) was replaced with 4% dextran charcoal-treated fetal calf serum (DCC-FCS), which eliminates endogenous steroids from serum, and used either with or without testosterone (10 nM) and with or without dexamethasone (10 nM or 1 μM). Cells were plated at a density of 10,000 cells/cm$^2$ and the medium was replenished every 3 days.

Plasmid pUC19-hsynpr7 containing human syndecan cDNA (Mali et al., J. Biol. Chem. 265:6884–6889 (1990)) was digested with NaeI restriction endonuclease, and the derived 336 bp long-fragment was separated in and eluted from low melting agarose gel. Plasmid pUC19-hsyn4 (Mali et al., J. Biol. Chem. 265:6884–6889 (1990)) was digested with NaeI and HindII (polylinker site), and the plasmid-containing fragment starting from base 487 was isolated. The NaeI fragment from hsynpr7 was ligated to the pUC-hsyn NaeI/HindII digested vector. The orientation of the insert was verified by restriction enzyme analysis and sequencing. The derived plasmid, containing the full coding region of human syndecan core protein, was named pUC19-hsynfull. This plasmid was further digested with BamHI and SphI (polylinker site). A fragment containing syndecan coding region bases 150–1461 was isolated and blunt-ended, using Klenow and T4 DNA polymerase. Finally, this fragment was ligated to SalI-linearized and blunt-ended pMAM-neo vector (Clontech; Palo Alto, Calif.), resulting in a chimeric gene containing a RSV-MMTV-LTR promoter connected to the human syndecan coding region and to an SV-40 polyadenylation signal. The orientation was confirmed by restriction enzyme digestions. The plasmid was named pMAMneo-hsyn.

For control transfections, a 642 bp long-HindIII/PvuII fragment of the human growth hormone gene (consisting of exons 4 and 5; Bornstein et al., J. Biol. Chem. 263:1603–1606 (1988)) was blunt-ended and cloned into the same pMAMneo vector, as described above. This control construct was named pMAMneo-hGH.

All plasmids were isolated using the CsCI density gradient method. Before transfections, plasmids were linearized with MluI, chloroform/phenol extracted and ethanol precipitated.

Transfections were performed using Lipofectin™ (BRL), according to manufacturer's instructions. After selection for two weeks (G418; 750 μg/ml, Sigma), surviving clones were isolated from growth plates using cloning cylinders. The expression of human syndecan or growth hormone (consisting of exons 4 and 5) mRNAs was then confirmed by RNA isolation and Northern blot analysis. Clones expressing high levels of transfected genes were selected for further studies and characterizations. These stock cells were routinely cultured in the presence of G418 (300 μg/ml).

For the measurement of exogenous syndecan expression total RNA was isolated from wild-type S115 cells and cells transfected with human syndecan or growth hormone genes. RNA was extracted using 4M guanidine isothiocyanate and CsCl pelleting, as earlier described by Chirgwin et al., Biochemistry 18:5294–5299 (1979)). RNA from normal mouse mammary NMuMG and normal human mammary HBL-100 cells was used for comparison. RNA aliquots of 15 μg were separated in 1% formaldehyde agarose gels by electrophoresis and transferred to a GeneScreen Plus™ hybridization membrane (New England Nuclear). Blots were hybridized with multiprime (Amersham) labeled inserts of either mouse (PM-4) (Saunders et al., *J. Cell Biol.* 108:1547–1556 (1989)) or human syndecan (pUC19-hsyn4 BamHI 1.1 kb fragment) (Mali et al., *J. Biol. Chem.* 265:6884–6889 (1990)), or with human growth hormone exons 4 and 5 (hGH) (Leppä et al., *Proc. Natl. Acad. Sci. USA* 89:932–936 (1992)) cDNAs, using the high stringency conditions suggested by the manufacturer of the membrane (New England Nuclear). All techniques based on modern molecular biology are fully explained in the literature such as in the laboratory manual entitled *Current Protocols in Molecular Biology*.

Anchorage independent cell growth was measured in a soft agar colony assay. The six well-plates were first covered with an agar layer consisting of 2 ml DMEM, 0.5% agar and 4% DCC-FCS. The middle layer contained $10^4$ cells in 0.5 ml DMEM supplemented with 0.33% agar and 4% DCC-FCS, with or without 10 nM testosterone. The uppermost layer, consisting of medium (2 ml), was added to prevent drying of the agarose gels. The plates were incubated at 37° C. in 5% $CO_2$ for 12 days after which cultures were evaluated and photographed.

Tumorigenicity of S115 wild type cells, one hGH transfected control clone and two clones expressing human syndecan-1 was measured in nude mice. Cells were cultured in DMEM containing 5% FCS and 10 nM testosterone. After four days in culture, cells were harvested with trypsin, washed, and $10^7$ cells suspended in 0.2 ml of DMEM were injected subcutaneously into the backs of athymic male nude mice (balb-C). A silastic testosterone capsule, which is known to increase the growth rate of S115 cells (King et al., *J. Steroid. Biochem.* 7:869–873 (1976)), was simultaneously implanted. Nude mice were examined regularly for tumor development and the size of the palpable tumors measured at intervals.

EXAMPLE II

Growth factors enhance syndecan expression.

NMuMG mouse mammary epithelial cells and 3T3 (NIH) mouse fibroblasts were routinely cultured in bicarbonate-buffered Dulbecco's modified Eagle's medium (DMEM; GIBCO) containing 10% FCS (GIBCO) and antibiotics, as previously described (Elenius et al., *J. Biol. Chem.* 265:17837–17843 (1990)). For experiments, cells were plated at equal density on culture dishes (Nunc) and grown to 60–70% confluency. Twenty-four hours before supplementing the medium with growth factor(s), the medium on the cells was replaced with fresh medium containing 2% CMS-FCS (Vogel et al., *Proc. Natl. Acad. Sci. USA* 75:2810–2814 (1978)). Equally treated cultures without growth factor addition served as negative controls. Porcine TGFβ1 (R&D), recombinant human bFGF (Boehringer) and murine EGF (Sigma) were used in final concentrations of 2.5 ng/ml (100 pM), 10 ng/ml (570 pM) and 1.2 ng/ml (200 pM) respectively, in all experiments. For quantitation and isolation of cell surface syndecan, media were discarded at time points indicated in the text and the cell layers were washed twice with ice cold phosphate buffered saline (PBS). Cells were scraped with a rubber policeman into ice cold PBS supplemented with 0.5 mM EDTA and centrifuged. After subsequent washes by resuspension and centrifugation the cell numbers were measured by counting the nuclei with a Coulter Counter (Coulter Electronics).

For quantitation of syndecan intercalated into the cell membrane, syndecan ectodomain was released by incubating washed cells in 20 µg/ml bovine pancreatic trypsin (Type III; Sigma) in PBS for 10 min on ice bath. After incubation the cells were centrifuged, leaving the ectodomain in the supernatant (Rapraeger et al., *J. Biol. Chem.* 260:11046–11052 (1985)). Sample volumes equal to 400,000 or 200,000 cells for 3T3 or NMuMG cells, respectively, were loaded onto a cationic nylon membrane (Zeta-Probe; BioRad) in a minifold-slot apparatus (Sehleicher and Schuell), as previously described (Jalkanen et al., *J. Cell Biol.* 105:3087–3096 (1987)). Nonspecific binding was blocked by incubating the membrane for one hour at room temperature in PBS containing 10% FCS. Syndecan attached to the membrane was detected with a monoclonal antibody against mouse syndecan core protein (mAB 281-2) (Jalkanen et al., *J. Cell Biol.* 101:976–984 (1985)) that was radioiodinated by the chloramine-T oxidation method (St ähli et al., *Meth. Enzymol.* 92:242–253 (1983)). The membrane was incubated overnight at 4° C. with $^{125}$I-labeled 281-2 in PBS+10% FCS (10,000 CPM/ml). After five washes with PBS the bound antibody was visualized by autoradiography.

The accumulation of syndecan ectodomain into the medium was estimated by taking samples corresponding to 1/50 (3T3 cells) or 1/100 (NMuMG cells) of the total volume of the remaining medium at selected time points. The samples were analyzed by loading them onto a nylon membrane as described above. The autoradiography signal was quantitated with a GelScan XL ultroscan densitometer (LKB) using GelScan XL 2400 software (LKB).

For syndecan purification, cells were radiolabeled for 24 hours in low sulfate DMEM ($MgCl_2$ substituted for $MgSO_4$; 2% CMS-FCS) with 100 µCi/ml $^{35}SO_4$ (New England Nuclear) in the presence or absence of growth factor(s). Cell surface trypsin-releasable material was collected, as described above, and after dialysis against Tris-buffered saline (TBS), the sample was loaded onto a 281-2-Sepharose CL-4B immunoaffinity column (Jalkanen et al., *J. Cell Biol.* 105:3087–3096 (1987)). Bound material was eluted with 50 mM triethylamine (TEA) (pH 11.5) and the amount of radioactive PG in each fraction was analyzed using cetylpyridiumchloride-impregnated Whatman 3 MM filter discs (Rapraeger et al., *J. Biol. Chem.* 260:11046–11052 (1985)). For interaction experiments, fractions containing most of the labeled PG were pooled and dialyzed against PBS.

To obtain unlabeled syndecan ectodomain for interaction assays (see below) the same procedure was used except that no radioactive sulfate was added to the culture medium and the syndecan containing fractions eluted from the immunoaffinity column were detected by immuno-dot assay using mAB 281-2. The estimation of the molar concentration of syndecan was based on the use of previously determined syndecan concentration by total amino acid analysis (Jalkanen et al., *J. Cell Biol.* 106:953–962 (1988)).

SDS-PAGE and Western Blot—For western blot experiments, cells were cultured 24 hours with or without growth factor(s). Syndecan ectodomain containing material released from the cell surface by trypsin treatment was fractionated on SDS-PAGE gradient (2–15%) gel (O'Farrel, *J. Biol. Chem.* 250:4007–4021 (1975)). After electrophoresis, samples were transferred onto a Zeta-Probe membrane by electroblotting with a 2005 Transphor apparatus (LKB). The syndecan antigen on the filter was detected with radioiodinated mAB 281-2 and the filter was washed, as described above for slot blot analysis.

Northern Blot—RNA was isolated from 3T3 and NMuMG cells using 4M guanidine isothiocyanate and CsCl density centrifugation (Chirgwin et al., *Biochemistry* 18:5294–5299 (1979)). RNA samples were size-separated on a 1% agarose formaldehyde gel, transferred to a Gene-Screen Plus™ membrane (New England Nuclear) and hybridized with a multi-prime (Amersham) labeled partial cDNA clone for mouse syndecan (PM-4) (Saunders et al., *J. Cell Biol.* 108:1547–1556 (1989)). After hybridization, the membrane was washed in 2×SSC and 1.0% SDS at 65° C. (high stringency conditions). For rehybridization with glyceraldehyde-3-phosphate-dehydrogenase (GAPDH; Fort et al., *Nucleic Acid Res.* 13:1431–1442 (1985)), the bound PM-4 probe was removed as recommended by the manufacturer of the filter (NEN).

EXAMPLE III

Induction of syndecan mRNA expression in human breast cancer cells (MCF-7) growth-inhibited with toremifene.

The steroid-responsive human breast cancer cell line MCF-7 was used to study the expression of human syndecan under different growth conditions regulated by estrogen and anti-estrogen. Cells were plated at a density of $1.2 \times 10^6$ cells/100 mm of plastic culture dish and grown as monolayer cultures in 10 ml per dish of phenol red-free DMEM medium with 5% dextran/charcoal treated fetal calf serum (DS-FCS), 2 mM L-glutamine and 3 µg/ml insulin. For hormone-treatment, 1 nM of 17β-O-estradiol ($E_2$), alone or with 1–6.25 µM toremifene, dissolved 70% in ethanol, was added to the culture medium on the day following plating. The cells were cultured for 6 days, and the media were changed every second day. For RNA extraction, cells were washed in situ with PBS and scraped from the plates in 4M guanidine isothiocyanate.

EXAMPLE IV

Treatment of Steroid-Responsive Tumors in Patients.

Patients diagnosed as having a steroid-responsive tumor selected from a breast tumor, an endometrium tumor, a prostate gland tumor or a mesenchymal tissue tumor are administered a composition that contains efficacious amounts of the anti-steroid agent toremifene or tamoxifen, or efficacious amounts of the growth factor bFGF, TGF-β or bFGF together with TGF-β, in amounts ranging from 20–600 mg per day, depending upon the extent of the tumor, the patient's age, the patient's sex, and other treatments such as are taken into consideration in designing such chemotherapeutic protocols. The syndecan-inducing agent is administered for a period of time sufficient to increase syndecan levels in the tumor cells, such that the tumor cells now assume a more differentiated phenotype and such that the growth of the tumor is arrested or significantly slowed by the treatment.

EXAMPLE V

Stimulation of Hair Growth in Epidermal Skin Cells.

Patients diagnosed as being in need of increased hair growth in the scalp region are administered a composition that contains efficacious amounts of the anti-steroid agent toremifene or tamoxifen, or efficacious amounts of the growth factor bFGF, TGF-β or bFGF together with TGF-β, in amounts ranging from 20–600 mg per day, depending upon the extent of the needed hair growth, the patient's age, the patient's sex, and other treatments such as are taken into consideration in designing such protocols. The syndecan-inducing agent is administered for a period of time sufficient to increase syndecan levels in the epidermal cells, such that hair growth is significantly increased by the treatment.

EXAMPLE VI

Determination of Mouse Syndecan Promoter and Enhancer Activities.

The mouse syndecan gene has been cloned and characterized up to −10 kbs upstream from the transcription start site. To determine the specific activities of different proximal promoter regions (up to −2 kbs from the start site) and enhancer regions (from −2 to −10 kbs) we have made plasmid constructs in which these regions were cloned into pCAT basic or pCAT promoter vectors, containing the CAT reporter gene. The reporter CAT gene produces the enzyme chloramphenicol acetyltransferase, which transfers the n-butyryl moiety of n-butyryl CoA to chloramphenicol. The n-butyryl chloramphenicol can be separated from native chloramphenicol by extraction with xylene.

For the proximal promoter, a deletion series was made (Hind III, Hind II, Bgl II, Stu I, Dra I, Cla I, BamHI and Pst I-Xho I) and the resulting fragments were cloned into the pCAT basic vector. For enhancer areas, three Xba I fragments were cloned into a pCAT promoter vector, where the SV 40 promoter was displaced by the Bgl II-Xho I fragment from the syndecan promoter.

The plasmid constructs were transiently transfected into eukaryotic cells by calcium phosphate precipitation simultaneously with a β-Galactosidase expressing vector to determine transfection efficiency. After a four hour incubation, cells were treated with 15% glycerol and grown for approximately 48 h in cell culture medium. Cells were then scraped from dishes in TEN-buffer and the cytoplasmic extract was obtained by repeated freezing and thawing. β-Galactosidase activity was obtained in the cytoplasmic extract by adding 0.1M sodium phosphate, 45 mM mercaptoethanol and 0.2 mg O-nitrophenyl-s-galactopyranoside (ONGP). This was incubated from 2 hours to overnight and the color reaction was measured spectrophotometrically at 420 nm.

CAT activity was determined by adding 0.25M Tris buffer, 25 ng n-butyryl CoA and 0.0626 µCi of $^{14}$C-chloramphenicol to the cytoplasmic extract. Samples were incubated overnight, extracted with xylene and the radioactivity present was measured by scintillation counting. CAT activity was corrected for transfection efficiency as determined by assays of β-galactosidase activity.

The cells used for proximal promoter constructs were 3T3 NIH, S115 (either hormone-treated or not) and nMuMG cells. For enhancer constructs we used 3T3 NIH cells grown in 2% CMS medium. 3T3 NIH cells were also used to test the effect of growth factors in 2% CMS medium with 10 ng/ml FGF-2 and 2 ng/ml TGF/β-1.

By measuring the CAT activity present in transfected cells, the effect of inserted syndecan gene regions on gene transcription was determined. Results indicated that both a suppressor element (FIG. 9) and an enhancer element (FIG. 10) are upstream of the syndecan transcription initiation site. The suppressor element is located between 250 and 600 base pairs upstream from the transcription initiation site. The enhancer element is located between 8,600 and 9,300 base pairs upstream from the syndecan transcription initiation site.

All references cited herein are fully incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A purified DNA molecule having the sequence of nucleotides of SEQ ID NO:3.

2. A purified DNA molecule comprising a fragment of SEQ ID NO:3; wherein said fragment of SEQ ID NO :3 enhances expression of a gene operably linked to the promoter of the mouse syndecan gene of SEQ ID NO: 1 in 3T3 cells following treatment with TGF-β and bFGF when said fragment is operably linked to said promoter.

3. A purified DNA molecule having the sequence of nucleotides of SEQ ID NO:4.

4. A purified DNA molecule comprising a fragment of SEQ ID NO:4; wherein said fragment of SEQ ID NO:4 enhances expression of a gene operably linked to the promoter of the mouse syndecan gene of SEQ ID NO: 1 in 3T3 cells following treatment with TGF-β and bFGF when said fragment is operably linked to said promoter.

5. A vector comprising the DNA molecule of any one of claims 1-4.

6. A host cell transfected with the vector of claim 5.

7. A purified DNA molecule having the sequence of nucleotides of −250 to −600 of FIG. 2 (nucleotides 3538–3888 of SEQ ID NO:1).

8. A purified DNA molecule comprising a portion of the sequence of nucleotides of −250 to −600 of FIG. 2 (nucleotides 3538–3888 of SEQ ID NO:1); wherein said portion of the sequence of nucleotides of −250 to −600 of FIG. 2 (nucleotides 3538–3888 of SEQ ID NO: 1) suppresses expression of a gene operably linked to the promoter of the mouse syndecan gene of SEQ ID NO:1 in S115 cells treated with testosterone when said portion is operably linked to said promoter.

9. A vector comprising the DNA molecule of either claim 7 or 8.

10. A host cell transformed with the vector of claim 9.

* * * * *

UNITED STATES PATENT AND TRADEMARK OFFICE
CERTIFICATE OF CORRECTION

PATENT NO. : 5,726,058

DATED : March 10, 1998

INVENTOR(S) : Jalkanen *et al.*

It is certified that error appears in the above-indentified patent and that said Letters Patent is hereby corrected as shown below:

Title page, at lines 1 and 2 of item [54], please delete "Syndecan Stimulation of Cellular Differentiation" and insert therefor --DNA Molecules, Vectors, and Host Cells Comprising a Syndecan Enhancer Element and a Syndecan Suppressor Element--.

The same should be applied at col. 1, lines 1-2.

Signed and Sealed this

Seventh Day of July, 1998

Attest:

BRUCE LEHMAN

*Attesting Officer*      *Commissioner of Patents and Trademarks*